United States Patent
Brotherton-Pleiss et al.

(10) Patent No.: US 9,580,411 B2
(45) Date of Patent: Feb. 28, 2017

(54) SUBSTITUTED SULFONAMIDE COMPOUNDS

(71) Applicants: Hoffmann-La Roche Inc., Little Falls, NJ (US); GENENTECH, INC., South San Francisco, CA (US)

(72) Inventors: Christine E. Brotherton-Pleiss, Sunnyvale, CA (US); Huifen Chen, Burlingame, CA (US); Shaoqing Chen, Bridgewater, NJ (US); Zhi Chen, Livingston, NJ (US); Shawn David Erickson, Leonia, NJ (US); Anthony Estrada, San Carlos, CA (US); Kyungjin Kim, Livingston, NJ (US); Hongju Li, Edison, NJ (US); Allen John Lovey, North Caldwell, NJ (US); Joseph P. Lyssikatos, Piedmont, CA (US); Yimin Qian, Wayne, NJ (US); Sung-Sau So, Verona, NJ (US); Peter Michael Wovkulich, New York, NY (US); Lin Yi, Basking Ridge, NJ (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/671,643

(22) Filed: Mar. 27, 2015

(65) Prior Publication Data
US 2015/0197509 A1 Jul. 16, 2015

Related U.S. Application Data

(63) Continuation of application No. PCT/EP2013/070055, filed on Sep. 26, 2013.
(Continued)

(51) Int. Cl.
| | | |
|---|---|---|
| *C07D 305/08* | (2006.01) |
| *C07D 409/12* | (2006.01) |
| *C07D 231/18* | (2006.01) |
| *C07D 401/04* | (2006.01) |
| *C07D 401/12* | (2006.01) |
| *C07D 403/04* | (2006.01) |
| *C07D 237/08* | (2006.01) |
| *C07D 239/42* | (2006.01) |
| *C07D 409/14* | (2006.01) |
| *C07D 241/12* | (2006.01) |
| *C07D 213/26* | (2006.01) |
| *C07D 213/40* | (2006.01) |

(Continued)

(52) U.S. Cl.
CPC .......... *C07D 409/12* (2013.01); *C07C 311/16* (2013.01); *C07C 311/17* (2013.01); *C07C 311/19* (2013.01); *C07C 311/20* (2013.01); *C07D 213/26* (2013.01); *C07D 213/40* (2013.01); *C07D 231/18* (2013.01); *C07D 237/08* (2013.01); *C07D 239/26* (2013.01); *C07D 239/42* (2013.01); *C07D 241/12* (2013.01); *C07D 305/06* (2013.01); *C07D 305/08* (2013.01); *C07D 401/04* (2013.01); *C07D 401/12* (2013.01); *C07D 403/04* (2013.01); *C07D 403/12* (2013.01); *C07D 409/14* (2013.01); *C07C 2101/02* (2013.01)

(58) Field of Classification Search
CPC .. C07D 231/18; C07D 403/12; C07D 401/12; C07D 403/04; C07D 237/08; C07D 239/42; C07D 409/12; C07D 409/14; C07D 241/12; C07D 213/26; C07D 213/40; C07D 305/08; C07C 311/19; C07C 2101/02; C07C 311/17; C07C 311/16
See application file for complete search history.

(56) References Cited

U.S. PATENT DOCUMENTS

| 7,973,078 | B2 | 7/2011 | Kubota et al. | |
| 8,637,529 | B2 * | 1/2014 | Woller | C07D 487/04 514/262.1 |
| 2015/0218141 | A1 * | 8/2015 | Brotherton-Pleiss | C07D 223/04 514/217.12 |

FOREIGN PATENT DOCUMENTS

| EP | 2 050 446 A1 | 4/2009 |
| WO | 00/50391 A1 | 8/2000 |

(Continued)

OTHER PUBLICATIONS

STN CAS Registry Nos. (2007).*
STN CAS Registry Nos. (2009).*
Database PubChem Compound [online] NCBI: Jul. 30, 2006; XP002716604; Database accession No. AC1P9N70 the whole document.
Database PubChem Compound [online] NCBI: Jul. 30, 2006; XP002716605; Database accession No. AC1P9NA3 the whole document.
Database PubChem Compound [online] NCBI: May 29, 2009; XP002716594; Database accession No. AKOS006978082 the whole document.
(Continued)

*Primary Examiner* — Alexander R Pagano
(74) *Attorney, Agent, or Firm* — Robert C. Hall

(57) ABSTRACT

The invention is concerned with the compounds of formula (I):

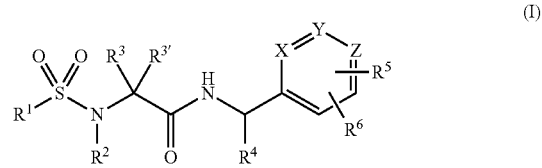

and salts thereof, wherein X, Y, Z, $R^1$, $R^2$, $R^3$, $R^{3'}$, $R^4$, $R^5$ and $R^6$ are defined in the detailed description and claims. In addition, the present invention relates to methods of manufacturing and using the compounds of Formula (I) as well as pharmaceutical compositions containing such compounds. The compounds may be useful in treating diseases and conditions mediated by TRPA1, such as pain.

14 Claims, No Drawings

Related U.S. Application Data

(60) Provisional application No. 61/706,286, filed on Sep. 27, 2012.

(51) Int. Cl.
  *C07C 311/19* (2006.01)
  *C07C 311/16* (2006.01)
  *C07C 311/17* (2006.01)
  *C07C 311/20* (2006.01)
  *C07D 239/26* (2006.01)
  *C07D 305/06* (2006.01)
  *C07D 403/12* (2006.01)

(56) References Cited

FOREIGN PATENT DOCUMENTS

| WO | 2008/018544 A1 | 2/2008 |
| WO | 2010/141805 A1 | 12/2010 |
| WO | 2013/130703 A2 | 9/2013 |

OTHER PUBLICATIONS

Database PubChem Compound [online] NCBI: May 30, 2009; XP002716603; Database accession No. AKOS006899272 the whole document.
Database PubChem Compound [online] NCBI: Nov. 25, 2011; XP002716602; Database accession No. T6776903 the whole document.
Database PubChem Compound [online] NCBI: May 3, 2011; XP002716600; Database accession No. T6810969 the whole document.
Database PubChem Compound [online] NCBI: May 3, 2011; XP002716601; Database accession No. T6793632 the whole document.
Database PubChem Compound [online] NCBI: May 20, 2011; XP002716599; Database accession No. ZINC58193848 the whole document.
Database PubChem Compound [online] NCBI: Jan. 25, 2012; XP002716595; Database accession No. AKOS007865415 the whole document.
Database PubChem Compound [online] NCBI: Jan. 25, 2012; XP002716597; Database accession No. AKOS007803697 the whole document.
Database PubChem Compound [online] NCBI: Jan. 25, 2012; XP002716598; Database accession No. AKOS007276660 the whole document.
Database PubChem Compound [online] NCBI: Mar. 8, 2012; XP002716596; Database accession No. MolPort-019-801-259 the whole document.
International Preliminary Report on Patentability issued in International Application No. PCT/EP2013/070055, dated Dec. 16, 2014, in 6 pages.
International Search Report issued in International Application No. PCT/EP2013/070055, dated Dec. 10, 2013, in 5 pages.

\* cited by examiner

SUBSTITUTED SULFONAMIDE COMPOUNDS

CROSS REFERENCE TO RELATED APPLICATIONS

This application is a continuation of International Application No. PCT/EP2013/070055 having an international filing date of Sep. 26, 2013, the entire contents of which are incorporated herein by reference, and which claims benefit under 35 U.S.C. §119 to U.S. Provisional Patent Application No. 61/706,286 filed Sep. 27, 2012, the entire contents of which are incorporated herein by reference.

FIELD OF THE INVENTION

The present invention relates to substituted sulfonamide compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a nonselective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor.'

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., *J. Neurosci* 27, (2007) 4443-4451; Kremayer et al., *Neuron* 66 (2010) 671-680; Wei et al., *Pain* 152 (2011) 582-591); Wei et al., *Neurosci Lett* 479 (2010) 253-256)) providing additional rationale for the utility of small molecule TRPA1 inhibitors in the treatment of pain disorders.

SUMMARY OF THE INVENTION

The invention provides a compound of the invention which is a compound of formula (I):

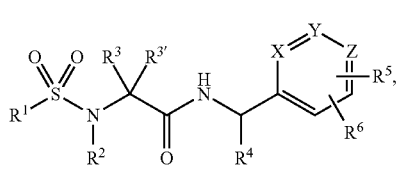

wherein:
X, Y, Z are, independently of each other, C, CH or N;
$R^1$ is unsubstituted phenyl, phenyl mono- or bi-substituted independently with halogen or —CN, an unsubstituted five- or six-membered heteroaryl ring or a five- or six-membered heteroaryl ring substituted with lower alkyl, halogen, or haloalkyl;
$R^2$ is selected from the group consisting of hydrogen, deuterium, lower alkyl, haloalkyl, cycloalkyl, alkoxy, oxetanyl, phenyl and a five or six membered heteroaryl ring, wherein said lower alkyl, haloalkyl, cycloalkyl, alkoxy or oxetanyl is optionally substituted with deuterium and wherein said phenyl and said five or six membered heteroaryl ring are each independently optionally substituted with lower alkyl, haloalkyl, deuterium or halogen;
$R^3$ and $R^{3'}$ are each independently selected from the group consisting of hydrogen; deuterium; haloalkyl; cycloalkyl and lower alkyl wherein said haloalkyl, cycloalkyl and lower alkyl is optionally substituted with deuterium, F, Cl, Br, hydroxyl or alkoxy; or $R^3$ and $R^{3'}$ taken together with the carbon to which they are attached form a 3, 4, 5, or 6-membered cycloalkyl optionally substituted with deuterium, F, Cl, Br, hydroxyl or alkoxy;
$R^4$ is hydrogen or lower alkyl;
$R^5$ is trifluoromethyl-phenyl, trifluoromethyl-pyridinyl, trifluoromethyl-pyridazinyl, trifluoromethyl-pyrimidinyl, azetidino, pyrrolidino, cycloalkyl, piperidino, pyrrolidino-pyrimidinyl, heterocycle, heterocycle-pyrimidinyl, heterocycle-pyridinyl, heterocycle-pyridazinyl, heterocycle-pyrazinyl, cycloalkyl-pyrimidinyl, cycloalkyl-pyridinyl, cycloalkyl-pyridazinyl, cycloalkyl-pyrazinyl, or trifluoromethyl-pyrazinyl, wherein any azetidinyl, pyrrolidino, cycloalkyl, heterocycle, and piperidino is optionally substituted with lower alkyl, halogen, trifluoromethyl, trifluoromethoxy or trifluoromethylthio; and
$R^6$ is hydrogen, halogen or alkoxy;
or a pharmaceutically acceptable salt thereof.

The invention also provides a pharmaceutical composition comprising a compound of the invention and a pharmaceutically acceptable carrier.

The invention also provides a compound of the invention or a pharmaceutically acceptable salt thereof for use in medical therapy.

The invention also provides for a compound of the invention or a pharmaceutically acceptable salt thereof for the treatment or prophylaxis of a respiratory disorder.

The invention provides for the use of a compound of the invention or a pharmaceutically acceptable salt thereof for the preparation of a medicament for the treatment or prophylaxis of a respiratory disorder.

The invention also provides for a method for treating a respiratory disorder in a mammal comprising, administering a compound of the invention or a pharmaceutically acceptable salt thereof to the mammal.

The invention also provides for a compound of the invention or a pharmaceutically acceptable salt thereof for modulating TRPA1 activity.

In another embodiment, the invention provides for a compound of the invention or a pharmaceutically acceptable salt thereof for the treatment or prophylaxis of a disease or condition mediated by TRPA1 activity. Within aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain, arthritis, itch, cough, asthma, inflammatory bowel disease, or an inner ear disorder.

In another embodiment, the invention provides for the use of a compound of the invention or a pharmaceutically acceptable salt thereof for the preparation of a medicament for the treatment or prophylaxis of a disease or condition that is mediated by TRPA1 activity. Within aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the central nervous system (CNS) or CNS hypoxia. Within aspects of this embodiment, the disease or condition is pain, arthritis, itch, cough, asthma, inflammatory bowel disease, or an inner ear disorder.

In another embodiment, the invention provides for a method for modulating TRPA1 activity, comprising contacting TRPA1 with a compound of the invention or a salt thereof.

In another embodiment, the invention provides for a method for treating a disease or condition mediated by TRPA1 activity in a mammal, comprising administering a compound of the invention or a pharmaceutically acceptable salt thereof to the mammal. Within certain aspects of this embodiment, the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain, arthritis, itch, cough, asthma, inflammatory bowel disease, or an inner ear disorder.

The invention also provides an invention as described herein.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^6$ of Formula (I) refer to moieties that are attached to the core structure of Formula (I) by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "alkoxy" denotes a group of the formula —O—R', wherein R' is an alkyl group. Examples of alkoxy moieties include methoxy, ethoxy, isopropoxy, and tert-butoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a monovalent saturated carbocyclic moiety having mono- or bicyclic rings and 3 to 10 carbon atoms. The cycloalkyl moiety can optionally be substituted with one or more substituents. In particular embodiments cycloalkyl contains from 3 to 8 carbon atoms. In other particular embodiments cycloalkyl contains from 3 to 6 carbon atoms. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof (e.g. cyclopentenyl, cyclohexenyl, and cycloheptenyl).

"Heterocycle" refers to a 4- to 7-membered monocyclic or 7-10-membered bicyclic heterocyclic moiety that is saturated or partially unsaturated, and has one or more heteroatoms selected from oxygen, nitrogen and sulfur in then ring. When used in reference to a ring atom of a heterocycle, a nitrogen or sulfur may also be in an oxidized form, and a nitrogen may be substituted with one or more alkyl groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, phenanthridinyl, 2-azabicyclo [2.2.1]heptanyl, octahydroindolyl, or tetrahydroquinolinyl.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of Formula (I) to be used as prodrugs). The compounds of the present invention can also be solvated, i.e. hydrated. The solvation can be effected in the course of the manufacturing process or can take place i.e. as a consequence of hygroscopic properties of an initially anhydrous compound of Formula (I).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

In one aspect the present invention provides for compounds of formula I as described hereinbelow as a first embodiment of the invention (embodiment "E1"):

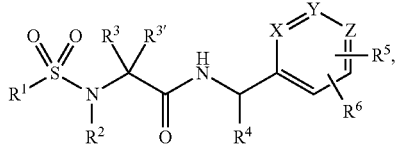

(I)

wherein:
X, Y, Z are, independently of each other, C, CH or N;
$R^1$ is unsubstituted phenyl, phenyl mono- or bi-substituted independently with halogen or —CN, an unsubstituted five- or six-membered heteroaryl ring or a five- or six-membered heteroaryl ring substituted with lower alkyl, halogen, or haloalkyl;

$R^2$ is selected from the group consisting of hydrogen, deuterium, lower alkyl, haloalkyl, cycloalkyl, alkoxy, oxetanyl, phenyl and a five or six membered heteroaryl ring, wherein said lower alkyl, haloalkyl, cycloalkyl, alkoxy or oxetanyl is optionally substituted with deuterium and wherein said phenyl and said five or six membered heteroaryl ring are each independently optionally substituted with lower alkyl, haloalkyl, deuterium or halogen;

$R^3$ and $R^{3'}$ are each independently selected from the group consisting of hydrogen; deuterium; haloalkyl; cycloalkyl and lower alkyl wherein said haloalkyl, cycloalkyl and lower alkyl is optionally substituted with deuterium, F, Cl, Br, hydroxyl or alkoxy; or $R^3$ and $R^{3'}$ taken together with the carbon to which they are attached form a 3, 4, 5, or 6-membered cycloalkyl optionally substituted with deuterium, F, Cl, Br, hydroxyl or alkoxy;

$R^4$ is hydrogen or lower alkyl;

$R^5$ is trifluoromethyl-phenyl, trifluoromethyl-pyridinyl, trifluoromethyl-pyridazinyl, trifluoromethyl-pyrimidinyl, azetidino, pyrrolidino, cycloalkyl, piperidino, pyrrolidino-pyrimidinyl, heterocycle, heterocycle-pyrimidinyl, heterocycle-pyridinyl, heterocycle-pyridazinyl, heterocycle-pyrazinyl, cycloalkyl-pyrimidinyl, cycloalkyl-pyridinyl, cycloalkyl-pyridazinyl, cycloalkyl-pyrazinyl, or trifluoromethyl-pyrazinyl, wherein any azetidinyl, pyrrolidino, cycloalkyl, heterocycle, and piperidino is optionally substituted with lower alkyl, halogen, trifluoromethyl, trifluoromethoxy or trifluoromethylthio; and $R^6$ is hydrogen, halogen or alkoxy, or a pharmaceutically acceptable salt thereof.

It is understood that $R^5$ and $R^6$ are each attached to a carbon atom, and that when $R^5$ and/or $R^6$ are attached to one or more X, Y or Z, then said one or more X, Y or Z to which $R^5$ and/or $R^6$ are attached is C.

Additional embodiments (e.g., E2-E25) of the invention are set forth below

E2: The compound according to E1, wherein X, Y and Z are independently of each other C or CH.

E3: The compound according to E1, wherein one of X, Y or Z is N and the others are independently of each other C or CH.

E4: The compound according to E1, wherein two of X, Y or Z are N and the other is C or CH.

E5: The compound according to any one of E1-E4, wherein $R^1$ is unsubstituted phenyl, pyrazinyl, pyridinyl or thiophenyl.

E6: The compound according to any one of E1-E4, wherein $R^1$ is phenyl optionally substituted with cyano, F or Cl, pyrazinyl optionally substituted with F or Cl, pyridinyl optionally substituted with F or Cl, pyrazole optionally substituted with F or Cl, or thienyl, optionally substituted with F or Cl.

E7: The compound according to any one of E1-E4, wherein $R^1$ is phenyl substituted with F or Cl, pyrazinyl substituted with F or Cl, pyridinyl substituted with F or Cl, or thiophenyl substituted with F or Cl.

E8: The compound according to any one of E1-E7, wherein $R^2$ is hydrogen.

E8.1: The compound according to any of E1-E7, wherein $R^2$ is optionally substituted phenyl pyridinyl, pyrimidinyl, pyrazinyl or pyridazinyl.

E8.2: The compound according of any of E1-E7, wherein $R^2$ is deuterium.

E9: The compound according to any one of E1-E7, wherein R² is methyl, —CH₂CF₃, ethyl, hydroxy-ethyl, propyl, hydroxy-propyl, cyclopropyl, isopropyl, methoxy-ethyl, tert-butyl, oxetan-3-ylmethyl or oxetanyl.

E10: The compound according to any one E1-E7, wherein R² is methyl, —CH₂CF₃, ethyl, hydroxy-ethyl, 2-hydroxy-propyl, cyclopropyl, isopropyl, 2-methoxyethyl, tert-butyl, methoxymethyl, oxetan-3-ylmethyl, 4-fluororphenyl, or 3-oxetanyl.

E11: The compound according to any one of E1-E10, wherein R³ and R³' are both hydrogen.

E11.1: The compound according to any of E1-E10 wherein R³ and R³' are both deuterium.

E12: The compound according to any one of E1-E10, wherein one of R³ or R³' is hydrogen and the other is methyl, tert-butyl, cyclopropyl, —CH₂OH or —CH₂OCH₃.

E13: The compound according to any one of E1-E10, wherein one of R³ or R³' is hydrogen, deuterium, or methyl, and the other is hydrogen, methyl, isopropyl, cyclopropyl, hydroxymethyl, methoxymethyl, or deuterium; or R³ and R³' taken together with the carbon to which they are attached form a 3-membered cycloalkyl.

E14: The compound according to any one of E1-E13, wherein R⁴ is hydrogen.

E15: The compound according to any one of E1-E13, wherein R⁴ is methyl.

E16: The compound according to any one of E1 and E5-E15 wherein:

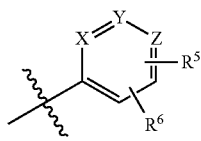

is selected from:

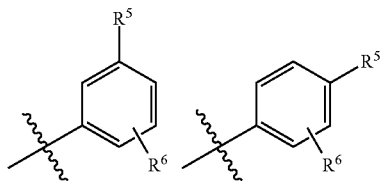

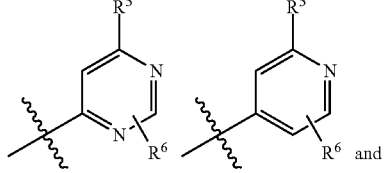

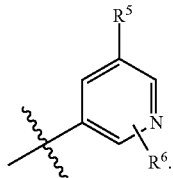

E17: The compound according to any one of E1-E16, wherein R⁵ is trifluoromethyl-phenyl.

E18: The compound according to any one of E1-E16, wherein R⁵ is 4-trifluoromethyl-pyridinyl, trifluoromethyl-pyridazinyl, trifluoromethyl-pyrimidinyl or trifluoromethyl-pyrazinyl.

E19: The compound according to any one of E1-E16, wherein R⁵ is trifluoromethylphenyl, 5-trifluoromethyl-pyrid-2-yl, 6-trifluoromethylpyrid-3-yl, 6-trifluoromethyl-pyridazin-3-yl, 2-trifluoromethylpyrimidin-5-yl, 5-trifluoromethylpyrazin-2-yl, pyrrolidino, cyclopropyl, 4,4-difluoropiperidino, 4-trifluoromethylpiperidino, 2-(2-methylpyrrolidino)pyrimidin-5-yl, or 4-trifluoromethylcyclohex-1-ene.

E20: The compound according to any one of E1-E16, wherein R⁵ is trifluoromethyl-phenyl, trifluoromethyl-pyridinyl, trifluoromethyl-pyridazinyl, trifluoromethyl-pyrimidinyl, azetidino, pyrrolidino, piperidino, pyrrolidino-pyrimidinyl, or trifluoromethyl-pyrazinyl, wherein any azetidinyl, pyrrolidino, cycloalkyl, heterocycle, and piperidino is optionally substituted with lower alkyl, halogen, or trifluoromethyl.

E21: The compound according to any one of E1-E20, wherein R⁶ is hydrogen.

E22: The compound according to any one of E1-E20, wherein R⁶ is F or methoxy.

E23: The compound according to any one of E1-E20, wherein R⁶ is halogen or alkoxy.

E23: The compound according to any one of E1 and E5-E15, wherein:

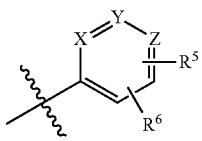

is selected from:

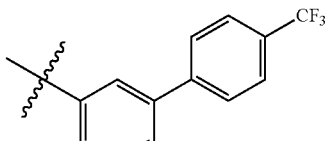

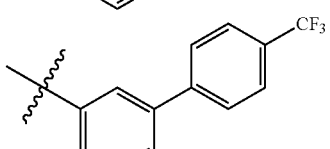

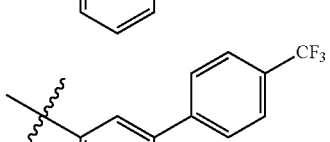

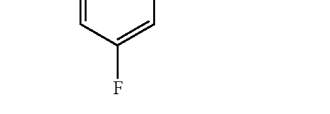

-continued
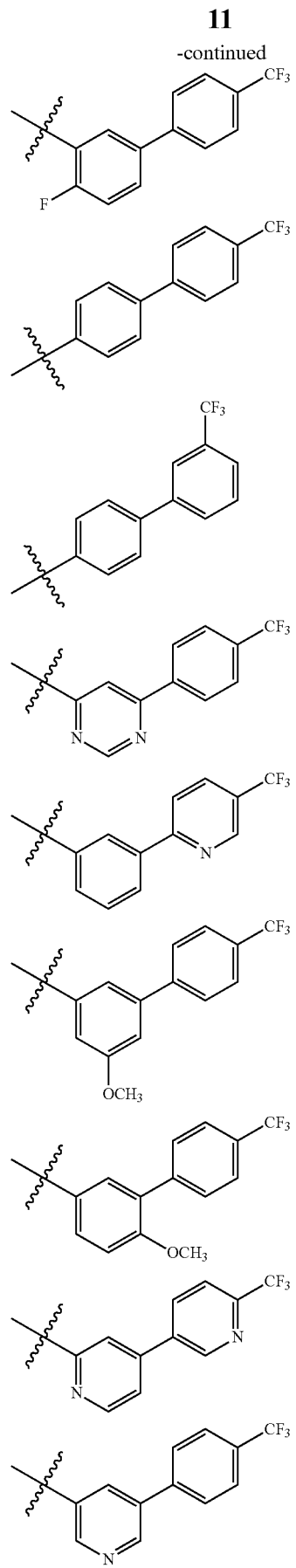
-continued
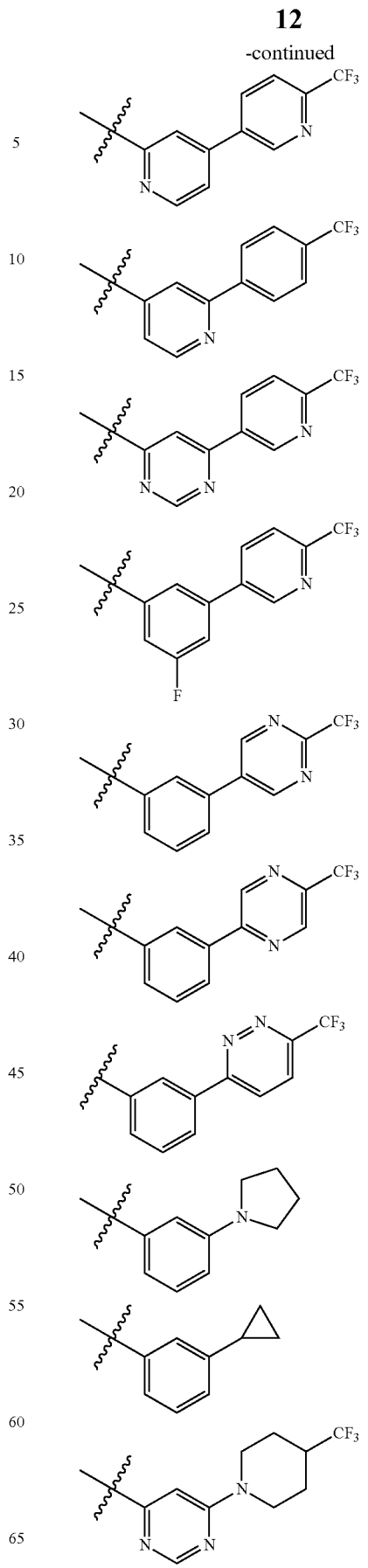

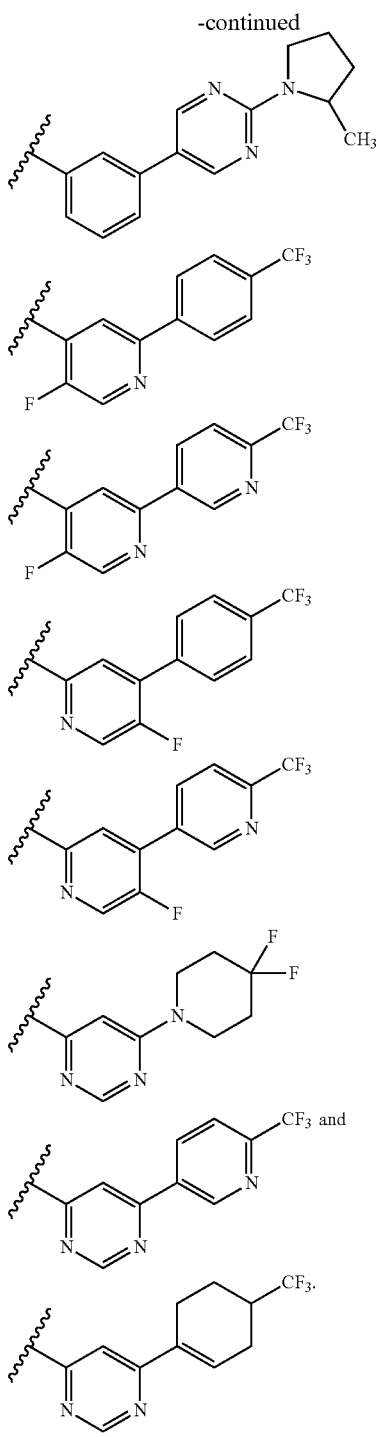

E24: The compound according to E1, wherein said compound is:

2-[(4-Fluoro-benzenesulfonyl)-methyl-amino]-N-(4'-trifluoromethyl-biphenyl-3-ylmethyl)-acetamide;
(S)-2-[(4-Fluoro-benzenesulfonyl)-methyl-amino]-N-(4'-trifluoromethyl-biphenyl-3-ylmethyl)-propionamide;
2-(4-Fluoro-benzenesulfonylamino)-N-(4'-trifluoromethyl-biphenyl-3-ylmethyl)-acetamide;
(R)-2-[(4-Fluoro-benzenesulfonyl)-methyl-amino]-N-(4'-trifluoromethyl-biphenyl-3-ylmethyl)-propionamide;
(S)-2-[(4-Fluoro-benzenesulfonyl)-methyl-amino]-3-methyl-N-(4'-trifluoromethyl-biphenyl-3-ylmethyl)-butyramide;
(R)-2-[(4-Fluoro-benzenesulfonyl)-methyl-amino]-3-methyl-N-(4'-trifluoromethyl-biphenyl-3-ylmethyl)-butyramide;
2-[(4-Fluoro-benzenesulfonyl)-methyl-amino]-2-methyl-N-(4'-trifluoromethyl-biphenyl-3-ylmethyl)-propionamide;
2-[(4-Fluoro-benzenesulfonyl)-methyl-amino]-N-(6-fluoro-4'-trifluoromethyl-biphenyl-3-ylmethyl)-acetamide;
2-[(4-Fluoro-benzenesulfonyl)-methyl-amino]-N-(2-fluoro-4'-trifluoromethyl-biphenyl-3-ylmethyl)-acetamide;
2-[(4-Fluoro-benzenesulfonyl)-methyl-amino]-N-(4'-trifluoromethyl-biphenyl-4-ylmethyl)-acetamide;
2-[(4-Fluoro-benzenesulfonyl)-methyl-amino]-N-(5-fluoro-4'-trifluoromethyl-biphenyl-3-ylmethyl)-acetamide;
2-[(4-Fluoro-benzenesulfonyl)-methyl-amino]-N-(4-fluoro-4'-trifluoromethyl-biphenyl-3-ylmethyl)-acetamide;
2-[(4-fluoro-benzenesulfonyl)-(2,2,2-trifluoro-ethyl)-amino]-N-(4'-trifluoromethyl-biphenyl-3-ylmethyl)-acetamide;
2-[Ethyl-(4-fluoro-benzenesulfonyl)-amino]-N-(6-fluoro-4'-trifluoromethyl-biphenyl-3-ylmethyl)-acetamide;
2-[Ethyl-(4-fluoro-benzenesulfonyl)-amino]-N-(5-fluoro-4'-trifluoromethyl-biphenyl-3-ylmethyl)-acetamide;
2-[Ethyl-(4-fluoro-benzenesulfonyl)-amino]-N-(4-fluoro-4'-trifluoromethyl-biphenyl-3-ylmethyl)-acetamide;
2-[Ethyl-(4-fluoro-benzenesulfonyl)-amino]-N-(4'-trifluoromethyl-biphenyl-4-ylmethyl)-acetamide;
2-[Ethyl-(4-fluoro-benzenesulfonyl)-amino]-N-(3'-trifluoromethyl-biphenyl-4-ylmethyl)-acetamide;
2-[(4-Fluoro-benzenesulfonyl)-(2-hydroxy-ethyl)-amino]-N-(4'-trifluoromethyl-biphenyl-3-ylmethyl)-acetamide;
2-[(4-Fluoro-benzenesulfonyl)-(2-hydroxy-propyl)-amino]-N-(4'-trifluoromethyl-biphenyl-3-ylmethyl)-acetamide;
2-[(4-Fluoro-benzenesulfonyl)-methyl-amino]-N-[6-(4-trifluoromethyl-phenyl)-pyrimidin-4-ylmethyl]-acetamide;
2-[Cyclopropyl-(4-fluoro-benzenesulfonyl)-amino]-N-(4'-trifluoromethyl-biphenyl-3-ylmethyl)-acetamide;
2-[Ethyl-(4-fluoro-benzenesulfonyl)-amino]-N-(4'-trifluoromethyl-biphenyl-3-ylmethyl)-acetamide;
2-cyclopropyl-2-(4-fluoro-benzenesulfonylamino)-N-(4'-trifluoromethyl-biphenyl-3-ylmethyl)-acetamide;
2-[(5-chloro-thiophene-2-sulfonyl)-methyl-amino]-N-[6-(4-trifluoromethyl-phenyl)-pyrimidin-4-ylmethyl]-acetamide;
2-[methyl-(thiophene-2-sulfonyl)-amino]-N-[6-(4-trifluoromethyl-phenyl)-pyrimidin-4-ylmethyl]-acetamide;
2-[(4-Fluoro-benzenesulfonyl)-isopropyl-amino]-N-[6-(4-trifluoromethyl-phenyl)-pyrimidin-4-ylmethyl]-acetamide;
2-[Ethyl-(4-fluoro-benzenesulfonyl)-amino]-N-[6-(4-trifluoromethyl-phenyl)-pyrimidin-4-ylmethyl]-acetamide;
2-[(4-Fluoro-benzenesulfonyl)-(2-methoxy-ethyl)-amino]-N-[6-(4-trifluoromethyl-phenyl)-pyrimidin-4-ylmethyl]-acetamide;
2-[(4-fluoro-benzenesulfonyl)-(2-hydroxy-ethyl)-amino]-N-[6-(4-trifluoromethyl-phenyl)-pyrimidin-4-ylmethyl]-acetamide;
2-[tert-Butyl-(4-fluoro-benzenesulfonyl)-amino]-N-[6-(4-trifluoromethyl-phenyl)-pyrimidin-4-ylmethyl]-acetamide;
(S)-2-[(4-Fluoro-benzenesulfonyl)-isopropyl-amino]-N-[6-(4-trifluoromethyl-phenyl)-pyrimidin-4-ylmethyl]-propionamide;
2-[(4-Fluoro-benzenesulfonyl)-isopropyl-amino]-N-(4'-trifluoromethyl-biphenyl-4-ylmethyl)-acetamide;

2-[(4-Fluoro-benzenesulfonyl)-isopropyl-amino]-N-(3'-trifluoromethyl-biphenyl-4-ylmethyl)-acetamide;
2-[(4-Fluoro-benzenesulfonyl)-isopropyl-amino]-N-(6-fluoro-4'-trifluoromethyl-biphenyl-3-ylmethyl)-acetamide;
2-[(4-Fluoro-benzenesulfonyl)-isopropyl-amino]-N-(5-fluoro-4'-trifluoromethyl-biphenyl-3-ylmethyl)-acetamide;
2-[(4-Fluoro-benzenesulfonyl)-isopropyl-amino]-N-(4-fluoro-4'-trifluoromethyl-biphenyl-3-ylmethyl)-acetamide;
(R)-2-[(4-Fluoro-benzenesulfonyl)-methyl-amino]-N-[6-(4-trifluoromethyl-phenyl)-pyrimidin-4-ylmethyl]-propionamide;
2-[(4-Fluoro-benzenesulfonyl)-isopropyl-amino]-N-(4'-trifluoromethyl-biphenyl-3-ylmethyl)-acetamide;
2-[(4-Fluoro-benzenesulfonyl)-isopropyl-amino]-N-[3-(5-trifluoromethyl-pyridin-2-yl)-benzyl]-acetamide;
2-[(4-Fluoro-benzenesulfonyl)-methyl-amino]-N-[3-(5-trifluoromethyl-pyridin-2-yl)-benzyl]-acetamide;
2-[Ethyl-(4-fluoro-benzenesulfonyl)-amino]-N-[3-(5-trifluoromethyl-pyridin-2-yl)-benzyl]-acetamide;
2-[(4-Fluoro-benzenesulfonyl)-methyl-amino]-N-(5-methoxy-4'-trifluoromethyl-biphenyl-3-ylmethyl)-acetamide;
2-[Ethyl-(4-fluoro-benzenesulfonyl)-amino]-N-(5-methoxy-4'-trifluoromethyl-biphenyl-3-ylmethyl)-acetamide;
2-[(4-Fluoro-benzenesulfonyl)-isopropyl-amino]-N-(5-methoxy-4'-trifluoromethyl-biphenyl-3-ylmethyl)-acetamide;
2-[Ethyl-(4-fluoro-benzenesulfonyl)-amino]-N-(6-methoxy-4'-trifluoromethyl-biphenyl-3-ylmethyl)-acetamide;
2-[(4-Fluoro-benzenesulfonyl)-isopropyl-amino]-N-(6-methoxy-4'-trifluoromethyl-biphenyl-3-ylmethyl)-acetamide;
2-[(3-Fluoro-benzenesulfonyl)-isopropyl-amino]-N-(4'-trifluoromethyl-biphenyl-3-ylmethyl)-acetamide;
2-[(3-Fluoro-benzenesulfonyl)-isopropyl-amino]-N-[6-(4-trifluoromethyl-phenyl)-pyrimidin-4-ylmethyl]-acetamide;
2-[(3-Fluoro-benzenesulfonyl)-isopropyl-amino]-N-[3-(5-trifluoromethyl-pyridin-2-yl)-benzyl]-acetamide;
2-[(4-Fluoro-benzenesulfonyl)-methyl-amino]-3-hydroxy-N-(4'-trifluoromethyl-biphenyl-3-ylmethyl)-propionamide;
(S)-2-[(4-Fluoro-benzenesulfonyl)-methyl-amino]-3-methoxy-N-(4'-trifluoromethyl-biphenyl-3-ylmethyl)-propionamide;
2-(Benzenesulfonyl-isopropyl-amino)-N-(4'-trifluoromethyl-biphenyl-3-ylmethyl)-acetamide;
2-[(4-Fluoro-benzenesulfonyl)-oxetan-3-ylmethyl-amino]-N-(4'-trifluoron-3-ylmethyl-amino]-N-(4'-trifluoro methyl-biphenyl-3-ylmethyl)-acetamide;
2-[(4-Fluoro-benzenesulfonyl)-isopropyl-amino]-N-(6-trifluoromethyl-[3,4']bipyridinyl-2'-ylmethyl)-acetamide;
2-[Isopropyl-(pyridine-3-sulfonyl)-amino]-N-[6-(4-trifluoromethyl-phenyl)-pyrimidin-4-ylmethyl]-acetamide;
2-[(4-Fluoro-benzenesulfonyl)-isopropyl-amino]-N-[5-(4-trifluoromethyl-phenyl)-pyridin-3-ylmethyl]-acetamide;
2-[(4-Fluoro-benzenesulfonyl)-isopropyl-amino]-N-(6'-trifluoromethyl-[2,3]bipyridinyl-4-ylmethyl)-acetamide;
2-[(3-Fluoro-benzenesulfonyl)-isopropyl-amino]-N-[2-(4-trifluoromethyl-phenyl)-pyrimidin-4-ylmethyl]-acetamide;
2-[(4-Fluoro-benzenesulfonyl)-oxetan-3-yl-amino]-N-(4'-trifluoromethyl-biphenyl-3-ylmethyl)-acetamide;
2-[(4-Fluoro-benzenesulfonyl)-isopropyl-amino]-N-[6-(6-trifluoromethyl-pyridin-3-yl)-pyrimidin-4-ylmethyl]-acetamide;
2-[(4-Fluoro-benzenesulfonyl)-(2,2,2-trifluoro-ethyl)-amino]-N-(4'-trifluoromethyl-biphenyl-3-ylmethyl)-acetamide;
2-[(4-Fluoro-benzenesulfonyl)-isopropyl-amino]-N-[3-fluoro-5-(6-trifluoromethyl-pyridin-3-yl)-benzyl]-acetamide;
2-[(6-Chloro-pyridine-3-sulfonyl)-isopropyl-amino]-N-[6-(4-trifluoromethyl-phenyl)-pyrimidin-4-ylmethyl]-acetamide;
2-[(2-Cyano-benzenesulfonyl)-isopropyl-amino]-N-[6-(4-trifluoromethyl-phenyl)-pyrimidin-4-ylmethyl]-acetamide;
2-[(4-Fluoro-benzenesulfonyl)-isopropyl-amino]-N-[3-(6-trifluoromethyl-pyridazin-3-yl)-benzyl]-acetamide;
2-[Isopropyl-(pyrazine-2-sulfonyl)-amino]-N-[6-(4-trifluoromethyl-phenyl)-pyrimidin-4-ylmethyl]-acetamide;
2-[(4-Fluoro-benzenesulfonyl)-isopropyl-amino]-N-[3-(2-trifluoromethyl-pyrimidin-5-yl)-benzyl]-acetamide;
2-[(3,4-Difluoro-benzenesulfonyl)-isopropyl-amino]-N-[6-(4-trifluoromethyl-phenyl)-pyrimidin-4-ylmethyl]-acetamide;
2-[(4-Fluoro-benzenesulfonyl)-isopropyl-amino]-N-[4-fluoro-3-(2-trifluoromethyl-pyrimidin-5-yl)-benzyl]-acetamide; or
2-[(4-Fluoro-benzenesulfonyl)-isopropyl-amino]-N-[3-(5-trifluoromethyl-pyrazin-2-yl)-benzyl]-acetamide;
2-[(6-Chloro-pyridine-3-sulfonyl)-isopropyl-amino]-N-[3-(5-trifluoromethyl-pyrazin-2-yl)-benzyl]-acetamide;
2-[(6-Chloro-pyridine-3-sulfonyl)-isopropyl-amino]-N-[3-(6-trifluoromethyl-pyridazin-3-yl)-benzyl]-acetamide;
2-[(4-Fluoro-benzenesulfonyl)-isopropyl-amino]-N-[2-(2-trifluoromethyl-pyrimidin-5-yl)-pyridin-4-ylmethyl]-acetamide;
2-[(5-Chloro-thiophene-2-sulfonyl)-isopropyl-amino]-N-[6-(4-trifluoromethyl-phenyl)-pyrimidin-4-ylmethyl]-acetamide;
2-[(5-Chloro-thiophene-2-sulfonyl)-isopropyl-amino]-N-[6-(6-trifluoromethyl-pyridin-3-yl)-pyrimidin-4-ylmethyl]-acetamide; or
2-(4-fluoro-N-(4-fluorophenyl)phenylsulfonamido)-N-((6-(6-(trifluoromethyl)pyridin-3-yl)pyrimidin-4-yl)methyl)acetamide.

E25: In another embodiment, the invention provides for a compound according to E1, wherein said compound is:
2-(4-fluoro-N-isopropylphenylsulfonamido)-N-(3-(pyrrolidin-1-yl)benzyl)acetamide;
N-(3-cyclopropylbenzyl)-2-(4-fluoro-N-isopropylphenylsulfonamido)acetamide;
R)-2-(4-fluoro-N-isopropylphenylsulfonamido)-N-(3-(2-(2-methylpyrrolidin-1-yl)pyrimidin-5-yl)benzyl)acetamide;
(S)-2-(4-fluoro-N-isopropylphenylsulfonamido)-N-(3-(2-(2-methylpyrrolidin-1-yl)pyrimidin-5-yl)benzyl)acetamide;
2-(4-Fluoro-N-isopropylphenylsulfonamido)-N-((6-(4-(trifluoromethyl)piperidin-1-yl)pyrimidin-4-yl)methyl)acetamide;
N-((6-(4,4-Difluoropiperidin-1-yl)pyrimidin-4-yl)methyl)-2-(4-fluoro-N-isopropylphenylsulfonamido)acetamide;
2-(N-Isopropyl-1-methyl-1H-pyrazole-3-sulfonamido)-N-((4'-(trifluoromethyl)biphenyl-3-yl)methyl)acetamide;
2,2-Dideuterio-2-(4-fluoro-N-isopropylphenylsulfonamido)-N-((6-(6-(trifluoromethyl)pyridin-3-yl)pyrimidin-4-yl)methyl)acetamide;

1-(4-Fluoro-N-isopropylphenylsulfonamido)-N-((6-(6-(trifluoromethyl)pyridin-3-yl)pyrimidin-4-yl)methyl)cyclopropanecarboxamide;
(6-(6-(Trifluoromethyl)pyridin-3-yl)pyrimidin-4-yl)methyl-2-(4-fluoro-N-isopropylphenylsulfonamido)acetate; or
2-[N-(Propan-2-yl)(4-fluorobenzene)sulfonamido]-N-([6-[4-(trifluoromethyl)cyclohex-1-en-1-yl]pyrimidin-4-yl]methyl)acetamide;
or a salt thereof.

In one embodiment the invention provides a compound of formula (I) which is a compound of formula (Ia):

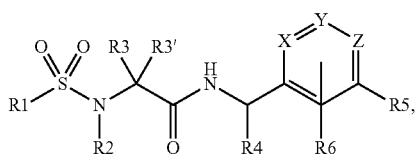

wherein:
a) X, Y, Z are, independently of each other, C or N;
b) R1 is unsubstituted phenyl, phenyl mono- or bi-substituted independently with halogen or —CN, an unsubstituted five- or six-membered heteroaryl ring or a five- or six-membered heteroaryl ring substituted with halogen;
c) R2 is hydrogen, unsubstituted lower alkyl, haloalkyl, lower alkyl substituted with —OH or oxytanyl, cycloalkyl, alkoxy or oxytanyl;
d) R3, R3' are, independently of each other, hydrogen, unsubstituted lower alkyl, cycloalkyl or lower alkyl substituted with alkoxy;
e) R4 is hydrogen or lower alkyl;
f) R5 is trifluoromethyl-phenyl, trifluoromethyl-pyridinyl, trifluoromethyl-pyridazinyl, trifluoromethyl-pyrimidinyl or trifluoromethyl-pyrazinyl; and
g) R6 is hydrogen, halogen or alkoxy,
h) or a pharmaceutically acceptable salt thereof.

In another embodiment, the invention provides for a compound according to formula (Ia), wherein X, Y and Z are C.

In another embodiment, the invention provides for a compound according to formula (Ia), wherein one of X, Y or Z is N and the others are C.

In another embodiment, the invention provides for a compound according to formula (Ia), wherein two of X, Y or Z is N and the other is C.

In another embodiment, the invention provides for a compound according to formula (Ia), wherein R1 is unsubstituted phenyl, pyrazinyl, pyridinyl or thienyl.

In another embodiment, the invention provides for a compound according to formula (Ia), wherein R1 is phenyl substituted with F or Cl, pyrazinyl substituted with F or Cl, pyridinyl substituted with F or Cl, or thienyl substituted with F or Cl.

In another embodiment, the invention provides for a compound according to formula (Ia), wherein R2 is hydrogen.

In another embodiment, the invention provides for a compound according to formula (Ia), wherein R2 is methyl, —CH₂CF₃, ethyl, hydroxy-ethyl, propyl, hydroxy-propyl, cyclopropyl, isopropyl, methoxy-ethyl, tert-butyl, oxetan-3-ylmethyl or oxetanyl.

In another embodiment, the invention provides for a compound according to formula (Ia), wherein R3 and R3' are both hydrogen.

In another embodiment, the invention provides for a compound according to formula (Ia), wherein one of R3 or R3' is hydrogen and the other is methyl, tert-butyl, cyclopropyl, —CH₂OH or CH₂OCH₃.

In another embodiment, the invention provides for a compound according to formula (Ia), wherein R4 is hydrogen.

In another embodiment, the invention provides for a compound according to formula (Ia), wherein R4 is methyl.

In another embodiment, the invention provides for a compound according to formula (Ia), wherein R5 is trifluoromethyl-phenyl.

In another embodiment, the invention provides for a compound according to formula (Ia), wherein R5 is trifluoromethyl-pyridinyl, trifluoromethyl-pyridazinyl, trifluoromethyl-pyrimidinyl or trifluoromethyl-pyrazinyl.

In another embodiment, the invention provides for a compound according to formula (Ia), wherein R6 is hydrogen.

In another embodiment, the invention provides for a compound according to formula (Ia), wherein R6 is F or methoxy.

In another embodiment, the invention provides the compound:
2-[(4-Fluoro-benzenesulfonyl)-methyl-amino]-N-(4'-trifluoromethyl-biphenyl-3-ylmethyl)-acetamide;
(S)-2-[(4-Fluoro-benzenesulfonyl)-methyl-amino]-N-(4'-trifluoromethyl-biphenyl-3-ylmethyl)-propionamide;
2-(4-Fluoro-benzenesulfonylamino)-N-(4'-trifluoromethyl-biphenyl-3-ylmethyl)-acetamide;
(R)-2-[(4-Fluoro-benzenesulfonyl)-methyl-amino]-N-(4'-trifluoromethyl-biphenyl-3-ylmethyl)-propionamide;
(S)-2-[(4-Fluoro-benzenesulfonyl)-methyl-amino]-3-methyl-N-(4'-trifluoromethyl-biphenyl-3-ylmethyl)-butyramide;
(R)-2-[(4-Fluoro-benzenesulfonyl)-methyl-amino]-3-methyl-N-(4'-trifluoromethyl-biphenyl-3-ylmethyl)-butyramide;
2-[(4-Fluoro-benzenesulfonyl)-methyl-amino]-2-methyl-N-(4'-trifluoromethyl-biphenyl-3-ylmethyl)-propionamide;
2-[(4-Fluoro-benzenesulfonyl)-methyl-amino]-N-(6-fluoro-4'-trifluoromethyl-biphenyl-3-ylmethyl)-acetamide;
2-[(4-Fluoro-benzenesulfonyl)-methyl-amino]-N-(2-fluoro-4'-trifluoromethyl-biphenyl-3-ylmethyl)-acetamide;
2-[(4-Fluoro-benzenesulfonyl)-methyl-amino]-N-(4'-trifluoromethyl-biphenyl-4-ylmethyl)-acetamide;
2-[(4-Fluoro-benzenesulfonyl)-methyl-amino]-N-(5-fluoro-4'-trifluoromethyl-biphenyl-3-ylmethyl)-acetamide;
2-[(4-Fluoro-benzenesulfonyl)-methyl-amino]-N-(4-fluoro-4'-trifluoromethyl-biphenyl-3-ylmethyl)-acetamide;
2-[(4-fluoro-benzenesulfonyl)-(2,2,2-trifluoro-ethyl)-amino]-N-(4'-trifluoromethyl-biphenyl-3-ylmethyl)-acetamide;
2-[Ethyl-(4-fluoro-benzenesulfonyl)-amino]-N-(6-fluoro-4'-trifluoromethyl-biphenyl-3-ylmethyl)-acetamide;
2-[Ethyl-(4-fluoro-benzenesulfonyl)-amino]-N-(5-fluoro-4'-trifluoromethyl-biphenyl-3-ylmethyl)-acetamide;
2-[Ethyl-(4-fluoro-benzenesulfonyl)-amino]-N-(4-fluoro-4'-trifluoromethyl-biphenyl-3-ylmethyl)-acetamide;
2-[Ethyl-(4-fluoro-benzenesulfonyl)-amino]-N-(4'-trifluoromethyl-biphenyl-4-ylmethyl)-acetamide;
2-[Ethyl-(4-fluoro-benzenesulfonyl)-amino]-N-(3'-trifluoromethyl-biphenyl-4-ylmethyl)-acetamide;

2-[(4-Fluoro-benzenesulfonyl)-(2-hydroxy-ethyl)-amino]-N-(4'-trifluoromethyl-biphenyl-3-ylmethyl)-acetamide;

2-[(4-Fluoro-benzenesulfonyl)-(2-hydroxy-propyl)-amino]-N-(4'-trifluoromethyl-biphenyl-3-ylmethyl)-acetamide;

2-[(4-Fluoro-benzenesulfonyl)-methyl-amino]-N-[6-(4-trifluoromethyl-phenyl)-pyrimidin-4-ylmethyl]-acetamide;

2-[Cyclopropyl-(4-fluoro-benzenesulfonyl)-amino]-N-(4'-trifluoromethyl-biphenyl-3-ylmethyl)-acetamide;

2-[Ethyl-(4-fluoro-benzenesulfonyl)-amino]-N-(4'-trifluoromethyl-biphenyl-3-ylmethyl)-acetamide;

2-cyclopropyl-2-(4-fluoro-benzenesulfonylamino)-N-(4'-trifluoromethyl-biphenyl-3-ylmethyl)-acetamide;

2-[(5-chloro-thiophene-2-sulfonyl)-methyl-amino]-N-[6-(4-trifluoromethyl-phenyl)-pyrimidin-4-ylmethyl]-acetamide;

2-[methyl-(thiophene-2-sulfonyl)-amino]-N-[6-(4-trifluoromethyl-phenyl)-pyrimidin-4-ylmethyl]-acetamide;

2-[(4-Fluoro-benzenesulfonyl)-isopropyl-amino]-N-[6-(4-trifluoromethyl-phenyl)-pyrimidin-4-ylmethyl]-acetamide;

2-[Ethyl-(4-fluoro-benzenesulfonyl)-amino]-N-[6-(4-trifluoromethyl-phenyl)-pyrimidin-4-ylmethyl]-acetamide;

2-[(4-Fluoro-benzenesulfonyl)-(2-methoxy-ethyl)-amino]-N-[6-(4-trifluoromethyl-phenyl)-pyrimidin-4-ylmethyl]-acetamide;

2-[(4-fluoro-benzenesulfonyl)-(2-hydroxy-ethyl)-amino]-N-[6-(4-trifluoromethyl-phenyl)-pyrimidin-4-ylmethyl]-acetamide;

2-[tert-Butyl-(4-fluoro-benzenesulfonyl)-amino]-N-[6-(4-trifluoromethyl-phenyl)-pyrimidin-4-ylmethyl]-acetamide;

(S)-2-[(4-Fluoro-benzenesulfonyl)-isopropyl-amino]-N-[6-(4-trifluoromethyl-phenyl)-pyrimidin-4-ylmethyl]-propionamide;

2-[(4-Fluoro-benzenesulfonyl)-isopropyl-amino]-N-(4'-trifluoromethyl-biphenyl-4-ylmethyl)-acetamide;

2-[(4-Fluoro-benzenesulfonyl)-isopropyl-amino]-N-(3'-trifluoromethyl-biphenyl-4-ylmethyl)-acetamide;

2-[(4-Fluoro-benzenesulfonyl)-isopropyl-amino]-N-(6-fluoro-4'-trifluoromethyl-biphenyl-3-ylmethyl)-acetamide;

2-[(4-Fluoro-benzenesulfonyl)-isopropyl-amino]-N-(5-fluoro-4'-trifluoromethyl-biphenyl-3-ylmethyl)-acetamide;

2-[(4-Fluoro-benzenesulfonyl)-isopropyl-amino]-N-(4-fluoro-4'-trifluoromethyl-biphenyl-3-ylmethyl)-acetamide;

(R)-2-[(4-Fluoro-benzenesulfonyl)-methyl-amino]-N-[6-(4-trifluoromethyl-phenyl)-pyrimidin-4-ylmethyl]-propionamide;

2-[(4-Fluoro-benzenesulfonyl)-isopropyl-amino]-N-(4'-trifluoromethyl-biphenyl-3-ylmethyl)-acetamide;

2-[(4-Fluoro-benzenesulfonyl)-isopropyl-amino]-N-[3-(5-trifluoromethyl-pyridin-2-yl)-benzyl]-acetamide;

2-[(4-Fluoro-benzenesulfonyl)-methyl-amino]-N-[3-(5-trifluoromethyl-pyridin-2-yl)-benzyl]-acetamide;

2-[Ethyl-(4-fluoro-benzenesulfonyl)-amino]-N-[3-(5-trifluoromethyl-pyridin-2-yl)-benzyl]-acetamide;

2-[(4-Fluoro-benzenesulfonyl)-methyl-amino]-N-(5-methoxy-4'-trifluoromethyl-biphenyl-3-ylmethyl)-acetamide;

2-[Ethyl-(4-fluoro-benzenesulfonyl)-amino]-N-(5-methoxy-4'-trifluoromethyl-biphenyl-3-ylmethyl)-acetamide;

2-[(4-Fluoro-benzenesulfonyl)-isopropyl-amino]-N-(5-methoxy-4'-trifluoromethyl-biphenyl-3-ylmethyl)-acetamide;

2-[Ethyl-(4-fluoro-benzenesulfonyl)-amino]-N-(6-methoxy-4'-trifluoromethyl-biphenyl-3-ylmethyl)-acetamide;

2-[(4-Fluoro-benzenesulfonyl)-isopropyl-amino]-N-(6-methoxy-4'-trifluoromethyl-biphenyl-3-ylmethyl)-acetamide;

2-[(3-Fluoro-benzenesulfonyl)-isopropyl-amino]-N-(4'-trifluoromethyl-biphenyl-3-ylmethyl)-acetamide;

2-[(3-Fluoro-benzenesulfonyl)-isopropyl-amino]-N-[6-(4-trifluoromethyl-phenyl)-pyrimidin-4-ylmethyl]-acetamide;

2-[(3-Fluoro-benzenesulfonyl)-isopropyl-amino]-N-[3-(5-trifluoromethyl-pyridin-2-yl)-benzyl]-acetamide;

2-[(4-Fluoro-benzenesulfonyl)-methyl-amino]-3-hydroxy-N-(4'-trifluoromethyl-biphenyl-3-ylmethyl)-propionamide;

(S)-2-[(4-Fluoro-benzenesulfonyl)-methyl-amino]-3-methoxy-N-(4'-trifluoromethyl-biphenyl-3-ylmethyl)-propionamide;

2-(Benzenesulfonyl-isopropyl-amino)-N-(4'-trifluoromethyl-biphenyl-3-ylmethyl)-acetamide;

2-[(4-Fluoro-benzenesulfonyl)-oxetan-3-ylmethyl-amino]-N-(4'-trifluoron-3-ylmethyl-amino]-N-(4'-trifluoro methyl-biphenyl-3-ylmethyl)-acetamide;

2-[(4-Fluoro-benzenesulfonyl)-isopropyl-amino]-N-(6-trifluoromethyl-[3,4']bipyridinyl-2'-ylmethyl)-acetamide;

2-[Isopropyl-(pyridine-3-sulfonyl)-amino]-N-[6-(4-trifluoromethyl-phenyl)-pyrimidin-4-ylmethyl]-acetamide;

2-[(4-Fluoro-benzenesulfonyl)-isopropyl-amino]-N-[5-(4-trifluoromethyl-phenyl)-pyridin-3-ylmethyl]-acetamide;

2-[(4-Fluoro-benzenesulfonyl)-isopropyl-amino]-N-(6'-trifluoromethyl-[2,3]bipyridinyl-4-ylmethyl)-acetamide;

2-[(3-Fluoro-benzenesulfonyl)-isopropyl-amino]-N-[2-(4-trifluoromethyl-phenyl)-pyridin-4-ylmethyl]-acetamide;

2-[(4-Fluoro-benzenesulfonyl)-oxetan-3-yl-amino]-N-(4'-trifluoromethyl-biphenyl-3-ylmethyl)-acetamide;

2-[(4-Fluoro-benzenesulfonyl)-isopropyl-amino]-N-[6-(6-trifluoromethyl-pyridin-3-yl)-pyrimidin-4-ylmethyl]-acetamide;

2-[(4-Fluoro-benzenesulfonyl)-(2,2,2-trifluoro-ethyl)-amino]-N-(4'-trifluoromethyl-biphenyl-3-ylmethyl)-acetamide;

2-[(4-Fluoro-benzenesulfonyl)-isopropyl-amino]-N-[3-fluoro-5-(6-trifluoromethyl-pyridin-3-yl)-benzyl]-acetamide;

2-[(6-Chloro-pyridine-3-sulfonyl)-isopropyl-amino]-N-[6-(4-trifluoromethyl-phenyl)-pyrimidin-4-ylmethyl]-acetamide;

2-[(2-Cyano-benzenesulfonyl)-isopropyl-amino]-N-[6-(4-trifluoromethyl-phenyl)-pyrimidin-4-ylmethyl]-acetamide;

2-[(4-Fluoro-benzenesulfonyl)-isopropyl-amino]-N-[3-(6-trifluoromethyl-pyridazin-3-yl)-benzyl]-acetamide;

2-[Isopropyl-(pyrazine-2-sulfonyl)-amino]-N-[6-(4-trifluoromethyl-phenyl)-pyrimidin-4-ylmethyl]-acetamide;

2-[(4-Fluoro-benzenesulfonyl)-isopropyl-amino]-N-[3-(2-trifluoromethyl-pyrimidin-5-yl)-benzyl]-acetamide;

2-[(3,4-Difluoro-benzenesulfonyl)-isopropyl-amino]-N-[6-(4-trifluoromethyl-phenyl)-pyrimidin-4-ylmethyl]-acetamide;

2-[(4-Fluoro-benzenesulfonyl)-isopropyl-amino]-N-[4-fluoro-3-(2-trifluoromethyl-pyrimidin-5-yl)-benzyl]-acetamide;

2-[(4-Fluoro-benzenesulfonyl)-isopropyl-amino]-N-[3-(5-trifluoromethyl-pyrazin-2-yl)-benzyl]-acetamide;

2-[(6-Chloro-pyridine-3-sulfonyl)-isopropyl-amino]-N-[3-(5-trifluoromethyl-pyrazin-2-yl)-benzyl]-acetamide;

2-[(6-Chloro-pyridine-3-sulfonyl)-isopropyl-amino]-N-[3-(6-trifluoromethyl-pyridazin-3-yl)-benzyl]-acetamide;

2-[(4-Fluoro-benzenesulfonyl)-isopropyl-amino]-N-[2-(2-trifluoromethyl-pyrimidin-5-yl)-pyridin-4-ylmethyl]-acetamide;

2-[(5-Chloro-thiophene-2-sulfonyl)-isopropyl-amino]-N-[6-(4-trifluoromethyl-phenyl)-pyrimidin-4-ylmethyl]-acetamide; or 2-[(5-Chloro-thiophene-2-sulfonyl)-isopropyl-amino]-N-[6-(6-trifluoromethyl-pyridin-3-yl)-pyrimidin-4-ylmethyl]-acetamide;

or a salt thereof.

In another embodiment of the invention, the compounds of formula (I) are isotopically-labeled by having one or more atoms therein replaced by an atom having a different atomic mass or mass number. Such isotopically-labeled (i.e., radio-labelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ionchannels, particularly TRPA1. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements. As illustrated in Example 83, the compounds of the invention include compounds of Formula (I) wherein $R^3$ and/or $R^{3'}$ are enriched in deuterium above the normal natural abundance. For example, the $R^3$ and/or $R^{3'}$ can each be independently enriched with 1, 2, 5, 10, 25, 50, 75, 90, 95, or 99 percent deuterium.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula (I) and a pharmaceutically acceptable carrier.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6}alkyl))_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or and embodiment thereof and at least one pharmaceutically acceptable carrier, diluent or excipient. The compositions of the invention can be used to selectively inhibit TRPA1 in patients (e.g, humans).

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or and embodiment thereof and at least one pharmaceutically acceptable carrier. The compositions of the invention can be used to selectively inhibit TRPA1 in patients (e.g, humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or its embodiments and compositions comprising compounds of Formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include Sustained-release preparations of a compound of the invention (e.g., compound of Formula I or an embodiment thereof) can be prepared. Suitable examples of sustained-release preparations include semipermeable matrices of solid hydrophobic polymers containing a compound of Formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I (or an embodiment thereof) is formulated in an acetate buffer, at pH 5. In another embodiment, the compounds of Formula I or an embodiment thereof are sterile. The compound may be stored, for example, as a solid or amorphous composition, as a lyophilized formulation or as an aqueous solution.

Formulations of a compound of the invention (e.g., compound of Formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound of the invention (e.g., compound of Formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™ Guildford.

Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506, 206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 μg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 μg kg to 1 mg/kg, about 1 μg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, G1 tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., *Br. J. Pharmacal.* 2004, 141, 1313-20; Yiangou, Y. et al., *Lancet* 2001, 357, 1338-39; Kimball, E. S. et al., *Neurogastroenterol. Motif.,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

In another specific embodiment, compounds of the invention can be administered to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neurpathic pain or inflammatory pain, comprising the step of administering a therapeutically effective amount of a compound according to formula (I) to a subject in need thereof.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

In one embodiment, the invention provides for a compound of formula (I) as described in any one of E1-E25 above, or a pharmaceutically acceptable salt thereof for use in medical therapy.

In another embodiment, the invention provides for a compound of formula (I) as described in any one of E1-E25 above or a pharmaceutically acceptable salt thereof for the treatment or prophylaxis of a respiratory disorder.

In another embodiment, the invention provides for the use of a compound of formula (I) as described in any one E1-E25 or a pharmaceutically acceptable salt thereof for the preparation of a medicament for the treatment or prophylaxis of a respiratory disorder.

In another embodiment, the invention provides for a method for treating a respiratory disorder in a mammal comprising administering a compound of formula (I) as described in any one of E1-E25 above or a pharmaceutically acceptable salt thereof to the mammal.

In another embodiment, the invention provides for a compound of formula (I) as described in any one of E1-E25 above or a pharmaceutically acceptable salt thereof for modulating TRPA1 activity.

In another embodiment, the invention provides for a compound of formula (I) as described in any one of E1 to E25 above or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound of formula (I) as described in any one of E1 to E25 above or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for modulating TRPA1 activity, comprising contacting TRPA1 with a compound of formula (I) as described in any one of E1 to E25 or a salt thereof.

In another embodiment, the invention provides for a method for treating a disease or condition mediated by TRPA1 activity in a mammal, comprising administering a compound of formula (I) as described in any one of E1 to E25 or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder.

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (R, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;
serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;
noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;
dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;
acetylcholinesterase inhibitors such as donepezil;
5-HT3 antagonists such as ondansetron;
metabotropic glutamate receptor (mGluR) antagonists;
local anaesthetic such as mexiletine and lidocaine;
corticosteroid such as dexamethasone;
antiarrhythmics, e.g., mexiletine and phenytoin;
muscarinic antagonists, e.g., tolterodine, propiverine, tropsium t chloride, darifenacin, solifenacin, temiverine and ipratropium;
cannabinoids;
vanilloid receptor agonists (e.g., resinferatoxin) or antagonists (e.g., capsazepine);
sedatives, e.g., glutethimide, meprobamate, methaqualone, and dichloralphenazone;
anxiolytics such as benzodiazepines,
antidepressants such as mirtazapine,
topical agents (e.g., lidocaine, capsacin and resiniferotoxin);
muscle relaxants such as benzodiazepines, baclofen, carisoprodol, chlorzoxazone, cyclobenzaprine, methocarbamol and orphrenadine;
anti-histamines or H1 antagonists;
NMDA receptor antagonists;
5-HT receptor agonists/antagonists;
PDEV inhibitors;
Tramadol®;
cholinergic (nicotinc) analgesics;
alpha-2-delta ligands;
prostaglandin E2 subtype antagonists;
leukotriene B4 antagonists;
5-lipoxygenase inhibitors; and
5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In another embodiment, provided is an invention as hereinbefore described.

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Schemes 1 to 4 below.

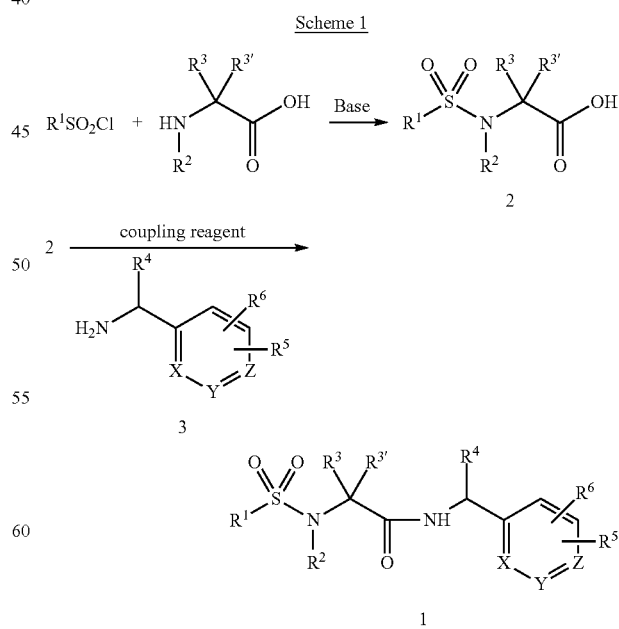

According to Scheme 1, an $R^2$-substituted amino acid may be reacted with a sulfonyl chloride to yield a sulfonamide carboxylic acid of formula 2. This transformation is well-documented in the chemical literature and familiar to those skilled in the art. It proceeds under various reactions conditions, for example, the amino acid and sulfonyl chloride can be combined in an aprotic solvent such as dichloromethane and treated with an excess of base such as triethylamine or potassium carbonate. Alternatively, the two reactants may be stirred in a solution of pyridine or a related polar, basic solvent to effect the coupling. A large variety and number of $R^2$-substituted amino acids may be purchased from commercial sources. Examples include sarcosine, 2-(propan-2-ylamino)acetic acid, 2-(ethylamino)-propanoic acid, N-methyl-L-serine, and 2-[(propan-2-yl)amino]propanoic acid. Similarly, numerous sulfonyl chlorides can be obtained from commercial sources including benzenesulfonyl chloride, 4-fluorobenzenesulfonyl chloride, 3,4-dichlorobenzenesulfonyl chloride, pyridine-3-sulfonyl chloride, 2-chloropyridine-5-sulfonyl chloride, 3-cyanobenzenesulfonyl chloride and 2-thiazolesulfonyl chloride. Intermediate of formula 2 can then be coupled to amines of formula 3 by a variety of well-established methods to yield compounds of formula 1. For example, the acid and amine can be combined in a solvent such as dimethylformamide and treated with any number of peptide coupling reagents such as 2-(1H-7-azabenzotriazol-1-yl)-1,1,3,3-tetramethyl uronium hexafluorophosphate methanaminium or bromo-tris-pyrrolidino phosphoniumhexafluorophosphate.

tecting group strategy could be employed for other distal functional groups such as alcohols, esters and ketones. α-Bromoacetamides of formula 6 are conveniently prepared by combining amines of formula 3 with 2-bromo acid chlorides. Many 2-bromo and 2-chloro acetic acid chlorides are commercially available including 2-bromopropionyl chloride, bromoacetyl chloride, chloroacetyl chloride, 2-bromobutyryl chloride and α-bromoisovaleryl chloride.

Scheme 3

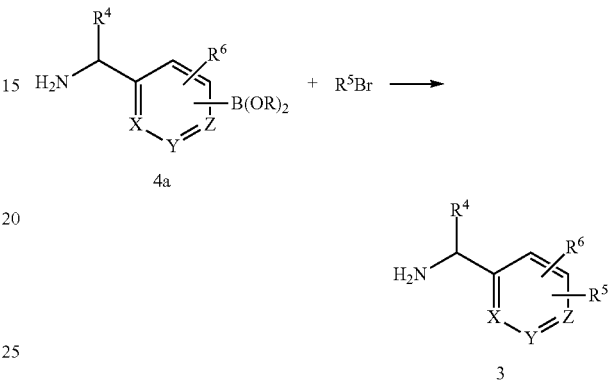

Scheme 2

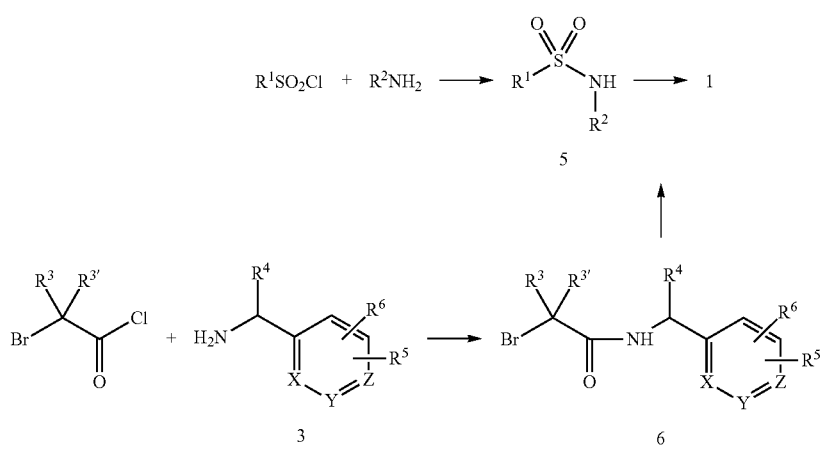

Alternatively, compounds of the invention may be made according to the processes outlined in Scheme 2. According to this scheme, sulfonamides of formula 5 can be readily prepared according to well established methods by combining sulfonyl chlorides containing $R^1$ with $R^2$-containing amines. For example, sulfonyl chloride may be added to a solution of $R^2$-amine and an organic base such as triethylamine in a polar, aprotic solvent such as THF. Alternatively, the reagents may be combined in a moderately basic solvent such as pyridine. $R^2$-containing amines are readily available from commercial sources including methylamine, ethylamine, isopropylamine, cyclopropylamine, ethanolamine, 1-amino-2-propanol. If $R^2$-containing amines contain a remote functional group, for example, 3-aminocyclobutane, then the distal amine may be protected using well known protecting groups as described in "Protective Groups in Organic Synthesis" [T. W. Greene and P. G. M. Wuts, 3$^{rd}$ Edition, John Wiley and Sons, N.Y. 1999]. A similar pro- -continued

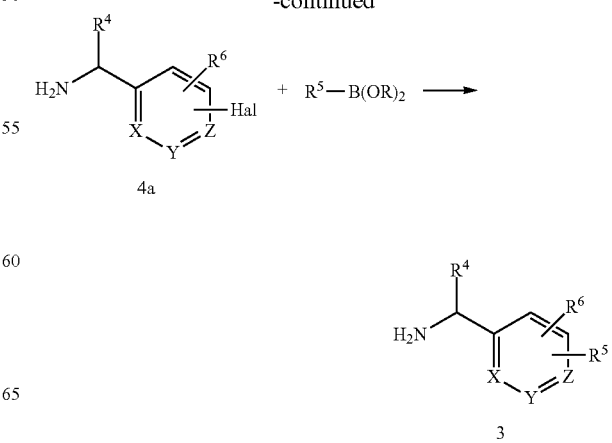

As shown in Scheme 3, intermediates of the general structure 3 may be synthesized by well-established methods. For example, the bond between the central aromatic ring and R⁵ may be created by a number of efficient metal-catalyzed coupling methods such as method that has come to be known as the Suzuki coupling. Under this scheme either of the two groups to be linked may be boronic acid or ester or halogen/pseudo-halogen. The other coupling partner would then be halogen/pseudo-halogen or boronic acid/ester respectively. Conditions for effecting this coupling include heating the boronic acid and aryl halide in a polar solvent mixture such as dioxane/water in the presence of an organic or inorganic base such as triethylamine or potassium carbonate and using a palladium catalyst such as tetrakis [triphenylphosphine] palladium or palladium (II) acetate.

Numerous starting materials of formula 4a and 4b may be purchased commercially. For example, 2-chloro-6-(trifluoromethoxy)-4-pyridinemethanamine, 2-bromo-4-pyridinemethanamine hydrochloride, (3,6-dichloropyridazin-4-yl)methanamine, 4-aminomethyl-6-chloropyrimidine, (3-aminomethylphenyl)boronic acid hydrochloride, 5-(aminomethyl)-2-fluorophenylboronic acid, HCl, [5-(aminomethyl)-2-methylphenyl]boronic acid, (5-bromopyridin-3-yl)methanamine, 3-(aminomethyl)-5-bromopyridin-2-ol, (5-bromo-2-chloro-pyridin-3-yl)-methanamine hydrochloride, (4-bromopyridin-2-yl)methanamine, (4-bromo-6-(trifluoromethyl)pyridin-2-yl)methanamine, 2-bromo-4-pyridinethylamine, (2-bromo-5-chloropyridin-4-yl)methanamine.

Scheme 4

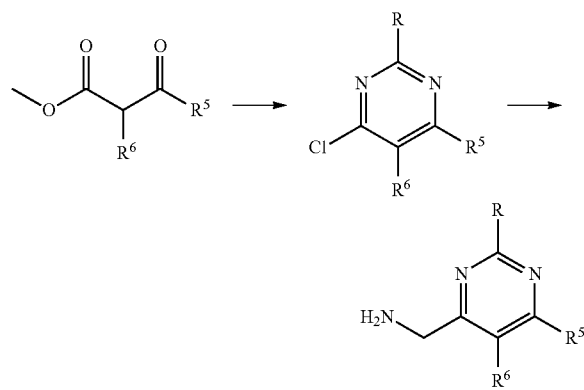

Compounds of the invention for which X=Z=N may be made by known methods for synthesizing pyrimidines. For example, they may be made by a process outlined in Scheme 4 in which an arylketoester is reacted with an amidine or an appropriate equivalent to give 4-arylpyrimidinones. This intermediate could then by chlorinated under established conditions such as heating in phosphorus oxychloride. The chloride could then be converted to the nitrile by a number of well-known methods and then reduced to the aminomethyl group. For example, the chloropyrimidine could be heated with potassium cyanide in a polar solvent such as DMSO to yield cyanopyrimidine. Alternatively, the chloropyrimidine could be treated with zinc cyanide and a catalytic amount of a transition metal catalyst such as tetrakis[triphenylphosphine]palladium in a polar solvent such as N-methylpyrrolidinone or THF. The nitrile could be subsequently reduced by dissolving it in a polar solvent such as ethanol and treated with a catalytic amount of metal catalyst such as palladium on carbon and shaken under a hydrogen atmosphere or pressure, for example, 60 psi.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep C₁₈ column (5 μm, OBD™ 20×100 mm) from Waters Corporation, or a SunFire™ Prep C₁₈ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex II FTICR with a 4.7 Tesla magnet (from Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the ¹H NMR spectra acquired at 300 MHz) and a Varian® Inova400 NMR spectrometer (for the ¹H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

Example 1

2-[(4-Fluoro-benzenesulfonyl)-methyl-amino]-N-(4'-trifluoromethyl-biphenyl-3-ylmethyl)-acetamide

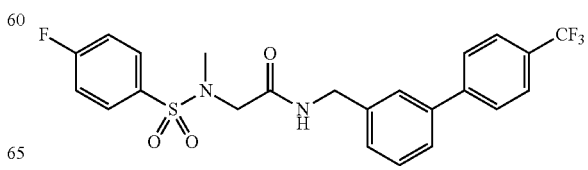

A suspension (3-aminomethylphenyl)boronic acid hydrochloride (5.0 g, 27 mmol), potassium phosphate tribasic (17.2 g, 81 mmol), and 1-bromo-4-(trifluoromethyl)benzene were combined in 5/1 dimethoxyethane/water (100 mL) at 25° C. was purged with nitrogen gas. The solution was then treated with tetrakis(triphenylphosphine)palladium(0) (2.0 mg, 1.73 mmol)) and then sealed and heated to 120° C. for 16 h. The reaction mixture was cooled to 25° C., unsealed and poured into water. The aqueous phase was extracted with ethyl acetate. The combined organic layers were washed with brine and dried over magnesium sulfate. Filtration followed by concentration in vacuo gave a brown solid. Flash chromatography (5-8% $CH_3OH$/2% $Et_3N$ in $CH_2Cl_2$) afforded C-(4'-trifluoromethyl-biphenyl-3-yl)-methylamine as an oil. MH+=252.

A solution of (4'-trifluoromethyl-biphenyl-3-yl)-methylamine (200 mg, 796 μmol) and 2-(tert-butoxycarbonyl(methyl)amino)acetic acid (226 mg, 1.19 mmol) in DMF (3 mL) at 25° C. was treated with HATU (605 mg, 1.59 mmol). The reaction mixture was stirred for 14 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded a heavy oil which was dissolved in 50/50 $CH_2Cl_2$/trifluoroacetic acid. The resulting solution was stirred for 1 h after which all volatiles were removed under reduced pressure. The resulting residue was suspended in 0.5M aqueous potassium carbonate solution and the suspension was extracted twice with $CH_2Cl_2$. The combined organic layers were dried over anhydrous sodium sulfate, filtered and concentrated in vacuo to yield 2-(methylamino)-N-((4'-(trifluoromethyl)biphenyl-3-yl)methyl)acetamide (190 mg, 74%) as a heavy oil.

A solution of 2-(methylamino)-N-((4'-(trifluoromethyl)biphenyl-3-yl)methyl)acetamide (190 mg, 0.59 μmol) and triethylamine (99 μL, 707 μmol) in $CH_2Cl_2$ (3 mL) at 25° C. was treated with 4-fluorobenzene-1-sulfonyl chloride (103 mg, 531 μmol). After 1 h the reaction mixture was concentrated in vacuo. Flash chromatography (50/50 hexanes/ethyl acetate) afforded 2-[(4-fluoro-benzenesulfonyl)-methylamino]-N-(4'-trifluoromethyl-biphenyl-3-ylmethyl)-acetamide (188 mg, 66%) as a white solid. MH+=481.

Example 2

(S)-2-[(4-Fluoro-benzenesulfonyl)-methyl-amino]-N-(4'-trifluoromethyl-biphenyl-3-ylmethyl)-propionamide

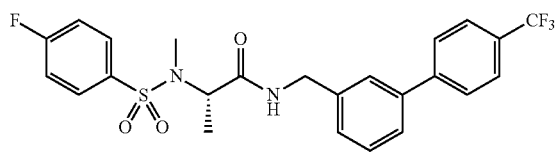 [SMILES: C[C@@H](C(=O)NCc1cccc(-c2ccc(C(F)(F)F)cc2)c1)N(C)S(=O)(=O)c1ccc(F)cc1]

A solution of (4'-(trifluoromethyl) biphenyl-3-yl)methanamine (150 mg, 0.6 mmol), (S)-2-(tert-butoxycarbonyl-methyl-amino)-propionic acid (121 mg, 0.6 mmol) and N,N-diisopropylethylamine (300 μL, 1.8 mmol) in DMF (2.5 mL) was treated with HATU (227 mg, 0.6 mmol). The reaction mixture was stirred for 16 h. The reaction mixture was then diluted with brine (25 mL) and extracted twice with ethyl acetate. The organic layer was dried over $Na_2SO_4$, filtered and concentrated in vacuo. Flash chromatography (5% $CH_3OH$ in $CH_2Cl_2$) afforded methyl-{(S)-1-[(4'-trifluoromethyl-biphenyl-3-ylmethyl)-carbamoyl]-ethyl}-carbamic acid tert-butyl ester (280 mg) as a heavy oil. MH+=437.0

A solution of methyl-{(S)-1-[(4'-trifluoromethyl-biphenyl-3-ylmethyl)-carbamoyl]-ethyl}-carbamic acid tert-butyl ester (280 mg, crude) in $CH_2Cl_2$ (5.0 mL) was treated with trifluoroacetic acid (410 μL). The solution was stirred for 17 h after which all volatiles were removed under reduced pressure to yield (S)-2-methylamino-N-(4'-trifluoromethyl-biphenyl-3-ylmethyl)-propionamide; compound with trifluoro-acetic acid (290 mg). MH+=336.8

A solution of (S)-2-methylamino-N-(4'-trifluoromethyl-biphenyl-3-ylmethyl)-propionamide; compound with trifluoroacetic acid (290 mg), triethylamine (230 μL, 1.66 mmol) in $CH_2Cl_2$ (5 mL) was treated with 4-fluorobenzenesulfonyl chloride (107 mg, 0.55 mmol) and the reaction mixture was stirred for 2 h. The reaction mixture was then concentrated under reduced pressure and the crude material was purified by silica gel chromatography (40% ethyl acetate in hexanes) to yield (S)-2-[(4-fluoro-benzenesulfonyl)-methyl-amino]-N-(4'-trifluoromethyl-biphenyl-3-ylmethyl)-propionamide (95 mg, 32% from (4'-(trifluoromethyl)biphenyl-3-yl)methanamine) as a white solid. MH+=493.6

Example 3

2-(4-Fluoro-benzenesulfonylamino)-N-(4'-trifluoromethyl-biphenyl-3-ylmethyl)-acetamide

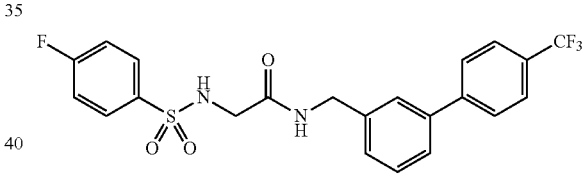

(R)-2-[(4-Fluoro-benzenesulfonyl)-methyl-amino]-N-(4'-trifluoromethyl-biphenyl-3-ylmethyl)-propionamide was prepared using N-Boc glycine as a starting material according to the methods described for Example 2. MH+=464.8

Example 4

(R)-2-[(4-Fluoro-benzenesulfonyl)-methyl-amino]-N-(4'-trifluoromethyl-biphenyl-3-ylmethyl)-propionamide

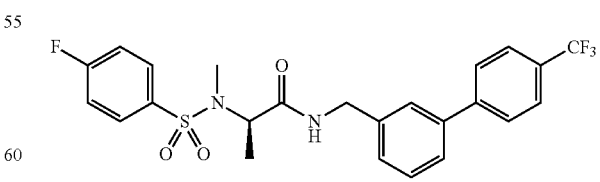

(R)-2-[(4-Fluoro-benzenesulfonyl)-methyl-amino]-N-(4'-trifluoromethyl-biphenyl-3-ylmethyl)-propionamide was prepared using (R)-2-(tert-butoxycarbonyl-methyl-amino)-propionic acid according to the methods described for Example 2. MH+=493.0

Example 5

(S)-2-[(4-Fluoro-benzenesulfonyl)-methyl-amino]-3-methyl-N-(4'-trifluoromethyl-biphenyl-3-ylmethyl)-butyramide

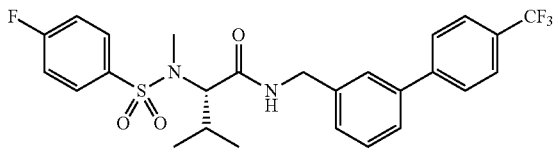 [SMILES: CC(C)[C@@H](C(=O)NCc1cccc(-c2ccc(C(F)(F)F)cc2)c1)N(C)S(=O)(=O)c1ccc(F)cc1]

(S)-2-[(4-Fluoro-benzenesulfonyl)-methyl-amino]-3-methyl-N-(4'-trifluoromethyl-biphenyl-3-ylmethyl)-butyramide was prepared using (S)-2-(tert-butoxycarbonyl-methyl-amino)-3-methyl-butyric acid according to the methods described for Example 2. MH+=521.0

Example 6

(R)-2-[(4-Fluoro-benzenesulfonyl)-methyl-amino]-3-methyl-N-(4'-trifluoromethyl-biphenyl-3-ylmethyl)-butyramide

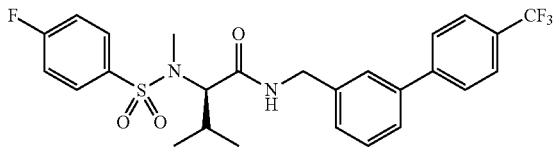 [SMILES: CC(C)[C@H](C(=O)NCc1cccc(-c2ccc(C(F)(F)F)cc2)c1)N(C)S(=O)(=O)c1ccc(F)cc1]

(R)-2-[(4-Fluorobenzenesulfonyl)-methyl-amino]-3-methyl-N-(4'-trifluoromethyl-biphenyl-3-ylmethyl)-butyramide was prepared using (R)-2-(tert-butoxycarbonyl-methyl-amino)-3-methyl-butyric acid according to the methods described for Example 2. MH+=521.2

Example 7

2-[(4-Fluoro-benzenesulfonyl)-methyl-amino]-2-methyl-N-(4'-trifluoromethyl-biphenyl-3-ylmethyl)-propionamide

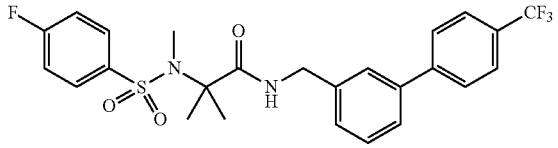 [SMILES: CN(C(C)(C)C(=O)NCc1cccc(-c2ccc(C(F)(F)F)cc2)c1)S(=O)(=O)c1ccc(F)cc1]

In a 10 mL pear-shaped flask, 2-(tert-butoxycarbonyl (methyl)amino)-2-methylpropanoic acid (300 mg, 1.38 mmol, Eq: 1.00), (4'-(trifluoromethyl)biphenyl-3-yl)methanamine (347 mg, 1.38 mmol, Eq: 1.00) and DIPEA (535 mg, 723 μl, 4.14 mmol, Eq: 3) were combined with DMF (2.00 ml) to give a colorless solution. HATU (525 mg, 1.38 mmol, Eq: 1.00) was added and stirred at 25° C. overnight. The reaction was checked by LC-MS. MH+(−100)=350 was found (loss of Boc group). The reaction mixture was diluted with brine and water, extracted with ethyl acetate (2×50 ml). The combined organic layers were washed with brine and water, dried over magnesium sulfate, filtered and concentrated in vacuo to give oil. The crude material was purified by flash chromatography (silica gel, 40+g, 0% to 10% CH₃OH/CH₂Cl₂ with 3% NH₄OH) to afford 2-methyl-2-(methylamino)-N-((4'-(trifluoromethyl)biphenyl-3-yl)methyl)propanamide (60 mg, 9.6%) as a waxy solid. MH+=450.

In a 10 mL round-bottomed flask, 2-methyl-2-(methylamino)-N-((4'-(trifluoromethyl)biphenyl-3-yl)methyl)propanamide (50 mg, 143 μmol, Eq: 1.00) was combined with CH₂Cl₂ (2 ml) to give a colorless solution. Triethylamine (21.7 mg, 29.8 μl, 214 μmol, Eq: 1.5) and 4-fluorobenzene-1-sulfonyl chloride (27.8 mg, 143 μmol, Eq: 1.00) were added and stirred at 25° C. for 2 h. The crude reaction mixture was concentrated in vacuo. Flash chromatography (50/50 hexanes/ethyl acetate to 10% ethyl acetate/dichloromethane) afforded 2-[(4-fluorobenzenesulfonyl)-methyl-amino]-2-methyl-N-(4'-trifluoromethyl-biphenyl-3-ylmethyl)-propionamide (26 mg, 34%) as a white solid. MH+=509.

Example 8

2-[(4-Fluoro-benzenesulfonyl)-methyl-amino]-N-(6-fluoro-4'-trifluoromethyl-biphenyl-3-ylmethyl)-acetamide

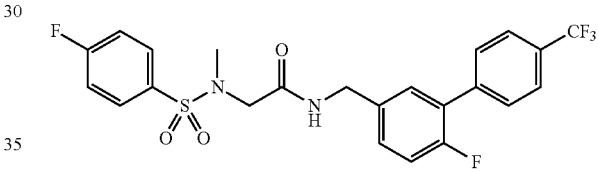

A solution of 4-fluoro-3-(4,4,5,5-tetramethyl-[1,3,2]dioxaborolan-2-yl)-benzylamine (1.00 g, 3.98 mmol), 1-bromo-4-trifluoromethyl-benzene (0.90 g, 3.98 mmol) and potassium phosphate-dibasic (2.54 g, 11.9 mmol) in 5/1 dimethoxyethane/water (12 mL) at 25° C. was purged with nitrogen gas and evacuated three times. The solution was then treated with tetrakis(triphenylphosphine)palladium(0) (230 mg, 199 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (10% CH₃OH/1% NH₄OH in ethyl acetate) afforded C-(6-fluoro-4'-trifluoromethyl-biphenyl-3-yl)-methylamine (160 mg, 15%) as a light oil.

A solution of C-(6-fluoro-4'-trifluoromethyl-biphenyl-3-yl)-methylamine (32.7 mg, 121 μmol) and [(4-fluoro-benzenesulfonyl)-methyl-amino]-acetic acid (30 mg, 121 μmol) in CH₂Cl₂ (5 mL) at 25° C. was treated with HATU (46.1 mg, 121 μmol). N,N-Diisopropylethylamine (31.4 mg, 243 μmol) was added to the solution. The reaction mixture was stirred for 2 h. The reaction mixture was then poured into 0.2M aqueous KHSO₄ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methylamino]-N-(6-fluoro-4'-trifluoromethyl-biphenyl-3-ylmethyl)-acetamide (33.5 mg, 55%) as a white solid. MH+=498.9.

Example 9

2-[(4-Fluoro-benzenesulfonyl)-methyl-amino]-N-(2-fluoro-4'-trifluoromethyl-biphenyl-3-ylmethyl)-acetamide

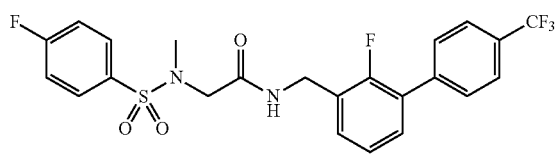

A solution of 3-(aminomethyl)-2-fluorophenylboronic acid hydrochloride (1.00 g, 4.87 mmol), 1-bromo-4-trifluoromethyl-benzene (1.10 g, 4.87 mmol) and potassium phosphate-dibasic (3.10 g, 14.6 mmol) in 5/1 dimethoxyethane/water (12 mL) at 25° C. was purged with nitrogen gas and evacuated three times. The solution was then treated with tetrakis(triphenylphosphine)palladium(0) (281 mg, 243 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (10% CH$_3$OH/1% NH$_4$OH in ethyl acetate) afforded C-(2-fluoro-4'-trifluoromethyl-biphenyl-3-yl)-methylamine (120 mg, 9%) as a light oil. M+H=269.9.

A solution of C-(2-fluoro-4'-trifluoromethyl-biphenyl-3-yl)-methylamine (38.1 mg, 142 µmol) and [(4-fluoro-benzenesulfonyl)-methyl-amino]-acetic acid (35 mg, 142 µmol) in CH$_2$Cl$_2$ (5 mL) at 25° C. was treated with HATU (53.8 mg, 142 µmol). N,N-Diisopropylethylamine (36.6 mg, 283 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-(2-fluoro-4'-trifluoromethyl-biphenyl-3-ylmethyl)-acetamide (36.8 mg, 52%) as a white solid. MH+=498.9.

Example 10

2-[(4-Fluoro-benzenesulfonyl)-methyl-amino]-N-(4'-trifluoromethyl-biphenyl-4-ylmethyl)-acetamide

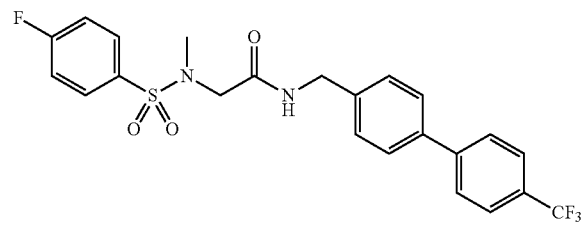 [SMILES: CN(CC(=O)NCc1ccc(-c2ccc(C(F)(F)F)cc2)cc1)S(=O)(=O)c1ccc(F)cc1]

A solution of 4-(aminomethyl)-phenylboronic acid hydrochloride (2.50 g, 13.3 mmol), 1-bromo-4-trifluoromethyl-benzene (3.99 g, 13.3 mmol) and potassium phosphate-dibasic (2.83 g, 13.3 mmol) in 5/1 dimethoxyethane/water (12 mL) at 25° C. was purged with nitrogen gas and evacuated three times. The solution was then treated with tetrakis(triphenylphosphine)palladium(0) (759 mg, 665 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (10% CH$_3$OH/1% NH$_4$OH in ethyl acetate) afforded C-(4'-trifluoromethyl-biphenyl-3-yl)-methylamine (2.1 g, 66%) as a light oil.

A solution of C-(4'-trifluoromethyl-biphenyl-4-yl)-methylamine (30.5 mg, 121 µmol) and [(4-fluoro-benzenesulfonyl)-methyl-amino]-acetic acid (30 mg, 121 µmol) in CH$_2$Cl$_2$ (5 mL) at 25° C. was treated with HATU (46.1 mg, 121 µmol). N,N-Diisopropylethylamine (31.4 mg, 243 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-(4'-trifluoromethyl-biphenyl-4-ylmethyl)-acetamide (32.8 mg, 56%) as a white solid. MH+=481.0.

Example 11

2-[(4-Fluoro-benzenesulfonyl)-methyl-amino]-N-(5-fluoro-4'-trifluoromethyl-biphenyl-3-ylmethyl)-acetamide

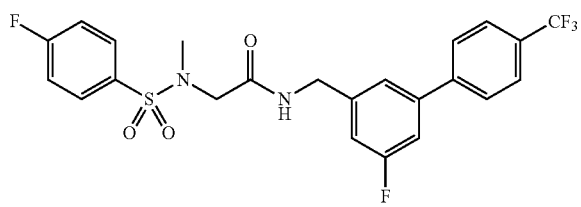 [SMILES: CN(CC(=O)NCc1cc(F)cc(-c2ccc(C(F)(F)F)cc2)c1)S(=O)(=O)c1ccc(F)cc1]

A solution of 4,4,5,5-tetramethyl-2-(4-trifluoromethyl-phenyl)-[1,3,2]dioxaborolane (1.00 g, 3.68 mmol), 3-bromo-5-fluoro-benzonitrile (0.74 g, 3.68 mmol) and potassium carbonate (0.51 g, 3.68 mmol) in DMF (5 mL) at 25° C. was purged with nitrogen gas and evacuated three times. The solution was then treated with tetrakis(triphenylphosphine)palladium(0) (212 mg, 184 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 5-fluoro-4'-trifluoromethyl-biphenyl-3-carbonitrile (820 mg, 84%) as a white solid.

A solution of 5-fluoro-4'-trifluoromethyl-biphenyl-3-carbonitrile (620 mg, 2.34 mmol), and 10% palladium on carbon (0.12 g, 0.12 mmol) in ethanol (10 mL) at 25° C. was stirred under 50 psi hydrogen pressure for 3 h. Filtration followed by concentration in vacuo gave C-(5-fluoro-4'-trifluoromethyl-biphenyl-3-yl)-methylamine (500 mg, 79%) as a brown oil. M+H=270.0.

A solution of C-(5-fluoro-4'-trifluoromethyl-biphenyl-3-yl)-methylamine (38.1 mg, 142 μmol) and [(4-fluoro-benzenesulfonyl)-methyl-amino]-acetic acid (35 mg, 142 μmol) in CH$_2$Cl$_2$ (5 mL) at 25° C. was treated with HATU (53.8 mg, 142 μmol). N,N-Diisopropylethylamine (36.6 mg, 283 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-(5-fluoro-4'-trifluoromethyl-biphenyl-3-ylmethyl)-acetamide (37.5 mg, 53%) as a white solid. MH+=498.9.

Example 12

2-[(4-Fluoro-benzenesulfonyl)-methyl-amino]-N-(4-fluoro-4'-trifluoromethyl-biphenyl-3-ylmethyl)-acetamide

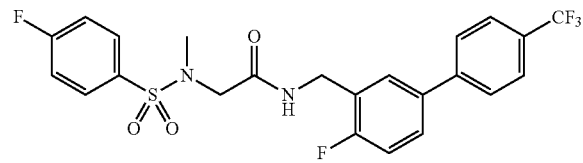 [SMILES: CN(CC(=O)NCc1cc(-c2ccc(C(F)(F)F)cc2)ccc1F)S(=O)(=O)c1ccc(F)cc1]

A solution of 4,4,5,5-tetramethyl-2-(4-trifluoromethyl-phenyl)-[1,3,2]dioxaborolane (1.00 g, 3.68 mmol), 5-bromo-2-fluoro-benzonitrile (0.74 g, 3.68 mmol) and potassium carbonate (0.51 g, 3.68 mmol) in DMF (5 mL) at 25° C. was purged with nitrogen gas and evacuated three times. The solution was then treated with tetrakis(triphenylphosphine)palladium(0) (212 mg, 184 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 4-fluoro-4'-trifluoromethyl-biphenyl-3-carbonitrile (360 mg, 37%) as a white solid.

A solution of 4-fluoro-4'-trifluoromethyl-biphenyl-3-carbonitrile (360 mg, 1.36 mmol), and 10% palladium on carbon (68 mg, 0.068 mmol) in ethanol (10 mL) at 25° C. was stirred under 50 psi hydrogen pressure for 3 h. Filtration followed by concentration in vacuo gave C-(4-fluoro-4'-trifluoromethyl-biphenyl-3-yl)-methylamine (300 mg, 82%) as a brown oil. M+H=270.0.

A solution of C-(4-fluoro-4'-trifluoromethyl-biphenyl-3-yl)-methylamine (32.7 mg, 121 μmol) and [(4-fluoro-benzenesulfonyl)-methyl-amino]-acetic acid (30 mg, 121 μmol) in CH$_2$Cl$_2$ (5 mL) at 25° C. was treated with HATU (46.1 mg, 121 μmol). N,N-Diisopropylethylamine (31.4 mg, 243 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-(4-fluoro-4'-trifluoromethyl-biphenyl-3-ylmethyl)-acetamide (27.4 mg, 45%) as a white solid. MH+=498.9.

Example 13

2-[(4-fluoro-benzenesulfonyl)-(2,2,2-trifluoro-ethyl)-amino]-N-(4'-trifluoromethyl-biphenyl-3-ylmethyl)-acetamide

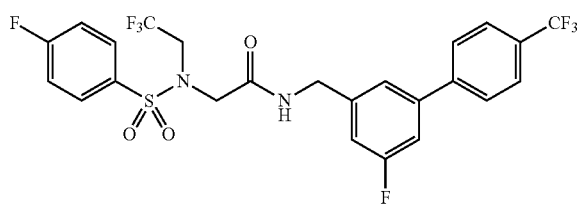 [SMILES: O=C(CN(CC(F)(F)F)S(=O)(=O)c1ccc(F)cc1)NCc1cc(F)cc(-c2ccc(C(F)(F)F)cc2)c1]

To a solution of (4'-(trifluoromethyl)biphenyl-3-yl)methanamine (500 mg, 1.99 mmol) and pyridine (644 μl, 7.96 mmol) in CH$_2$Cl$_2$ (25 mL) was added a solution of 2-bromoacetyl chloride (313 mg, 1.99 mmol) in CH$_2$Cl$_2$ (5 ml) at 5° C. The reaction mixture was stirred at 5° C. for 15 min and then rt for 1 h. CH$_2$Cl$_2$ and water were added. The organic layer was washed with 2 N HCl, brine, dried over anhydrous sodium sulfate, filtered and concentrated in vacuo to give 2-bromo-N-((4'-(trifluoromethyl)biphenyl-3-yl)methyl)acetamide (690 mg, 89%) as a white solid which was directly used for next step without further purification. MH$^+$=373.

To a solution of 2,2,2-trifluoroethylamine (373 mg, 3.77 mmol) in pyridine (5 mL) was added 4-fluorobenzene-1-sulfonyl chloride (734 mg, 3.77 mmol). The reaction mixture was stirred at room temperature for 12 h. After removal of solvent, water was added. pH was adjust to acidic using 1N HCl. The product was extracted with ethyl acetate. The organic layer was washed with brine, dried over anhydrous sodium sulfate, filtered and concentrated in vacuo to give 4-fluoro-N-(2,2,2-trifluoroethyl)benzenesulfonamide (970 mg, 100%) as a white solid which was directly used for next step without further purification. MH$^-$=256.

To a solution of 4-fluoro-N-(2,2,2-trifluoroethyl)benzenesulfonamide (30 mg, 117 μmol) and 2-bromo-N-((4'-(trifluoromethyl)biphenyl-3-yl)methyl)acetamide (43.4 mg, 117 μmol) in DMF (2 ml) was added cesium carbonate (114 mg, 350 μmol). The reaction mixture was stirred at room temperature for 12 h. Ethyl acetate and water were added. The organic layer was washed with 1 N HCl, brine, dried over anhydrous sodium sulfate, filtered and concentrated in vacuo. Flash chromatography (70/30 hexane/ethyl acetate) afforded 2-[(4-fluoro-benzenesulfonyl)-(2,2,2-trifluoro-ethyl)-amino]-N-(4'-trifluoromethyl-biphenyl-3-ylmethyl)-acetamide (56 mg, 88%) as a white solid. MH+=549.

Example 14

2-[Ethyl-(4-fluoro-benzenesulfonyl)-amino]-N-(6-fluoro-4'-trifluoromethyl-biphenyl-3-ylmethyl)-acetamide

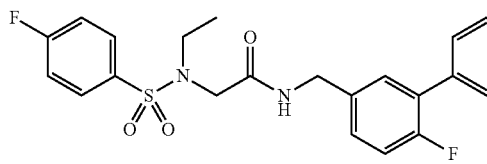

A solution of C-(6-fluoro-4'-trifluoromethyl-biphenyl-3-yl)-methylamine from Example 8 (30.9 mg, 115 μmol) and [ethyl-(4-fluoro-benzenesulfonyl)-amino]-acetic acid (30.0 mg, 115 μmol) in $CH_2Cl_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(6-fluoro-4'-trifluoromethyl-biphenyl-3-ylmethyl)-acetamide (15.3 mg, 26%) as a white solid. MH+=512.9.

Example 15

2-[Ethyl-(4-fluoro-benzenesulfonyl)-amino]-N-(5-fluoro-4'-trifluoromethyl-biphenyl-3-ylmethyl)-acetamide

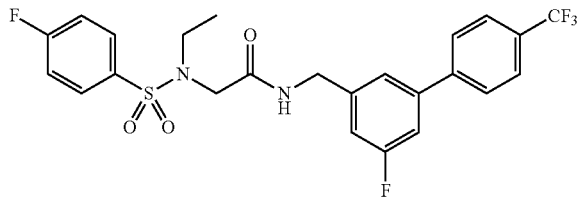 [SMILES: CCN(CC(=O)NCc1cc(F)cc(-c2ccc(C(F)(F)F)cc2)c1)S(=O)(=O)c1ccc(F)cc1]

A solution of C-(5-fluoro-4'-trifluoromethyl-biphenyl-3-yl)-methylamine from Example 11 (30.9 mg, 115 μmol) and [ethyl-(4-fluoro-benzenesulfonyl)-amino]-acetic acid (30.0 mg, 115 μmol) in $CH_2Cl_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(5-fluoro-4'-trifluoromethyl-biphenyl-3-ylmethyl)-acetamide (32.0 mg, 54%) as a white solid. MH+=512.9.

Example 16

2-[Ethyl-(4-fluoro-benzenesulfonyl)-amino]-N-(4-fluoro-4'-trifluoromethyl-biphenyl-3-ylmethyl)-acetamide

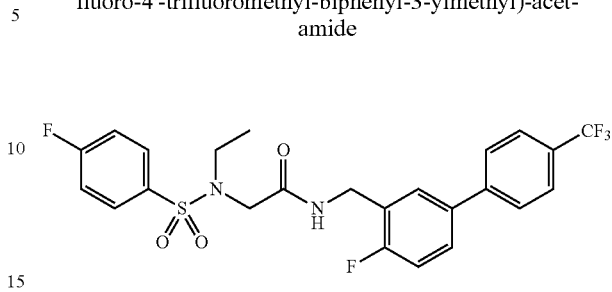

A solution of C-(4-fluoro-4'-trifluoromethyl-biphenyl-3-yl)-methylamine from Example 12 (30.9 mg, 115 μmol) and [ethyl-(4-fluoro-benzenesulfonyl)-amino]-acetic acid (30.0 mg, 115 μmol) in $CH_2Cl_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(4-fluoro-4'-trifluoromethyl-biphenyl-3-ylmethyl)-acetamide (28.1 mg, 48%) as a white solid. MH+=512.9.

Example 17

2-[Ethyl-(4-fluoro-benzenesulfonyl)-amino]-N-(4'-trifluoromethyl-biphenyl-4-ylmethyl)-acetamide

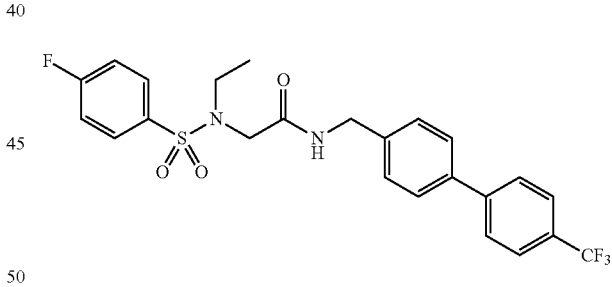

A solution of C-(4'-trifluoromethyl-biphenyl-4-yl)-methylamine from Example 10 (28.8 mg, 115 μmol) and [ethyl-(4-fluoro-benzenesulfonyl)-amino]-acetic acid (30 mg, 115 μmol) in $CH_2Cl_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(4'-trifluoromethyl-biphenyl-4-ylmethyl)-acetamide (47.9 mg, 84%) as a white solid. MH+=494.9.

Example 18

2-[Ethyl-(4-fluoro-benzenesulfonyl)-amino]-N-(3'-trifluoromethyl-biphenyl-4-ylmethyl)-acetamide

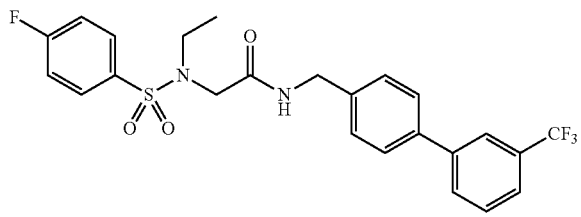 [SMILES: CCN(CC(=O)NCc1ccc(-c2cccc(C(F)(F)F)c2)cc1)S(=O)(=O)c1ccc(F)cc1]

A solution of 4-(aminomethyl)-phenylboronic acid hydrochloride (1.0 g, 5.34 mmol), 1-bromo-3-trifluoromethyl-benzene (1.2 g, 5.34 mmol) and potassium phosphate-dibasic (3.4 g, 16.0 mmol) in 5/1 dimethoxyethane/water (12 mL) at 25° C. was purged with nitrogen gas and evacuated three times. The solution was then treated with tetrakis(triphenylphosphine)palladium(0) (308 mg, 267 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (10% CH$_3$OH/1% NH$_4$OH in ethyl acetate) afforded C-(3'-trifluoromethyl-biphenyl-4-yl)-methylamine (180 mg, 13%) as a light oil. A solution of C-(3'-trifluoromethyl-biphenyl-4-yl)-methylamine (28.8 mg, 115 μmol) and [ethyl-(4-fluoro-benzenesulfonyl)-amino]-acetic acid (30 mg, 115 μmol) in CH$_2$Cl$_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(3'-trifluoromethyl-biphenyl-4-ylmethyl)-acetamide (29.0 mg, 51%) as a white solid. MH+=494.9.

Example 19

2-[(4-Fluoro-benzenesulfonyl)-(2-hydroxy-ethyl)-amino]-N-(4'-trifluoro methyl-biphenyl-3-ylmethyl)-acetamide A suspension of potassium carbonate (45 g, 326 mmol) and 2-aminoethanol (4.0 g, 65.5 mmol) were combined in acetonitrile (200 ml) and cooled with mechanical stirring to 5° C. Ethyl 2-bromoacetate (10.9 g, 65.5 mmol) in acetonitrile (40 ml) was added over 1 hr and stirred for an additional 1 hr at 5° C. The suspension was filtered through celite and concentrated in vacuo. The residue was treated with 50% ethyl acetate/hexane and filtered through celite and concentrated in vacuo to afford (2-hydroxy-ethylamino)-acetic acid ethyl ester as heavy oil (~8 g). $^1$H NMR (400 MHz, DMSO$_{d6}$) δ=4.16 (q, 2H), 4.14 (s, 3H), 1.22 (t, 2H) ppm.

(2-Hydroxy-ethylamino)-acetic acid ethyl ester (4.0 g, 27.2 mmol) and triethylamine (3.79 ml, 27.2 mmol) were combined with THF and cooled to 0° C. 4-Fluoro-benzenesulfonyl chloride (5.52 g, 29.9 mmol) in THF (40 ml) was added slowly and the reaction was stirred at ambient for 14 hr. The suspension was filtered through celite and concentrated in vacuo to afford [(4-fluoro-benzenesulfonyl)-(2-hydroxy-ethyl)-amino]-acetic acid ethyl ester as a white solid. $^1$H NMR (400 MHz, DMSO$_{d6}$)=7.93 (m, 2H), 7.44 (t, 2H), 4.75 (m, 1H), 4.19 (s, 3H), 4.08 (q, 2H), 3.52 (m, 2H), 3.24 (t, 2H) 1.18 (t, 2H) ppm.

[(4-Fluoro-benzenesulfonyl)-(2-hydroxy-ethyl)-amino]-acetic acid ethyl ester (340 mg, 1.11 mmol) was dissolved in dioxane (5 ml) and treated with a solution of potassium hydroxide (300 mg, 4.5 mmol) dissolved in 4 ml of water. This was stirred for 1 hr and the dioxane removed in vacuo. The pH was adjusted to 4 with 2N H$_3$PO$_4$ and the aqueous was extracted with 20% THF/CH$_2$Cl$_2$. The organics were dried (MgSO$_4$) and concentrated in vacuo to afford [(4-fluoro-benzenesulfonyl)-(2-hydroxy-ethyl)-amino]-acetic acid as a white solid. $^1$H NMR (400 MHz, DMSO$_{d6}$) 7.89 (m, 2H), 7.45 (t, 2H), 4.70 (br, 1H), 4.08 (s, 3H), 3.51 (t, 2H), 3.27 (t, 2H) ppm.

[(4-Fluoro-benzenesulfonyl)-(2-hydroxy-ethyl)-amino]-acetic acid was dissolved in a mixture of DMF (8 ml) and CH$_2$Cl$_2$ (4 ml) and cooled to 5° C. EDC (91.3 mg, 4.76 mmol) was added followed by (4'-trifluoromethyl-biphenyl-3-yl)-methylamine from Example 1 (109 mg, 4.33 mmol). This was stirred at ambient for 14 hr and concentrated in vacuo. The residue was purified by flash chromatography (40-50% ethyl acetate/hexane) to afford 2-[(4-fluoro-benzenesulfonyl)-(2-hydroxy-ethyl)-amino]-N-(4'-trifluoro methyl-biphenyl-3-ylmethyl)-acetamide as a white solid. MH+=511.

Example 20

2-[(4-Fluoro-benzenesulfonyl)-(2-hydroxy-propyl)-amino]-N-(4'-trifluoromethyl-biphenyl-3-ylmethyl)-acetamide

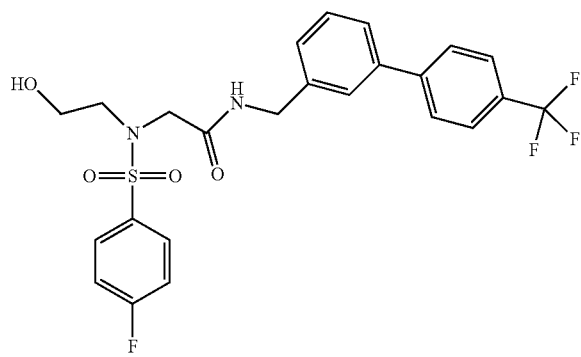 [SMILES: O=C(CN(CCO)S(=O)(=O)c1ccc(F)cc1)NCc1cccc(-c2ccc(C(F)(F)F)cc2)c1]

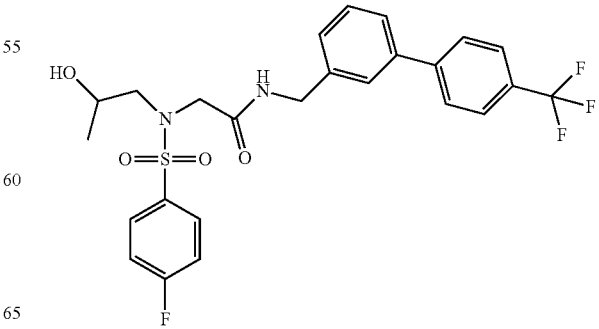

A solution of triethylamine (7.8 ml, 56 mmol) and 1-aminopropan-2-ol (3.5 g, 46.6 mmol) were combined in THF (150 ml) and cooled with mechanical stirring to 5° C. Methyl 2-bromoacetate (7.84 g, 51.3 mmol) in THF (50 ml) was added over 1 hr and stirred for an additional 3 hr at 15° C. The suspension was filtered through celite and concentrated in vacuo. The residue was purified by flash chromatography (ethyl acetate to 10% methanol/$CH_2Cl_2$) to afford (2-hydroxy-propylamino)-acetic acid methyl ester. $^1$H NMR (400 MHz, $DMSO_{d6}$) δ=4.5 (d, 1H), 4.14 (s, 3H), 3.62 (s, 3H), 3.4 (m, 2H), 3.36 (d, 2H) 1.01 (d, 3H) ppm.

A solution of (2-hydroxy-propylamino)-acetic acid methyl ester (1.2 g, 1.2 mmol) and triethylamine (3.4 ml, 24 mmol) in $CH_2Cl_2$ was cooled. 4-Fluoro-benzenesulfonyl chloride (1.6 g, 8.15 mmol) in $CH_2Cl_2$ (20 ml) was added slowly and stirred for 14 h at 20° C. The suspension was filtered through celite, concentrated in vacuo, and the residue was purified by flash chromatography to afford 1.8 g of [(4-fluoro-benzenesulfonyl)-(2-hydroxy-propyl)-amino]-acetic acid methyl ester as a white solid. MH+=306.

[(4-fluoro-benzenesulfonyl)-(2-hydroxy-propyl)-amino]-acetic acid methyl ester (900 mg, 2.95 mmol) was dissolved in dioxane (15 ml) and treated with a solution of potassium hydroxide (827 mg, 14.7 mmol) dissolved in 8 ml of water. This was stirred for 1 hr and the dioxane removed in vacuo. The pH was adjusted to 3 with 2N $H_3PO_4$ the opaque aqueous was extracted with 10% THF/$CH_2Cl_2$. The organics were dried ($MgSO_4$) and concentrated in vacuo to afford [(4-fluoro-benzenesulfonyl)-(2-hydroxy-propyl)-amino]-acetic acid as a solid. $^1$H NMR (400 MHz, $DMSO_{d6}$) δ=7.90 (m, 2H), 7.42 (t, 2H), 4.75 (br, 1H), 4.10 (m, 2H), 3.78 (m, 1H), 3.22 (m, 1H), 3.05 (m, 1H), 1.02 (d, 3H) ppm.

A solution of [(4-fluoro-benzenesulfonyl)-(2-hydroxy-propyl)-amino]-acetic acid (60 mg, 2.06 mmol) DMF (8 ml) was cooled to 5° C. EDC (79 mg, 4.12 mmol) was added followed by (4'-trifluoromethyl-biphenyl-3-yl)-methylamine from Example 1 (52 mg, 2.06 mmol). This was stirred at ambient temperature for 14 hr and concentrated in vacuo. The residue was purified by flash chromatography (50-100% ethyl acetate/hexane) to afford 2-[(4-fluoro-benzenesulfonyl)-(2-hydroxy-propyl)-amino]-N-(4'-trifluoromethyl-biphenyl-3-ylmethyl)-acetamide as a white solid. MH+=525.

Example 21

2-[(4-Fluoro-benzenesulfonyl)-methyl-amino]-N-[6-(4-trifluoromethyl-phenyl)-pyrimidin-4-ylmethyl]-acetamide

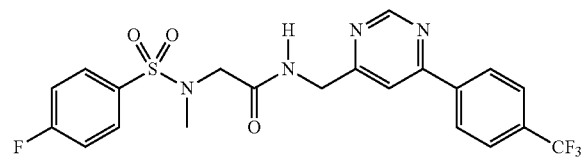 [SMILES: CN(CC(=O)NCc1cc(-c2ccc(C(F)(F)F)cc2)ncn1)S(=O)(=O)c1ccc(F)cc1]

A solution of 4-(trifluoromethyl)phenylboronic acid (5.0 g, 25.8 mmol), 4,6-dichloropyrimidine (3.92 g, 25.8 mmol), bis(triphenylphosphine)palladium(II) dichloride (362 mg, 516 μmol) and sodium carbonate (8.2 g, 77.4 mmol, Eq: 3) in a three solvent mixture of 50 mL DME, 7.5 mL ethanol and 7.5 mL water was heated at 130° C. for 7 h. Upon cooling to rt, the reaction mixture was poured into saturated aqueous ammonium chloride solution and extracted with three times with ethyl acetate. The combined organic layers were washed with water and brine and dried over Na2SO4. Filtration followed by removal of volatiles under reduced pressure gave a dark red solid. The mixture was purified by flash chromatography (5% diethyl ether in hexane) to give 4-chloro-6-(4-trifluoromethyl-phenyl)-pyrimidine (2.76 g) as a white solid.

4-Chloro-6-(4-(trifluoromethyl)phenyl)pyrimidine (2.55 g, 9.86 mmol) was dissolved in $CH_3CN$ (50 ml) and cooled to 0° C. Tetrabutylammonium cyanide (4.55 g, 16.9 mmol) and DABCO (3.32 g, 29.6 mmol) were added and the reaction mixture was stirred at 0° C. for 2 hours. The reaction mixture was then absorbed onto a small amount of silica gel and purified by flash column (0-20% EtOAc over 35 min) to give 6-(4-(trifluoromethyl)phenyl)pyrimidine-4-carbonitrile as a white solid (2.26 g; 92%).

To a solution of 6-(4-(trifluoromethyl)phenyl)pyrimidine-4-carbonitrile (1.5 g, 6.02 mmol) in ethanol (50 ml) was added palladium on carbon (10% Pd/C) (0.7 g, 658 μmol). The reaction was carried under a hydrogen atmosphere (55 psi) for 3 h. The reaction mixture was filtered through a pad of Celite and concentrated to give 6-(4-trifluoromethyl-phenyl)-pyrimidin-4-yl)methylamine (1.2 g, 79%) as a dark brown oil.

A solution of [(4-fluoro-benzenesulfonyl)-methyl-amino]-acetic acid (50 mg, 202 μmol), (6-(4-(trifluoromethyl)phenyl)pyrimidin-4-yl)methanamine (51.2 mg, 202 μmol), 1H-benzo[d][1,2,3]triazol-1-ol hydrate (1.55 mg, 10.1 μmol) and triethylamine (123 mg, 169 μL, 1.21 mmol) were dissolved in dichloromethane (2 mL) and stirred at rt for 10 min. Then 1-(3-dimethylaminopropyl)-3-ethylcarbodiimide hydrochloride (77.5 mg, 404 μmol) was added. The reaction mixture was stirred at room temperature for 16 h. The reaction mixture was concentrated. The residue was diluted with ethyl acetate and washed with water and brine sequentially. The organic layer was then dried over sodium sulfate, filtered and concentrated in vacuo. Flash chromatography (0-10% methanol in dichloromethane gradient over 20 min) afforded 2-[(4-fluoro-benzenesulfonyl)-methyl-amino]-N-[6-(4-trifluoromethyl-phenyl)-pyrimidin-4-ylmethyl]-acetamide as a white powder after lyophilization (40 mg, 41%). MH+=483.

Example 22

2-[Cyclopropyl-(4-fluoro-benzenesulfonyl)-amino]-N-(4'-trifluoromethyl-biphenyl-3-ylmethyl)-acetamide

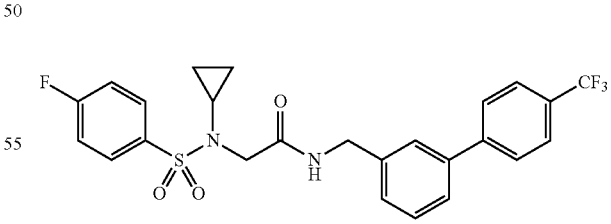

To a solution of 2-(tert-butoxycarbonyl(cyclopropyl)amino)acetic acid (100 mg, 465 μmol), (4'-(trifluoromethyl)biphenyl-3-yl)methanamine (128 mg, 511 μmol), 1-hydroxybenzotriazole hydrate (78.3 mg, 511 μmol) and N,N-diisopropylethylamine (243 μL, 1.39 mmol) in DMF (4 mL) was added HBPYU (220 mg, 511 μmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo to give crude tert-butyl cyclopropyl(2-oxo-2-((4'-(trifluoromethyl)biphenyl-3-yl)methylamino)ethyl)carbamate (208 mg, 100%) as a colorless oil which was directly used for next step without further purification. MH+=449.

A solution of tert-butyl cyclopropyl(2-oxo-2-((4'-(trifluoromethyl)biphenyl-3-yl)methylamino)ethyl)carbamate (208 mg, 464 µmol) in 4M HCl in dioxane (6 mL, 24.0 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give crude 2-(cyclopropylamino)-N-((4'-(trifluoromethyl)biphenyl-3-yl)methyl)acetamide (164 mg, 102%) as a colorless oil which was directly used for next step without further purification. MH+=349.

To a solution of 2-(cyclopropylamino)-N-((4'-(trifluoromethyl)biphenyl-3-yl)methyl)acetamide (162 mg, 465 µmol) and N,N-diisopropylethylamine (259 µl, 1.86 mmol) in CH$_2$Cl$_2$ (8 ml) were added 4-fluorobenzene-1-sulfonyl chloride (90.5 mg, 465 µmol). It was stirred at room temperature overnight. Ethyl acetate was added. The organic layer was washed with 1N HCl, brine, saturated sodium carbonate and brine, dried over anhydrous sodium sulfate, filtered and concentrated in vacuo. Flash chromatography (80/20 to 60/40 hexanes/ethyl acetate) afforded 2-[cyclopropyl-(4-fluoro-benzenesulfonyl)-amino]-N-(4'-trifluoromethyl-biphenyl-3-ylmethyl)-acetamide (194 mg, 82%) as a white solid. MH+=507.

Example 23

2-[Ethyl-(4-fluoro-benzenesulfonyl)-amino]-N-(4'-trifluoromethyl-biphenyl-3-ylmethyl)-acetamide

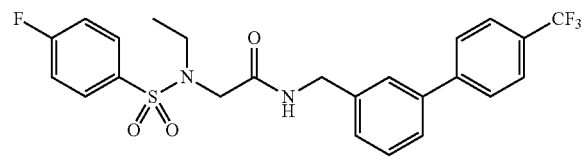 [SMILES: CCN(CC(=O)NCc1cccc(-c2ccc(C(F)(F)F)cc2)c1)S(=O)(=O)c1ccc(F)cc1]

To a solution of 2-(tert-butoxycarbonyl(ethyl)amino)acetic acid (50 mg, 246 µmol), (4'-(trifluoromethyl)biphenyl-3-yl)methanamine from Example 1 (68.0 mg, 271 µmol), 1-hydroxybenzotriazole hydrate (41.4 mg, 271 µmol) and N,N-diisopropylethylamine (129 µL, 738 µmol) in DMF (2 mL) was added HBPYU (117 mg, 271 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo to give crude of tert-butyl ethyl(2-oxo-2-((4'-(trifluoromethyl)biphenyl-3-yl)methylamino)ethyl)carbamate (107 mg, 100%) as a colorless oil which was directly used for next step without further purification. MH+=437.

A solution of tert-butyl ethyl(2-oxo-2-((4'-(trifluoromethyl)biphenyl-3-yl)methylamino)ethyl)carbamate (107 mg, 245 µmol) in 4M HCl in dioxane (6 mL, 24.0 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give crude 2-(ethylamino)-N-((4'-(trifluoromethyl)biphenyl-3-yl)methyl)acetamide (83 mg, 101%) as a colorless oil which was directly used for next step without further purification. MH+=337.

To a solution of 2-(ethylamino)-N-((4'-(trifluoromethyl)biphenyl-3-yl)methyl)acetamide (81 mg, 241 µmol) and triethylamine (134 µl, 963 µmol) in CH$_2$Cl$_2$ (8 ml) were added 4-fluorobenzene-1-sulfonyl chloride (46.9 mg, 241 µmol). It was stirred at room temperature overnight. Ethyl acetate was added. The organic layer was washed with 1N HCl, brine, saturated sodium carbonate and brine, dried over anhydrous sodium sulfate, filtered and concentrated in vacuo. Flash chromatography (60/40 to 50/50 hexanes/ethyl acetate) afforded 2-[ethyl-(4-fluoro-benzenesulfonyl)-amino]-N-(4'-trifluoromethyl-biphenyl-3-ylmethyl)-acetamide (194 mg, 82%) as a white solid. MH+=495.

Example 24

2-cyclopropyl-2-(4-fluoro-benzenesulfonylamino)-N-(4'-trifluoromethyl-biphenyl-3-ylmethyl)-acetamide

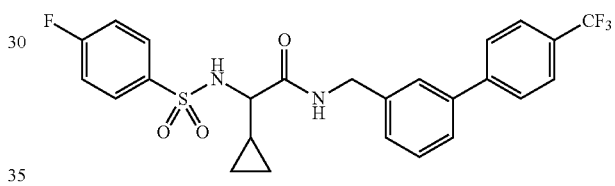

To a solution of 2-(tert-butoxycarbonylamino)-2-cyclopropylacetic acid (50 mg, 232 µmol), (4'-(trifluoromethyl)biphenyl-3-yl)methanamine (64.2 mg, 256 µmol), 1-hydroxybenzotriazole hydrate (39.1 mg, 256 µmol) and N,N-diisopropylethylamine (122 µL, 697 µmol) in DMF (2 mL) was added HBPYU (110 mg, 256 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo to give crude tert-butyl 1-cyclopropyl-2-oxo-2-((4'-(trifluoromethyl)biphenyl-3-yl)methylamino)ethylcarbamate (104 mg, 100%) as a white foam which was directly used for next step without further purification. MH+=449.

A solution of tert-butyl 1-cyclopropyl-2-oxo-2-((4'-(trifluoromethyl)biphenyl-3-yl)methylamino)ethylcarbamate (104 mg, 232 µmol) in 4M HCl in dioxane (6 mL, 24.0 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give crude 2-amino-2-cyclopropyl-N-(4'-trifluoromethyl-biphenyl-3-ylmethyl)-acetamide (80 mg, 99%) as a colorless oil which was directly used for next step without further purification. MH+=337.

To a solution of 2-amino-2-cyclopropyl-N-(4'-trifluoromethyl-biphenyl-3-ylmethyl)-acetamide (80 mg, 230 µmol) and triethylamine (128 µl, 919 µmol) in CH$_2$Cl$_2$ (4 ml) were added 4-fluorobenzene-1-sulfonyl chloride (44.7 mg, 230

μmol). It was stirred at room temperature overnight. Ethyl acetate was added. The organic layer was washed with 1N HCl, brine, saturated sodium carbonate and brine, dried over anhydrous sodium sulfate, filtered and concentrated in vacuo. Flash chromatography (60/40 to 50/50 hexanes/ethyl acetate) afforded 2-cyclopropyl-2-(4-fluoro-benzenesulfonylamino)-N-(4'-trifluoromethyl-biphenyl-3-ylmethyl)-acetamide (90 mg, 82%) as a white solid. MH+=507.

Example 25

2-[(5-chloro-thiophene-2-sulfonyl)-methyl-amino]-N-[6-(4-trifluoromethyl-phenyl)-pyrimidin-4-ylmethyl]-acetamide

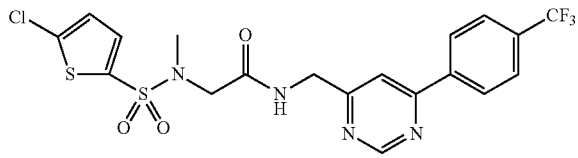 [SMILES: CN(CC(=O)NCc1cc(-c2ccc(C(F)(F)F)cc2)ncn1)S(=O)(=O)c1ccc(Cl)s1]

To a solution of 2-(tert-butoxycarbonyl(methyl)amino) acetic acid (82.2 mg, 434 μmol), [6-(4-trifluoromethyl-phenyl)-pyrimidin-4-yl]-methylamine from Example 21 (100 mg, 395 μmol), 1-hydroxybenzotriazole hydrate (66.5 mg, 434 μmol) and N,N-diisopropylethylamine (207 μL, 1.18 mmol) in DMF (2 mL) was added HBTU (165 mg, 434 μmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo to give crude of tert-butyl methyl(2-oxo-2-((6-(4-(trifluoromethyl)phenyl)pyrimidin-4-yl)methylamino)ethyl)carbamate (170 mg, 101%) as a white solid which was directly used for next step without further purification. MH+=425.

A solution of tert-butyl methyl(2-oxo-2-((6-(4-(trifluoromethyl)phenyl)pyrimidin-4-yl)methylamino)ethyl)carbamate (168 mg, 396 μmol) in 4M HCl in dioxane (6 mL, 24.0 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give crude 2-(methylamino)-N-((6-(4-(trifluoromethyl)phenyl)pyrimidin-4-yl)methyl)acetamide (123 mg, 96%) as a light brown solid which was directly used for next step without further purification. MH+=325.

To a solution of 2-(methylamino)-N-((6-(4-(trifluoromethyl)phenyl)pyrimidin-4-yl)methyl)acetamide (84 mg, 259 μmol) and N,N-diisopropylethylamine (136 μl, 777 μmol) in CH$_2$Cl$_2$ (3 ml) were added 5-chlorothiophene-2-sulfonyl chloride (56.2 mg, 259 μmol). It was stirred at room temperature overnight. Ethyl acetate was added. The organic layer was washed with 1N HCl, brine, saturated sodium carbonate and brine, dried over anhydrous sodium sulfate, filtered and concentrated in vacuo. Flash chromatography (ethyl acetate) afforded 2-[(5-chloro-thiophene-2-sulfonyl)-methyl-amino]-N-[6-(4-trifluoromethyl-phenyl)-pyrimidin-4-ylmethyl]-acetamide (58 mg, 44%) as a white solid. MH+=505.

Example 26

2-[methyl-(thiophene-2-sulfonyl)-amino]-N-[6-(4-trifluoromethyl-phenyl)-pyrimidin-4-ylmethyl]-acetamide

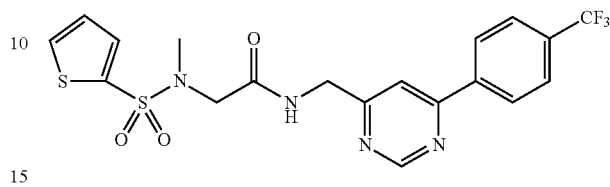

To a solution of 2-(methylamino)-N-((6-(4-(trifluoromethyl)phenyl)pyrimidin-4-yl)methyl)acetamide (84 mg, 259 μmol) (from example 25, step b) and N,N-diisopropylethylamine (136 μl, 777 μmol) in CH$_2$Cl$_2$ (3 ml) were added thiophene-2-sulfonyl chloride (47.3 mg, 259 μmol). It was stirred at room temperature overnight. Ethyl acetate was added. The organic layer was washed with 1N HCl, brine, saturated sodium carbonate and brine, dried over anhydrous sodium sulfate, filtered and concentrated in vacuo. Flash chromatography (ethyl acetate) afforded 2-[methyl-(thiophene-2-sulfonyl)-amino]-N-[6-(4-trifluoromethyl-phenyl)-pyrimidin-4-ylmethyl]-acetamide (56 mg, 46%) as a white solid. MH+=471.

Example 27

2-[(4-Fluoro-benzenesulfonyl)-isopropyl-amino]-N-[6-(4-trifluoromethyl-phenyl)-pyrimidin-4-ylmethyl]-acetamide

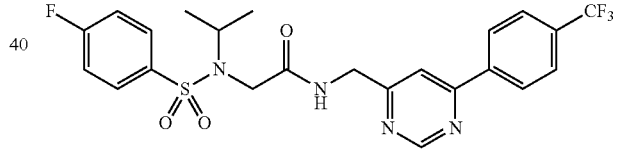

To a solution of 2-(tert-butoxycarbonyl(isopropyl)amino) acetic acid (660 mg, 3.04 mmol), [6-(4-trifluoromethyl-phenyl)-pyrimidin-4-yl]-methylamine hydrochloride from Example 21 (800 mg, 2.76 mmol), 1-hydroxybenzotriazole hydrate (465 mg, 3.04 mmol) and N,N-diisopropylethylamine (1.93 mL, 11.0 mmol) in DMF (15 mL) was added HBTU (1.15 g, 3.04 mmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (50/50 to 0/100 hexanes/ethyl acetate) afforded isopropyl-({[6-(4-trifluoromethyl-phenyl)-pyrimidin-4-ylmethyl]-carbamoyl}-methyl)-carbamic acid tert-butyl ester (900 mg, 72%) as a white solid. MH+=453.

A solution of isopropyl-({[6-(4-trifluoromethyl-phenyl)-pyrimidin-4-ylmethyl]-carbamoyl}-methyl)-carbamic acid tert-butyl ester (800 mg, 1.77 mmol) in 4M HCl in dioxane (20 mL, 80.1 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give 2-isopropylamino-N-[6-(4-trifluoromethyl-phenyl)-pyrimidin-4-ylmethyl]-acetamide (630 mg, 101%) as a light yellow solid. MH+=353.

To a solution of 2-(isopropylamino)-N-((6-(4-(trifluoromethyl)phenyl)pyrimidin-4-yl)methyl)acetamide (400 mg, 1.14 mmol) and N,N-diisopropylethylamine (595 µl, 3.41 mmol) in CH₂Cl₂ (10 ml) were added 4-fluorobenzene-1-sulfonyl chloride (243 mg, 1.25 mmol). It was stirred at room temperature overnight. Ethyl acetate was added. The organic layer was washed with saturated sodium carbonate and brine, dried over anhydrous sodium sulfate, filtered and concentrated in vacuo. Flash chromatography (10/90 to 0/100 hexanes/ethyl acetate) afforded 2-[(4-fluoro-benzenesulfonyl)-isopropyl-amino]-N-[6-(4-trifluoromethyl-phenyl)-pyrimidin-4- ylmethyl]-acetamide-acetamide (400 mg, 69%) as a white solid. MH+=511.

Example 28

2-[Ethyl-(4-fluoro-benzenesulfonyl)-amino]-N-[6-(4-trifluoromethyl-phenyl)-pyrimidin-4-ylmethyl]-acetamide

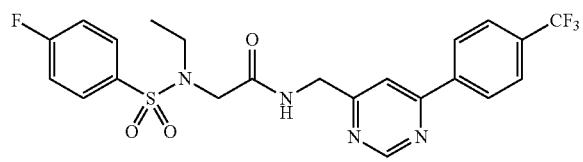 [SMILES: CCN(CC(=O)NCc1cc(-c2ccc(C(F)(F)F)cc2)ncn1)S(=O)(=O)c1ccc(F)cc1]

To a solution of 2-(tert-butoxycarbonyl(ethyl)amino)acetic acid (44.1 mg, 217 µmol), [6-(4-trifluoromethyl-phenyl)-pyrimidin-4-yl]-methylamine from Example 21 (50 mg, 197 µmol), 1-hydroxybenzotriazole hydrate (33.3 mg, 217 µmol) and N,N-diisopropylethylamine (103 µL, 592 µmol) in DMF (2 mL) was added HBTU (82.4 mg, 217 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (ethyl acetate) afforded tert-butyl ethyl(2-oxo-2-((6-(4-(trifluoromethyl)phenyl)pyrimidin-4-yl)methylamino)ethyl)carbamate (50 mg, 58%) as a light yellow oil. MH+=439.

A solution of tert-butyl ethyl(2-oxo-2-((6-(4-(trifluoromethyl)phenyl)pyrimidin-4-yl)methylamino)ethyl)carbamate (50 mg, 114 µmol) in 4M HCl in dioxane (5 mL, 20.0 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give 2-(ethylamino)-N-((6-(4-(trifluoromethyl)phenyl)pyrimidin-4-yl)methyl)acetamide (35 mg, 91%) as a light yellow solid. MH+=339.

To a solution of 2-(ethylamino)-N-((6-(4-(trifluoromethyl)phenyl)pyrimidin-4-yl)methyl)acetamide (35 mg, 103 µmol) and N,N-diisopropylethylamine (72.3 µl, 414 µmol) in CH₂Cl₂ (4 ml) were added 4-fluorobenzene-1-sulfonyl chloride (20.1 mg, 103 µmol). It was stirred at room temperature overnight. Ethyl acetate was added. The organic layer was washed with saturated sodium carbonate and brine, dried over anhydrous sodium sulfate, filtered and concentrated in vacuo. Flash chromatography (ethyl acetate) afforded 2-[ethyl-(4-fluoro-benzenesulfonyl)-amino]-N-[6-(4-trifluoromethyl-phenyl)-pyrimidin-4-ylmethyl]-acetamide (30 mg, 58%) as a white solid. MH+=497.

Example 29

2-[(4-Fluoro-benzenesulfonyl)-(2-methoxy-ethyl)-amino]-N-[6-(4-trifluoromethyl-phenyl)-pyrimidin-4-ylmethyl]-acetamide

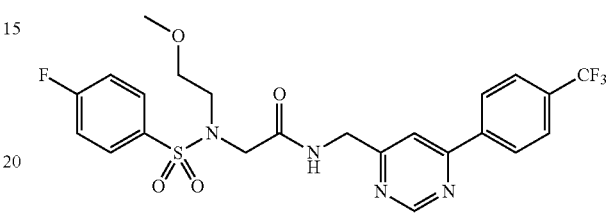

To a mixture of 2-methoxyethylamine (2.33 ml, 26.6 mmol) and potassium carbonate (14.7 g, 107 mmol) in acetonitrile (50 ml) was added the solution of methyl bromoacetate (4.07 g, 26.6 mmol) in acetonitrile (50 ml) dropwise at 0° C. over 1 h. After stirring at 0° C. for an additional hour, the solid was removed by filtration through celite. The filtrate was concentrated. The residue was dissolved in ether and the solid was removed by filtration. The filtrate was concentrated to give crude methyl 2-(2-methoxyethylamino)acetate (3.4 g, 87%) as a colorless oil, which was directly used for the next step without further purification.

To a solution of methyl 2-(2-methoxyethylamino)acetate (300 mg, 2.04 mmol) and N,N-diisopropylethylamine (712 µl, 4.08 mmol) in CH₂Cl₂ (8 ml) was added 4-fluorobenzene-1-sulfonyl chloride (397 mg, 2.04 mmol). It was stirred at room temperature overnight. Ethyl acetate was added. The organic layer was washed with saturated sodium carbonate and brine, dried over anhydrous sodium sulfate, filtered and concentrated in vacuo. Flash chromatography (100/0 to 60/40 hexane/ethyl acetate) afforded methyl 2-(4-fluoro-N-(2-methoxyethyl)phenylsulfonamido)acetate (390 mg, 63%) as a white solid. MH+=306.

To a solution of methyl 2-(4-fluoro-N-(2-methoxyethyl)phenylsulfonamido)acetate (390 mg, 1.28 mmol) in THF (5 mL) was added 1 N LiOH in water (5 mL, 5.01 mmol). The mixture stirred for 1 h. pH was adjusted to 4 with 2 N HCl dropwise. The aqueous layer was extracted with ethyl acetate. The organic layer was washed with brine, dried over anhydrous sodium sulfate, filtered and concentrated in vacuo to give 2-(4-fluoro-N-(2-methoxyethyl)phenylsulfonamido) acetic acid (370 mg, 99%) as a white solid which was directly used for the next step without further purification. MH+=292.

To a solution of 2-(4-fluoro-N-(2-methoxyethyl)phenylsulfonamido)acetic acid (31.6 mg, 109 µmol), [6-(4-trifluoromethyl-phenyl)-pyrimidin-4-yl]-methylamine from Example 21 (25 mg, 98.7 µmol), 1-hydroxybenzotriazole hydrate (16.6 mg, 109 µmol) and N,N-diisopropylethylamine (69.0 µl, 395 µmol) in DMF (2 mL) was added HBTU (41.2 mg, 109 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (0/100 to 40/60 THF/ethyl acetate) afforded 2-[(4-fluoro-benzenesulfonyl)-(2-methoxy-ethyl)-amino]-N-[6-(4-trifluoromethyl-phenyl)-pyrimidin-4-ylmethyl]-acetamide (39 mg, 75%) as a white solid. MH+=527.

Example 30

2-[(4-fluoro-benzenesulfonyl)-(2-hydroxy-ethyl)-amino]-N-[6-(4-trifluoromethyl-phenyl)-pyrimidin-4-ylmethyl]acetamide

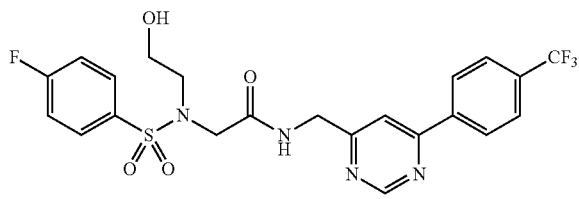 [SMILES: O=C(CN(CCO)S(=O)(=O)c1ccc(F)cc1)NCc1cc(-c2ccc(C(F)(F)F)cc2)ncn1]

To a solution of 2-(4-fluoro-N-(2-hydroxyethyl)phenylsulfonamido)acetic acid (32.8 mg, 118 µmol), [6-(4-trifluoromethyl-phenyl)-pyrimidin-4-yl]-methylamine (30 mg, 118 µmol), 1-hydroxybenzotriazole hydrate (20.0 mg, 130 µmol) and N,N-diisopropylethylamine (82.8 µl, 474 µmol) in DMF (4 ml) was added HBTU (49.4 mg, 130 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (0/100 to 50/50 THF/ethyl acetate) afforded 2-[(4-fluoro-benzenesulfonyl)-(2-hydroxy-ethyl)-amino]-N-[6-(4-trifluoromethyl-phenyl)-pyrimidin-4-ylmethyl]-acetamide (25 mg, 41%) as a white solid. MH+=513.

Example 31

2-[tert-Butyl-(4-fluoro-benzenesulfonyl)-amino]-N-[6-(4-trifluoromethyl-phenyl)-pyrimidin-4-ylmethyl]-acetamide

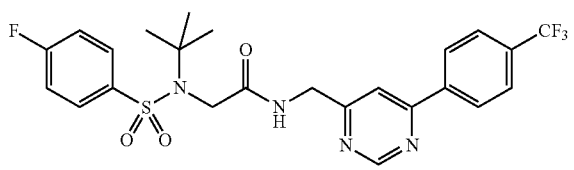 [SMILES: CC(C)(C)N(CC(=O)NCc1cc(-c2ccc(C(F)(F)F)cc2)ncn1)S(=O)(=O)c1ccc(F)cc1]

To a solution of tert-butylamine (3.82 g, 52.3 mmol) in acetonitrile (30 ml) was added the solution of methyl bromoacetate (2 g, 13.1 mmol) in acetonitrile (10 mL) dropwise at 0° C. This reaction was stirred at room temperature for an additional 4 h. After removal of the solid by filtration, the filtrate was concentrated and the residue was dissolved in ether. The solid was removed by filtration. The filtrate was concentrated to give tert-butylamino-acetic acid methyl ester (0.8 g, 42%) as a colorless oil which was used in the next step without further purification.

To a solution of tert-butylamino-acetic acid methyl ester (100 mg, 689 µmol) and N,N-diisopropylethylamine (241 µl, 1.38 mmol) in CH$_2$Cl$_2$ (8 ml) was added 4-fluorobenzene-1-sulfonyl chloride (174 mg, 895 µmol). Then DMAP (16.8 mg, 138 µmol) was added. It was stirred at room temperature overnight. Ethyl acetate was added. The organic layer was washed with saturated sodium carbonate and brine, dried over anhydrous sodium sulfate, filtered and concentrated in vacuo. Flash chromatography (100/0 to 60/40 hexane/ethyl acetate) afforded methyl 2-(N-tert-butyl-4-fluorophenylsulfonamido)acetate (150 mg, 72%) as a colorless oil. MH+=304.

To a solution of methyl 2-(N-tert-butyl-4-fluorophenylsulfonamido)acetate (100 mg, 330 µmol) in THF (2 mL) was added 1 N LiOH in water (1.32 mL, 1.32 mmol). The mixture stirred for 1 h. pH was adjusted to 4 with 2 N HCl. The aqueous layer was extracted with ethyl acetate. The organic layer was washed with brine, dried over anhydrous sodium sulfate, filtered and concentrated in vacuo to give 2-(N-tert-butyl-4-fluorophenylsulfonamido)acetic acid (70 mg, 73%) as a white solid which was directly used for the next step without further purification. MH+=290.

To a solution of 2-(N-tert-butyl-4-fluorophenylsulfonamido)acetic acid (41.1 mg, 142 µmol), [6-(4-trifluoromethyl-phenyl)-pyrimidin-4-yl]-methylamine from Example 21 (30 mg, 118 µmol), 1-hydroxybenzotriazole hydrate (20.0 mg, 130 µmol) and N,N-diisopropylethylamine (82.8 µl, 474 µmol) in DMF (2 ml) was added HBTU (49.4 mg, 130 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (0/100 to 70/30 hexane/ethyl acetate) afforded 2-[tert-butyl-(4-fluoro-benzenesulfonyl)-amino]-N-[6-(4-trifluoromethyl-phenyl)-pyrimidin-4-ylmethyl]-acetamide (30 mg, 48%) as a white solid. MH+=525.

Example 32

(S)-2-[(4-Fluoro-benzenesulfonyl)-isopropyl-amino]-N-[6-(4-trifluoromethyl-phenyl)-pyrimidin-4-ylmethyl]-propionamide

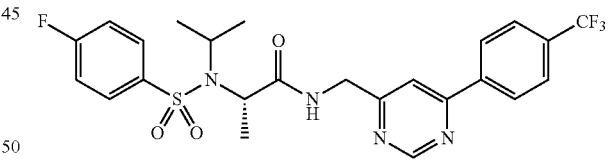

To a solution of (S)-2-(4-fluoro-N-isopropylphenylsulfonamido)propanoic acid (34.3 mg, 118 µmol), [6-(4-trifluoromethyl-phenyl)-pyrimidin-4-yl]-methylamine from Example 21 (30 mg, 118 µmol), 1-hydroxybenzotriazole hydrate (20.0 mg, 130 µmol) and N,N-diisopropylethylamine (82.8 µl, 474 µmol) in DMF (2 ml) was added HBTU (49.4 mg, 130 µmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (100/0 to 70/30 hexane/ethyl acetate) afforded (S)-2-[(4-fluoro-benzenesulfonyl)-isopropyl-amino]-N-[6-(4-trifluoromethyl-phenyl)-pyrimidin-4-ylmethyl]-propionamide (34 mg, 55%) as a white solid. MH+=525.

Example 33

2-[(4-Fluoro-benzenesulfonyl)-isopropyl-amino]-N-(4'-trifluoromethyl-biphenyl-4-ylmethyl)-acetamide

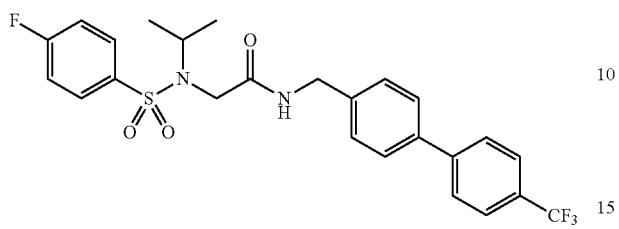

A solution of C-(4'-trifluoromethyl-biphenyl-4-yl)-methylamine from Example 17 (18.3 mg, 73 μmol) and [(4-fluoro-benzenesulfonyl)-isopropyl-amino]-acetic acid (20 mg, 73 μmol) in $CH_2Cl_2$ (5 mL) at 25° C. was treated with HATU (27.6 mg, 73 μmol). N,N-Diisopropylethylamine (18.8 mg, 145 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(4'-trifluoromethyl-biphenyl-4-ylmethyl)-acetamide (29 mg, 79%) as a white solid. MH+=509.0.

Example 34

2-[(4-Fluoro-benzenesulfonyl)-isopropyl-amino]-N-(3'-trifluoromethyl-biphenyl-4-ylmethyl)-acetamide

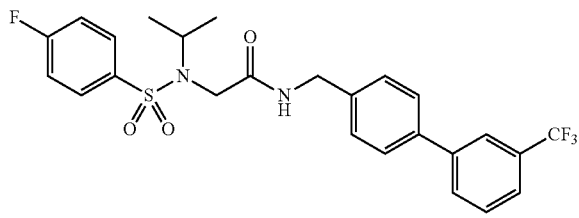 [SMILES: CC(C)N(CC(=O)NCc1ccc(-c2cccc(C(F)(F)F)c2)cc1)S(=O)(=O)c1ccc(F)cc1]

A solution of C-(3'-trifluoromethyl-biphenyl-4-yl)-methylamine from Example 18 (18.3 mg, 73 μmol) and [(4-fluoro-benzenesulfonyl)-isopropyl-amino]-acetic acid (20 mg, 73 μmol) in $CH_2Cl_2$ (5 mL) at 25° C. was treated with HATU (27.6 mg, 73 μmol). N,N-Diisopropylethylamine (18.8 mg, 145 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(3'-trifluoromethyl-biphenyl-4-ylmethyl)-acetamide (8.3 mg, 23%) as a white solid. MH+=509.0.

Example 35

2-[(4-Fluoro-benzenesulfonyl)-isopropyl-amino]-N-(6-fluoro-4'-trifluoromethyl-biphenyl-3-ylmethyl)-acetamide

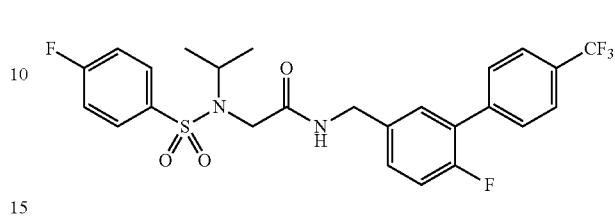

A solution of C-(6-fluoro-4'-trifluoromethyl-biphenyl-3-yl)-methylamine from Example 8 (19.6 mg, 73 μmol) and [(4-fluoro-benzenesulfonyl)-isopropyl-amino]-acetic acid (20 mg, 73 μmol) in $CH_2Cl_2$ (5 mL) at 25° C. was treated with HATU (27.6 mg, 73 μmol). N,N-Diisopropylethylamine (18.8 mg, 146 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(6-fluoro-4'-trifluoromethyl-biphenyl-3-ylmethyl)-acetamide (9.3 mg, 24%) as a white solid. MH+=527.0.

Example 36

2-[(4-Fluoro-benzenesulfonyl)-isopropyl-amino]-N-(5-fluoro-4'-trifluoromethyl-biphenyl-3-ylmethyl)-acetamide

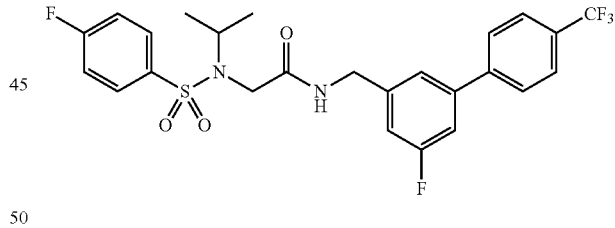

A solution of C-(5-fluoro-4'-trifluoromethyl-biphenyl-3-yl)-methylamine from Example 11 (19.6 mg, 73 μmol) and [(4-fluoro-benzenesulfonyl)-isopropyl-amino]-acetic acid (20 mg, 73 μmol) in $CH_2Cl_2$ (5 mL) at 25° C. was treated with HATU (27.6 mg, 73 μmol). N,N-Diisopropylethylamine (18.8 mg, 146 μmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(5-fluoro-4'-trifluoromethyl-biphenyl-3-ylmethyl)-acetamide (22.2 mg, 58%) as a white solid. MH+=527.0.

Example 37

2-[(4-Fluoro-benzenesulfonyl)-isopropyl-amino]-N-(4-fluoro-4'-trifluoromethyl-biphenyl-3-ylmethyl)-acetamide

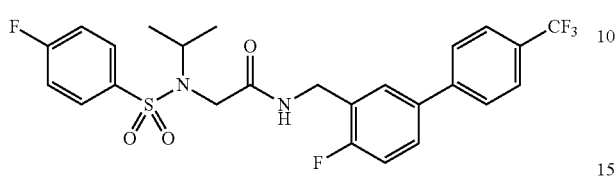

A solution of C-(4-fluoro-4'-trifluoromethyl-biphenyl-3-yl)-methylamine from Example 12 (19.6 mg, 73 µmol) and [(4-fluoro-benzenesulfonyl)-isopropyl-amino]-acetic acid (20 mg, 73 µmol) in $CH_2Cl_2$ (5 mL) at 25° C. was treated with HATU (27.6 mg, 73 µmol). N,N-Diisopropylethylamine (18.8 mg, 146 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(4-fluoro-4'-trifluoromethyl-biphenyl-3-ylmethyl)-acetamide (24.0 mg, 63%) as a white solid. MH+=527.0.

Example 38

(R)-2-[(4-Fluoro-benzenesulfonyl)-methyl-amino]-N-[6-(4-trifluoromethyl-phenyl)-pyrimidin-4-ylmethyl]-propionamide

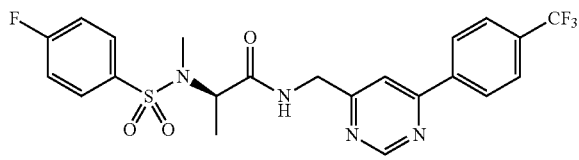

A solution of 6-(4-trifluoromethyl-phenyl)-pyrimidin-4-yl)methylamine from Example 21 (29.1 mg, 115 µmol) and (R)-2-[(4-fluoro-benzenesulfonyl)-methyl-amino]-propionic acid (30 mg, 115 µmol) in $CH_2Cl_2$ (5 mL) at 25° C. was treated with HATU (43.7 mg, 115 µmol). N,N-Diisopropylethylamine (29.7 mg, 230 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded (R)-2-[(4-fluoro-benzenesulfonyl)-methyl-amino]-N-[6-(4-trifluoromethyl-phenyl)-pyrimidin-4-ylmethyl]-propionamide (20.2 mg, 35%) as a white solid. MH+=496.9.

Example 39

2-[(4-Fluoro-benzenesulfonyl)-isopropyl-amino]-N-(4'-trifluoromethyl-biphenyl-3-ylmethyl)-acetamide

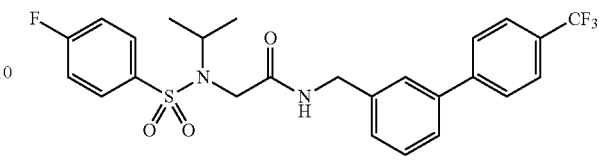

A solution of C-(4'-trifluoromethyl-biphenyl-3-yl)-methylamine from Example 1 (27.4 mg, 109 µmol) and [(4-fluoro-benzenesulfonyl)-isopropyl-amino]-acetic acid (30 mg, 109 µmol) in $CH_2Cl_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(4'-trifluoromethyl-biphenyl-3-ylmethyl)-acetamide (39.1 mg, 71%) as a white solid. MH+=509.0.

Example 40

2-[(4-Fluoro-benzenesulfonyl)-isopropyl-amino]-N-[3-(5-trifluoromethyl-pyridin-2-yl)-benzyl]-acetamide

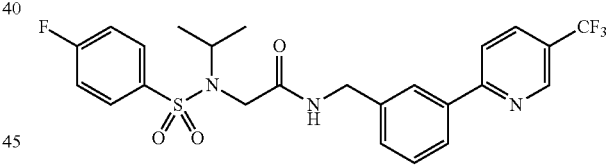

A solution of 3-(aminomethyl)-phenylboronic acid hydrochloride (2 g, 10.7 mmol), 2-chloro-5-trifluoromethyl-pyridine (1.94 g, 10.7 mmol) and cesium carbonate (10.5 g, 32.1 mmol) in 5/1 dimethoxyethane/water (12 mL) at 25° C. was purged with nitrogen gas and evacuated three times. The solution was then treated with tetrakis(triphenylphosphine)palladium(0) (618 mg, 535 µmol) and then sealed and heated to 85° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (10% $CH_3OH$/1% $NH_4OH$ in ethyl acetate) afforded 3-(5-trifluoromethyl-pyridin-2-yl)-benzylamine (1.2 g, 42%) as a light oil. MH+=253.0

A solution of 3-(5-trifluoromethyl-pyridin-2-yl)-benzylamine (18.3 mg, 73 µmol) and [(4-fluoro-benzenesulfonyl)-isopropyl-amino]-acetic acid (20.0 mg, 73 µmol) in $CH_2Cl_2$ (5 mL) at 25° C. was treated with HATU (27.6 mg, 73 µmol). N,N-Diisopropylethylamine (18.8 mg, 145 µmol) was added to the solution. The reaction mixture was stirred for 2 h. The reaction mixture was then poured into 0.2M aqueous KHSO₄ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[3-(5-trifluoromethyl-pyridin-2-yl)-benzyl]-acetamide (27.5 mg, 74%) as a white solid. MH+=510.3.

Example 41

2-[(4-Fluoro-benzenesulfonyl)-methyl-amino]-N-[3-(5-trifluoromethyl-pyridin-2-yl)-benzyl]-acetamide

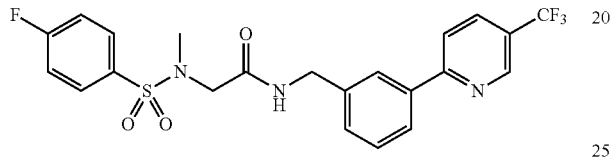

A solution of 3-(5-trifluoromethyl-pyridin-2-yl)-benzylamine (20.4 mg, 81 µmol) and [(4-fluoro-benzenesulfonyl)-methyl-amino]-acetic acid (20.0 mg, 81 µmol) in CH₂Cl₂ (5 mL) at 25° C. was treated with HATU (30.8 mg, 81 µmol). N,N-Diisopropylethylamine (20.9 mg, 162 µmol) was added to the solution. The reaction mixture was stirred for 2 h. The reaction mixture was then poured into 0.2M aqueous KHSO₄ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-[3-(5-trifluoromethyl-pyridin-2-yl)-benzyl]-acetamide (20.5 mg, 53%) as a white solid. MH+=482.1.

Example 42

2-[Ethyl-(4-fluoro-benzenesulfonyl)-amino]-N-[3-(5-trifluoromethyl-pyridin-2-yl)-benzyl]-acetamide

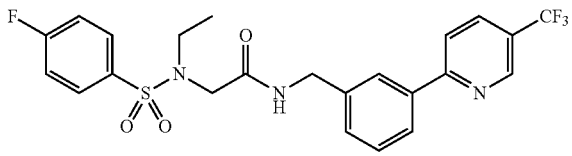 [SMILES: CCN(CC(=O)NCc1cccc(-c2ccc(C(F)(F)F)cn2)c1)S(=O)(=O)c1ccc(F)cc1]

A solution of 3-(5-trifluoromethyl-pyridin-2-yl)-benzylamine (19.3 mg, 77 µmol) and [ethyl-(4-fluoro-benzenesulfonyl)-amino]-acetic acid (20.0 mg, 77 µmol) in CH₂Cl₂ (5 mL) at 25° C. was treated with HATU (29.1 mg, 77 µmol). N,N-Diisopropylethylamine (19.8 mg, 154 µmol) was added to the solution. The reaction mixture was stirred for 2 h. The reaction mixture was then poured into 0.2M aqueous KHSO₄ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-[3-(5-trifluoromethyl-pyridin-2-yl)-benzyl]-acetamide (31.7 mg, 84%) as a white solid. MH+=496.1.

Example 43

2-[(4-Fluoro-benzenesulfonyl)-methyl-amino]-N-(5-methoxy-4'-trifluoromethyl-biphenyl-3-ylmethyl)-acetamide

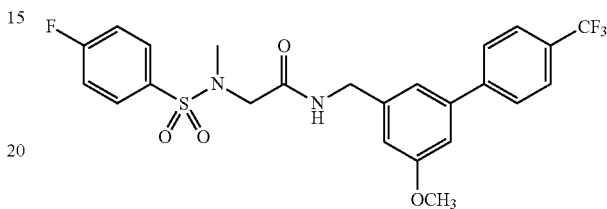

A solution of 4,4,5,5-tetramethyl-2-(4-trifluoromethyl-phenyl-[1,3,2]dioxaborolane (1.00 g, 3.68 mmol), 3-bromo-5-methoxy-benzonitrile (0.78 g, 3.68 mmol) and potassium carbonate (0.51 g, 3.68 mmol) in DMF (5 mL) at 25° C. was purged with nitrogen gas and evacuated three times. The solution was then treated with tetrakis(triphenylphosphine)palladium(0) (212 mg, 184 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 5-methoxy-4'-trifluoromethyl-biphenyl-3-carbonitrile (0.70 g, 69%) as a white solid.

A solution of 5-methoxy-4'-trifluoromethyl-biphenyl-3-carbonitrile (0.70 g, 2.52 mmol), and 10% palladium on carbon (134 mg, 0.126 mmol) in ethanol (10 mL) at 25° C. was stirred under 50 psi hydrogen pressure for 3 h. Filtration followed by concentration in vacuo gave C-(5-methoxy-4'-trifluoromethyl-biphenyl-3-yl)-methylamine (500 mg, 70%) as a brown oil. M+H=281.9.

A solution of C-(5-methoxy-4'-trifluoromethyl-biphenyl-3-yl)-methylamine (22.8 mg, 81 µmol) and [(4-fluoro-benzenesulfonyl)-methyl-amino]-acetic acid (20 mg, 81 µmol) in CH₂Cl₂ (5 mL) at 25° C. was treated with HATU (30.8 mg, 81 µmol). N,N-diisopropyl-ethylamine (20.9 mg, 162 µmol) was added to the solution. The reaction mixture was stirred for 2 h. The reaction mixture was then poured into 0.2M aqueous KHSO₄ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-methyl-amino]-N-(5-methoxy-4'-trifluoromethyl-biphenyl-3-ylmethyl)-acetamide (19.2 mg, 47%) as a white solid. MH+=510.9.

Example 44

2-[Ethyl-(4-fluoro-benzenesulfonyl)-amino]-N-(5-methoxy-4'-trifluoromethyl-biphenyl-3-ylmethyl)-acetamide

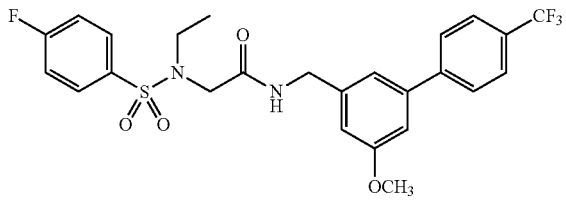 [SMILES: CCN(CC(=O)NCc1cc(OC)cc(-c2ccc(C(F)(F)F)cc2)c1)S(=O)(=O)c1ccc(F)cc1]

A solution of C-(5-methoxy-4'-trifluoromethyl-biphenyl-3-yl)-methylamine (21.5 mg, 77 μmol) and [ethyl-(4-fluoro-benzenesulfonyl)-amino]-acetic acid (20 mg, 77 μmol) in CH$_2$Cl$_2$ (5 mL) at 25° C. was treated with HATU (29.1 mg, 77 μmol). N,N-Diisopropylethylamine (19.8 mg, 154 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(5-methoxy-4'-trifluoromethyl-biphenyl-3-ylmethyl)-acetamide (18.8 mg, 47%) as a white solid. MH+=525.0.

Example 45

2-[(4-Fluoro-benzenesulfonyl)-isopropyl-amino]-N-(5-methoxy-4'-trifluoromethyl-biphenyl-3-ylmethyl)-acetamide

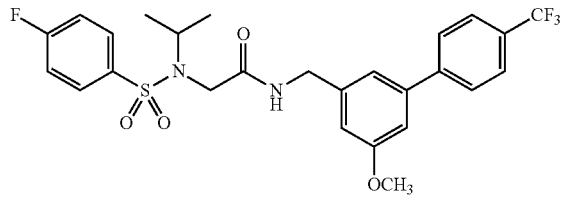 [SMILES: COc1cc(CNC(=O)CN(C(C)C)S(=O)(=O)c2ccc(F)cc2)cc(-c2ccc(C(F)(F)F)cc2)c1]

A solution of C-(5-methoxy-4'-trifluoromethyl-biphenyl-3-yl)-methylamine (20.4 mg, 73 μmol) and [(4-fluoro-benzenesulfonyl)-isopropyl-amino]-acetic acid (20 mg, 73 μmol) in CH$_2$Cl$_2$ (5 mL) at 25° C. was treated with HATU (27.6 mg, 73 μmol). N,N-Diisopropylethylamine (18.8 mg, 146 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(5-methoxy-4'-trifluoromethyl-biphenyl-3-ylmethyl)-acetamide (25.3 mg, 65%) as a white solid. MH+=539.0.

Example 46

2-[Ethyl-(4-fluoro-benzenesulfonyl)-amino]-N-(6-methoxy-4'-trifluoromethyl-biphenyl-3-ylmethyl)-acetamide

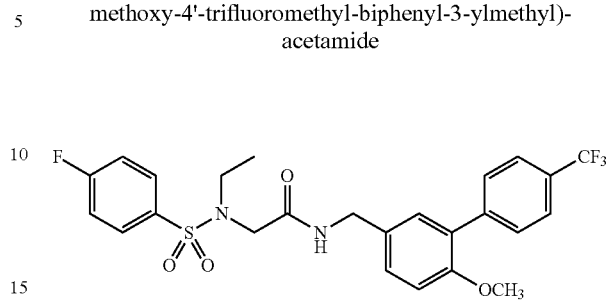

A solution of 4,4,5,5-tetramethyl-2-(4-trifluoromethyl-phenyl)-[1,3,2]dioxaborolane (1.00 g, 3.68 mmol), 3-bromo-4-methoxy-benzonitrile (0.78 g, 3.68 mmol) and potassium carbonate (0.51 g, 3.68 mmol) in DMF (5 mL) at 25° C. was purged with nitrogen gas and evacuated three times. The solution was then treated with tetrakis(triphenylphosphine)palladium(0) (212 mg, 184 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 6-methoxy-4'-trifluoromethyl-biphenyl-3-carbonitrile (0.80 g, 79%) as a white solid.

A solution of 6-methoxy-4'-trifluoromethyl-biphenyl-3-carbonitrile (0.70 g, 2.52 mmol), and 10% palladium on carbon (134 mg, 0.126 mmol) in ethanol (10 mL) at 25° C. was stirred under 50 psi hydrogen pressure for 3 h. Filtration followed by concentration in vacuo gave C-(6-methoxy-4'-trifluoromethyl-biphenyl-3-yl)-methylamine (500 mg, 70%) as a brown oil. M+H=281.9.

A solution of C-(6-methoxy-4'-trifluoromethyl-biphenyl-3-yl)-methylamine (32.3 mg, 115 μmol) and [ethyl-(4-fluoro-benzenesulfonyl)-amino]-acetic acid (30 mg, 115 μmol) in CH$_2$Cl$_2$ (5 mL) at 25° C. was treated with HATU (43.7 mg, 115 μmol). N,N-Diisopropylethylamine (29.7 mg, 230 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[ethyl-(4-fluoro-benzenesulfonyl)-amino]-N-(6-methoxy-4'-trifluoromethyl-biphenyl-3-ylmethyl)-acetamide (16.2 mg, 27%) as a white solid. MH+=525.1.

Example 47

2-[(4-Fluoro-benzenesulfonyl)-isopropyl-amino]-N-(6-methoxy-4'-trifluoromethyl-biphenyl-3-ylmethyl)-acetamide

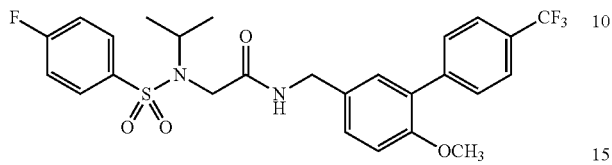

A solution of C-(6-methoxy-4'-trifluoromethyl-biphenyl-3-yl)-methylamine from Example 46 (81.7 mg, 291 µmol) and [(4-fluoro-benzenesulfonyl)-isopropyl-amino]-acetic acid (80 mg, 291 µmol) in $CH_2Cl_2$ (5 mL) at 25° C. was treated with HATU (110 mg, 291 µmol). N,N-Diisopropylethylamine (75.1 mg, 581 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(6-methoxy-4'-trifluoromethyl-biphenyl-3-ylmethyl)-acetamide (34.2 mg, 22%) as a white solid. MH+=539.0.

Example 48

2-[(3-Fluoro-benzenesulfonyl)-isopropyl-amino]-N-(4'-trifluoromethyl-biphenyl-3-ylmethyl)-acetamide

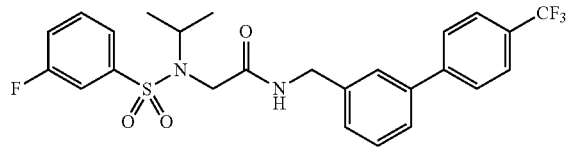 [SMILES: CC(C)N(CC(=O)NCc1cccc(-c2ccc(C(F)(F)F)cc2)c1)S(=O)(=O)c1cccc(F)c1]

A solution of C-(4'-trifluoromethyl-biphenyl-3-yl)-methylamine from Example 1 (27.4 mg, 109 µmol) and [(3-fluoro-benzenesulfonyl)-isopropyl-amino]-acetic acid (30 mg, 109 µmol) in $CH_2Cl_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(3-fluoro-benzenesulfonyl)-isopropyl-amino]-N-(4'-trifluoromethyl-biphenyl-3-ylmethyl)-acetamide (43.8 mg, 79%) as a white solid. MH+=509.2.

Example 49

2-[(3-Fluoro-benzenesulfonyl)-isopropyl-amino]-N-[6-(4-trifluoromethyl-phenyl)-pyrimidin-4-ylmethyl]-acetamide

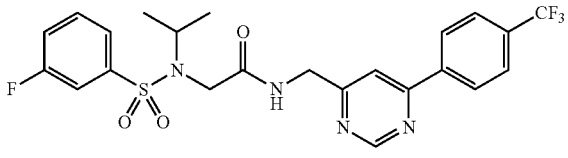 [SMILES: CC(C)N(CC(=O)NCc1cc(-c2ccc(C(F)(F)F)cc2)ncn1)S(=O)(=O)c1cccc(F)c1]

A solution of C-[6-(4-trifluoromethyl-phenyl)-pyrimidin-4-yl]-methylamine from Example 21 (27.6 mg, 109 µmol) and [(3-fluoro-benzenesulfonyl)-isopropyl-amino]-acetic acid (30 mg, 109 µmol) in $CH_2Cl_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(3-fluoro-benzenesulfonyl)-isopropyl-amino]-N-[6-(4-trifluoromethyl-phenyl)-pyrimidin-4-ylmethyl]-acetamide (21.8 mg, 39%) as a white solid. MH+=511.1.

Example 50

2-[(3-Fluoro-benzenesulfonyl)-isopropyl-amino]-N-[3-(5-trifluoromethyl-pyridin-2-yl)-benzyl]-acetamide

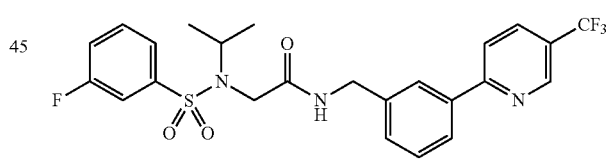

A solution of 3-(5-trifluoromethyl-pyridin-2-yl)-benzylamine from Example 43 (27.5 mg, 109 µmol) and [(3-fluoro-benzenesulfonyl)-isopropyl-amino]-acetic acid (30 mg, 109 µmol) in $CH_2Cl_2$ (5 mL) at 25° C. was treated with HATU (41.7 mg, 109 µmol). N,N-Diisopropylethylamine (28.2 mg, 218 µmol) was added to the solution. The reaction mixture was stirred for 2 h. The reaction mixture was then poured into 0.2M aqueous $KHSO_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(3-fluoro-benzenesulfonyl)-isopropyl-amino]-N-[3-(5-trifluoromethyl-pyridin-2-yl)-benzyl]-acetamide (26.1 mg, 47%) as a white solid. MH+=510.2.

Example 51

2-[(4-Fluoro-benzenesulfonyl)-methyl-amino]-3-hydroxy-N-(4'-trifluoromethyl-biphenyl-3-ylmethyl)-propionamide

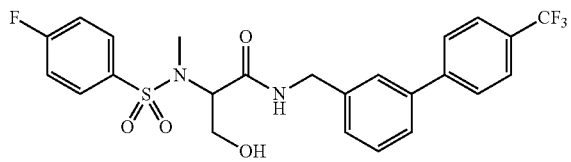 [SMILES: CN(C(CO)C(=O)NCc1cccc(-c2ccc(C(F)(F)F)cc2)c1)S(=O)(=O)c1ccc(F)cc1]

2-[(4-Fluoro-benzenesulfonyl)-methyl-amino]-3-hydroxy-N-(4'-trifluoromethyl-biphenyl-3-ylmethyl)-propionamide was prepared using 2-(tert-butoxycarbonyl-methyl-amino)-3-hydroxy-propionic acid according to the methods described for Example 2. MH+=510.9

Example 52

(S)-2-[(4-Fluoro-benzenesulfonyl)-methyl-amino]-3-methoxy-N-(4'-trifluoromethyl-biphenyl-3-ylmethyl)-propionamide

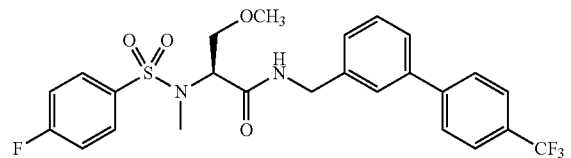 [SMILES: COC[C@@H](C(=O)NCc1cccc(-c2ccc(C(F)(F)F)cc2)c1)N(C)S(=O)(=O)c1ccc(F)cc1]

A solution of (4'-trifluoromethyl-biphenyl-3-yl)-methylamine from Example 1 (229 mg, 912 μmol) and (S)-2-tert-butoxycarbonylamino-3-methoxy-propionic acid (200 mg, 912 μmol) and N,N-diisopropylethylamine (478 μL, 2.74 mmol) in DMF (6 mL) at 25° C. was treated with HATU (694 mg, 1.82 mmol). The reaction mixture was stirred for 14 h. The reaction mixture was then poured into saturated, aqueous NH₄Cl and extracted three times with ethyl acetate. The combined organic layers were washed twice with water and once with brine. The organic layer was then dried over magnesium sulfate, filtered and concentrated in vacuo. Flash chromatography (50/50 hexanes/ethyl acetate) afforded (S)-2-tert-butoxycarbonylamino-3-methoxy-propionic acid 4'-trifluoromethyl-biphenyl-3-ylmethyl ester (260 mg) as a heavy oil. MH+=453.0

(S)-2-tert-Butoxycarbonylamino-3-methoxy-propionic acid 4'-trifluoromethyl-biphenyl-3-ylmethyl ester which was dissolved in 50/50 CH₂Cl₂/trifluoroacetic acid (6 mL). The resulting solution was stirred for 1 h after which all volatiles were removed under reduced pressure. The resulting residue was suspended in 0.1 M aqueous NaOH solution and the suspension was extracted three times with CH₂Cl₂. The combined organic layers were dried over anhydrous sodium sulfate, filtered and concentrated in vacuo to yield a heavy oil which was dissolved in CH₂Cl₂ and treated with N,N-diisopropylethylamine (197 μL, 1.13 mmol) and 4-fluorobenzenesulfonyl chloride (110 mg, 564 μmol). The reaction mixture was stirred at 25° C. for 3 hours after which all volatiles were removed under reduced pressure. (S)-2-(4-Fluorobenzenesulfonylamino)-3-methoxy-propionic acid 4'-trifluoromethyl-biphenyl-3-ylmethyl ester (181 mg, 63%) was isolated by chromatography (30-50% ethyl acetate in hexanes).

A solution of (S)-2-(4-fluorobenzenesulfonylamino)-3-methoxy-N-(4'-trifluoromethyl-biphenyl-3-ylmethyl)-propionamide (155 mg, 304 μmol) in DMF (3 mL) was treated with potassium carbonate (126 mg, 911 μmol) and iodomethane (21 μL, 334 μmol). After 14 h, the reaction mixture was poured into saturated, aqueous NH₄Cl and extracted three times with ethyl acetate. The combined organic layers were washed twice with water and once with brine. The combined organic phases were dried over MgSO₄, filtered and all volatiles were removed under reduced pressure. (S)-2-[(4-Fluoro-benzenesulfonyl)-methyl-amino]-3-methoxy-N-(4'-trifluoromethyl-biphenyl-3-ylmethyl)-propionamide (142 mg, 89%) was isolated by flash chromatography (50/50 ethyl acetate/hexanes) as a white foam. MH+=525.1

Example 53

2-(Benzenesulfonyl-isopropyl-amino)-N-(4'-trifluoromethyl-biphenyl-3-ylmethyl)-acetamide

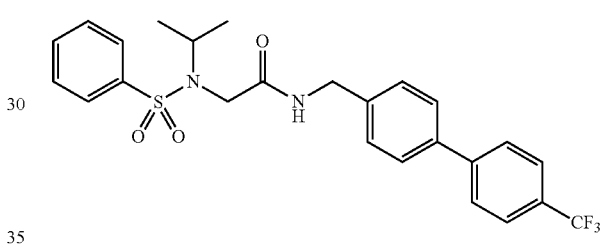

A solution of triethylamine (7.8 ml, 56 mmol) and isopropylamine (3.5 g, 46.6 mmol) were combined in THF (150 ml) and cooled with mechanical stirring to 5° C. Bromoacetic acid tert-butyl ester (7.84 g, 51.3 mmol) in THF (50 ml) was added over 1 h and stirred for an additional 3 h at 15° C. The suspension was filtered through celite and concentrated in vacuo. The residue was purified by flash chromatography (ethyl acetate to 10% methanol/CH₂Cl₂) to afford isopropylamino-acetic acid tert-butyl ester. $^1$H NMR (400 MHz, CDCl₃) δ=3.37 (s, 2H), 2.82 (m, 1H), 1.49 (s, 9H), 1.09 (d, 6H) ppm.

A solution of isopropylamino-acetic acid tert-butyl ester (400 mg, 2.31 mmol) and triethylamine (645 ul, 24 mmol) in CH₂Cl₂ (10 ml) was treated with benzenesulfonyl chloride (450 mg, 2.54 mmol) in CH₂Cl₂ (10 ml) and stirred for 4 h at 20° C. The suspension was filtered through celite and concentrated in vacuo. The residue was purified by flash chromatography (10-40% ethyl acetate/hexane) to afford (benzenesulfonyl-isopropyl-amino)-acetic acid tert-butyl ester as an oil. $^1$H NMR (400 MHz, CDCl₃) δ=7.6-7.9 (m, 5H), 3.92 (s, 2H) 3.90 (m, 1H), 1.44 (s, 9H), 0.96 (d, 6H) ppm.

A solution of (benzenesulfonyl-isopropyl-amino)-acetic acid tert-butyl ester (300 mg, 1.0 mmol) in dioxane (3 ml) was treated with 4.0 M HCl/dioxane (1.2 ml, 4.8 mmol) and stirred for 14 h. This was concentrated in vacuo to afford (benzenesulfonyl-isopropyl-amino)-acetic acid as a white solid. $^1$H NMR (400 MHz, DMSO$_{d6}$) δ=7.60-7.92 (m, 5H), 3.93 (s, 2H), 3.88 (m, 1H), 0.96 (d, 6H) ppm.

A solution of (benzenesulfonyl-isopropyl-amino)-acetic acid (50 mg, 1.94 mmol) in CH₂Cl₂ (8 ml) was combined with HATU (110 mg, 2.89 mmol) and Hünig's base (41 ul, 2.33 mmol). This was followed by (4'-trifluoromethyl-biphenyl-3-yl)-methylamine from Example 1 (40 mg, 1.79 mmol). The solution was stirred at ambient for 16 hr and concentrated in vacuo. The residue was purified by flash chromatography (25-50% ethyl acetate/hexane) to afford 2-benzenesulfonyl-isopropyl-amino)-N-(4'-trifluoromethyl-biphenyl-3-ylmethyl)-acetamide as a white solid. MH+=491.

Example 54

2-[(4-Fluoro-benzenesulfonyl)-oxetan-3-ylmethyl-amino]-N-(4'-trifluoron-3-ylmethyl-amino]-N-(4'-trifluoro methyl-biphenyl-3-ylmethyl)-acetamide

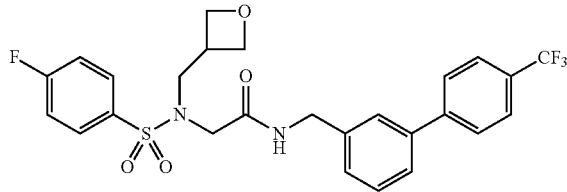 [SMILES: O=C(CN(CC1COC1)S(=O)(=O)c1ccc(F)cc1)NCc1cccc(-c2ccc(C(F)(F)F)cc2)c1]

A solution of oxetan-3-yl-methanol (500 mg, 5.68 mmol) in pyridine (5 ml) was treated with p-toluene sulfonylchloride (1.2 g, 6.3 mmol and stirred for 4 h at ambient. The solution was diluted with a solution (50 ml) of 50% ethyl acetate/hexane and filtered. The solution was concentrated in vacuo and washed with 1 N HCl, brine, dried (MgSO$_4$) and concentrated in vacuo to afford toluene-4-sulfonic acid oxetan-3-yl methyl ester as an oil. $^1$H NMR (400 MHz, CDCl$_3$) δ=7.73 (d, 2H), 7.38 (d, 2H), 4.68 (t, 2H), 4.24 (t, 2H), 4.18 (d, 2H), 3.22 (m, 1H), 2.41 (s, 3H) ppm.

A solution of toluene-4-sulfonic acid oxetan-3-yl methyl ester (500 mg, 2.2 mmol) and amino-acetic acid methyl ester hydrochloride (950 mg, 7.6 mmol) in acetonitrile (10 ml) was combined with NaHCO$_3$ (1.32 g, 15.8 mmol) and stirred at 50-55° C. for 16 h. The mixture was diluted with ether and filtered through Celite) and concentrated in vacuo. This crude material was purified by flash chromatography (ethyl acetate then 10% methanol/CH$_2$Cl$_2$) to afford [(oxetan-3-ylmethyl)-amino]-acetic acid methyl ester an oil. $^1$H NMR (400 MHz, CDCl$_3$) δ=4.75 (t, 2H), 4.45 (t, 2H), 3.78 (s, 3H), 3.48 (d, 2H), 3.12 (M, 1H) ppm.

A solution of [(oxetan-3-ylmethyl)-amino]-acetic acid methyl ester (150 mg, 9.42 mmol), 4-fluoro-benzenesulfonyl chloride (238 mg, 1.23 mmol), Hünig's base (500 μl, 28.5 mmol), DMAP (57.6 mg, 4.7 mmol) in CH$_2$Cl$_2$ (20 ml) was stirred at ambient for 4 h. Solvent was concentrated in vacuo and purification was by flash chromatography (60-100% ethyl acetate/hexane) to afford [(4-fluoro-benzenesulfonyl)-oxetan-3-ylmethyl-amino]-acetic acid methyl ester as a solid. $^1$H NMR (400 MHz, DMSO$_{d6}$) δ=7.93 (m, 2H), 7.47 (t, 2H), 4.53 (t, 2H), 4.22 (t, 2H), 4.16 (s, 2H), 3.48 (d, 2H), 3.31 (s, 3H), 3.17 (m, 1H) ppm.

A solution of [(4-fluoro-benzenesulfonyl)-oxetan-3-ylmethyl-amino]-acetic acid methyl ester (100 mg, 3.15 mmol) was dissolved in dioxane (7 ml). This solution was combined with a solution of potassium hydroxide (100 mg, 18.8 mmol) dissolved in water (4 ml). This was stirred at ambient for 3 h and the solvent was concentrated in vacuo to 3 ml. The solution was diluted with water (15 ml) and acidified with 2N H$_3$PO$_4$ followed by extraction with CH$_2$Cl$_2$. The CH$_2$Cl$_2$ solution was dried (MgSO$_4$) and concentrated in vacuo to afford solid [(4-fluoro-benzenesulfonyl)-oxetan-3-ylmethyl-amino]-acetic acid. MH-=302.

A solution of [(4-fluoro-benzenesulfonyl)-oxetan-3-ylmethyl-amino]-acetic acid (80 mg, 2.64 mmol) was dissolved in CH$_2$Cl$_2$ (15 ml). HATU (191 mg, 5.0 mmol) and Hunig's base (92 μl, 5.3 mmol) was added and the solution stirred for 5 minutes. This was added followed by (4'-trifluoromethyl-biphenyl-3-yl)-methylamine from Example 1 (66.3 mg, 2.64 mmol). This was stirred at ambient for 16 hr and concentrated in vacuo. The residue was purified by flash chromatography (60-90% ethyl acetate/hexane) to afford 2-[(4-fluoro-benzenesulfonyl)-oxetan-3-ylmethyl-amino]-N-(4'-trifluoron-3-ylmethyl-amino]-N-(4'-trifluoro methyl-biphenyl-3-ylmethyl)-acetamide as a white solid. MH-=535.

Example 55

2-[(4-Fluoro-benzenesulfonyl)-isopropyl-amino]-N-(6-trifluoromethyl-[3,4']bipyridinyl-2'-ylmethyl)-acetamide

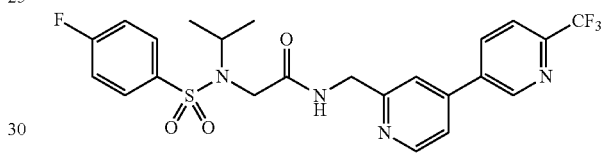

A solution of 6-(trifluoromethyl)pyridine-3-ylboronic acid (1.04 g, 5.46 mmol), 4-bromo-pyridine-2-carbonitrile (1.00 g, 5.46 mmol) and potassium carbonate (0.76 g, 5.46 mmol) in DMF (5 mL) at 25° C. was purged with nitrogen gas and evacuated three times. The solution was then treated with tetrakis(triphenylphosphine)palladium(0) (316 mg, 273 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 6-trifluoromethyl-[3,4']bipyridinyl-2'-carbonitrile (0.90 g, 66%) as a white solid. MH+=249.9.

A solution of 6-trifluoromethyl-[3,4']bipyridinyl-2'-carbonitrile (0.90 g, 3.61 mmol), and 10% palladium on carbon (192 mg, 0.181 mmol) in ethanol (10 mL) at 25° C. was stirred under 50 psi hydrogen pressure for 3 h. Filtration followed by concentration in vacuo gave C-(6-trifluoromethyl-[3,4']bipyridinyl-2'-yl)-methylamine (600 mg, 66%) as a brown oil. MH+=253.9.

A solution of C-(6-trifluoromethyl-[3,4']bipyridinyl-2'-yl)-methylamine (27.6 mg, 109 μmol) and [(4-fluoro-benzenesulfonyl)-isopropyl-amino]-acetic acid (30 mg, 109 μmol) in CH$_2$Cl$_2$ (5 mL) at 25° C. was treated with HATU (41.4 mg, 109 μmol). N,N-Diisopropylethylamine (28.2 mg, 218 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-(6-trifluoromethyl-[3,4]bipyridi-nyl-2'-ylmethyl)-acetamide (25.4 mg, 46%) as a white solid. MH+=511.1.

Example 56

2-[Isopropyl-(pyridine-3-sulfonyl)-amino]-N-[6-(4-trifluoromethyl-phenyl)-pyrimidin-4-ylmethyl]-acetamide

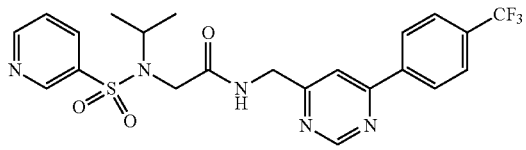 [SMILES: CC(C)N(CC(=O)NCc1cc(-c2ccc(C(F)(F)F)cc2)ncn1)S(=O)(=O)c1cccnc1]

To a solution of 2-(tert-butoxycarbonyl(isopropyl)amino) acetic acid (660 mg, 3.04 mmol), [6-(4-trifluoromethyl-phenyl)-pyrimidin-4-yl]-methylamine hydrochloride from Example 21 (800 mg, 2.76 mmol), 1-hydroxybenzotriazole hydrate (465 mg, 3.04 mmol) and N,N-diisopropylethylamine (1.93 mL, 11.0 mmol) in DMF (15 mL) was added HBTU (1.15 g, 3.04 mmol). The reaction mixture was stirred for 2 h. Ethyl acetate was added. The organic layer was washed with 1 M citric acid, brine, saturated sodium carbonate and brine, dried over anhydrous sodium sulfate, filtered and concentrated in vacuo. Flash chromatography (50/50 to 0/100 hexanes/ethyl acetate) afforded isopropyl-({[6-(4-trifluoromethyl-phenyl)-pyrimidin-4-ylmethyl]-carbamoyl}-methyl)-carbamic acid tert-butyl ester (900 mg, 72%) as a white solid. MH+=453.

A solution of isopropyl-({[6-(4-trifluoromethyl-phenyl)-pyrimidin-4-ylmethyl]-carbamoyl}-methyl)-carbamic acid tert-butyl ester (800 mg, 1.77 mmol) in 4M HCl in dioxane (20 mL, 80.1 mmol) was stirred at room temperature for 2 h. After removal of the solvent by rotary evaporator, water was added. The water layer was neutralized with saturated sodium carbonate and extracted with ethyl acetate. The organic layer was washed with saturated sodium carbonate, brine, dried over anhydrous sodium sulfate, filtered and concentrated in vacuo to give 2-isopropylamino-N-[6-(4-trifluoromethyl-phenyl)-pyrimidin-4-ylmethyl]-acetamide (630 mg, 101%) as a light yellow solid. MH+=353.

To a solution of 2-(isopropylamino)-N-((6-(4-(trifluoromethyl)phenyl)pyrimidin-4-yl)methyl)acetamide (30 mg, 85.1 μmol) and N,N-diisopropylethylamine (44.6 μL, 255 μmol) in CH$_2$Cl$_2$ (3 ml) were added pyridine-3-sulfonyl chloride (15.1 mg, 85.1 μmol). It was stirred at room temperature overnight. Ethyl acetate was added. The organic layer was washed with saturated sodium carbonate and brine, dried over anhydrous sodium sulfate, filtered and concentrated in vacuo. Flash chromatography (ethyl acetate) afforded 2-[isopropyl-(pyridine-3-sulfonyl)-amino]-N-[6-(4-trifluoromethyl-phenyl)-pyrimidin-4-ylmethyl]-acetamide (27 mg, 64%) as a white solid. MH+=494.

Example 57

2-[(4-Fluoro-benzenesulfonyl)-isopropyl-amino]-N-[5-(4-trifluoromethyl-phenyl)-pyridin-3-ylmethyl]-acetamide

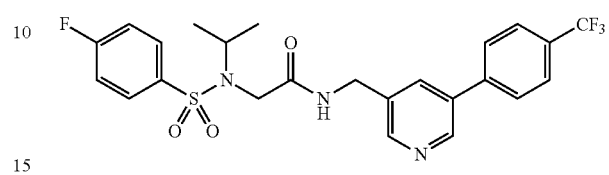

A solution of 4,4,5,5-tetramethyl-2-(4-trifluoromethyl-phenyl)-[1,3,2]dioxaborolane (743 mg, 2.73 mmol), 5-bromo-nicotinonitrile (500 mg, 2.73 mmol) and potassium carbonate (358 mg, 2.73 mmol) in DMF (5 mL) at 25° C. was purged with nitrogen gas and evacuated three times. The solution was then treated with tetrakis(triphenylphosphine)palladium(0) (158 mg, 137 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 5-(4-trifluoromethyl-phenyl)-nicotinonitrile (0.48 g, 71%) as a white solid. MH+=248.9.

A solution of 5-(4-trifluoromethyl-phenyl)-nicotinonitrile (0.48 g, 1.93 mmol), and 10% palladium on carbon (103 mg, 0.097 mmol) in ethanol (10 mL) at 25° C. was stirred under 50 psi hydrogen pressure for 3 h. Filtration followed by concentration in vacuo gave C-[5-(4-trifluoromethyl-phenyl)-pyridin-3-yl]-methylamine (360 mg, 74%) as a brown oil. M+H=252.9.

A solution of C-[5-(4-trifluoromethyl-phenyl)-pyridin-3-yl]-methylamine (27.5 mg, 109 μmol) and [(4-fluoro-benzenesulfonyl)-isopropyl-amino]-acetic acid (30 mg, 109 μmol) in CH$_2$Cl$_2$ (5 mL) at 25° C. was treated with HATU (41.4 mg, 109 μmol). N,N-Diisopropylethylamine (28.2 mg, 218 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[5-(4-trifluoromethyl-phenyl)-pyridin-3-ylmethyl]-acetamide (30.7 mg, 55%) as a white solid. MH+=509.9.

Example 58

2-[(4-Fluoro-benzenesulfonyl)-isopropyl-amino]-N-(6'-trifluoromethyl-[2,3']bipyridinyl-4-ylmethyl)-acetamide

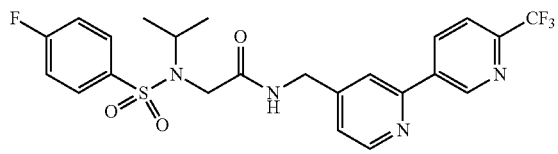 [SMILES: CC(C)N(CC(=O)NCc1ccnc(-c2ccc(C(F)(F)F)nc2)c1)S(=O)(=O)c1ccc(F)cc1]

2-Chloroisonicotinonitrile (1.89 g, 13.7 mmol), 6-(trifluoromethyl)pyridin-3-ylboronic acid (2.9 g, 15.2 mmol) and potassium carbonate (4.2 g, 30.4 mmol) dissolved in 60 ml water were combined with butanol (60 ml) and sparged for 10 min with nitrogen.

Bis(triphenylphosphine)palladium(II)dichloride (533 mg, 759 μmol) was added and the mixture was stirred at 85° C. for 3 h. The organic layer was separated, washed with brine and concentrated in vacuo. The residue was purified by flash chromatography (40% ethyl acetate/hexane) to afford 6'-trifluoromethyl-[2,3']bipyridinyl-4-carbonitrile. MH+=250.

A solution of 6'-trifluoromethyl-[2,3']bipyridinyl-4-carbonitrile (100 mg, 4.0 mmol) in ethanol (20 mL) was treated with 5% palladium on carbon (43 mg). This was hydrogenated in a Parr shaker at 50 psi and 25° C. for 2 h. Filtration and concentration in vacuo afforded (6'-trifluoromethyl-[2,3']bipyridinyl-4-yl)-methylamine. $^1$H NMR (400 MHz, DMSO$_{d6}$) δ=9.43 (d, 1H), 8.76 (d, 1H), 8.68 (d, 1H), 8.09 (m, 1H), 8.03 (d, 1H), 7.47 (d, 1H), 3.86 (s, 2H) ppm.

A solution of [(4-fluoro-benzenesulfonyl)-isopropyl-amino]-acetic acid in CH$_2$Cl$_2$ (8 ml) was combined with HATU (137 mg, 3.6 mmol) and Hünig's base (105 ul, 6.0 mmol) and stirred for 5 min. This was followed by (6'-trifluoromethyl-[2,3']bipyridinyl-4-yl)-methylamine (51 mg, 2.0 mmol). The solution was stirred at 25° C. for 16 hr and concentrated in vacuo. The residue was purified by flash chromatography (80-100% ethyl acetate/hexane) to afford 2-[(4-fluoro-benzenesulfonyl)-isopropyl-amino]-N-(6'-trifluoromethyl-[2,3']bipyridinyl-4-ylmethyl)-acetamide. MH+=511.

Example 59

2-[(3-Fluoro-benzenesulfonyl)-isopropyl-amino]-N-[2-(4-trifluoromethyl-phenyl)-pyridin-4-ylmethyl]-acetamide

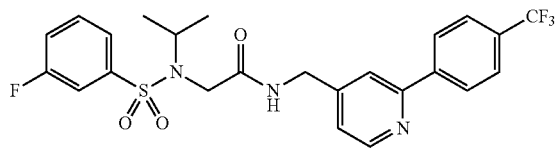 [SMILES: CC(C)N(CC(=O)NCc1ccnc(-c2ccc(C(F)(F)F)cc2)c1)S(=O)(=O)c1cccc(F)c1]

A solution of 4-(trifluoromethyl)phenylboronic acid (519 mg, 2.73 mmol), 2-bromo-isonicotinonitrile (500 mg, 2.73 mmol) and potassium carbonate (358 mg, 2.73 mmol) in DMF (5 mL) at 25° C. was purged with nitrogen gas and evacuated three times. The solution was then treated with tetrakis(triphenylphosphine)palladium(0) (158 mg, 137 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded 2-(4-trifluoromethyl-phenyl)-isonicotinonitrile (0.38 g, 56%) as a white solid. MH+=248.9

A solution of 2-(4-trifluoromethyl-phenyl)-isonicotinonitrile (0.38 g, 1.53 mmol), and 10% palladium on carbon (82 mg, 0.077 mmol) in ethanol (10 mL) at 25° C. was stirred under 50 psi hydrogen pressure for 3 h. Filtration followed by concentration in vacuo gave C-[2-(4-trifluoromethyl-phenyl)-pyridin-4-yl]-methylamine (250 mg, 65%) as a brown oil. MH+=252.9.

A solution of 3-(5-trifluoromethyl-pyridin-2-yl)-benzylamine (36.6 mg, 145 μmol) and [(3-fluoro-benzenesulfonyl)-isopropyl-amino]-acetic acid (40 mg, 145 μmol) in CH$_2$Cl$_2$ (5 mL) at 25° C. was treated with HATU (55.2 mg, 145 μmol). N,N-Diisopropylethylamine (37.6 mg, 291 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(3-fluoro-benzenesulfonyl)-isopropyl-amino]-N-[2-(4-trifluoromethyl-phenyl)-pyridin-4-ylmethyl]-acetamide (51.5 mg, 70%) as a white solid. MH+=510.0.

Example 60

2-[(4-Fluoro-benzenesulfonyl)-oxetan-3-yl-amino]-N-(4'-trifluoromethyl-biphenyl-3-ylmethyl)-acetamide

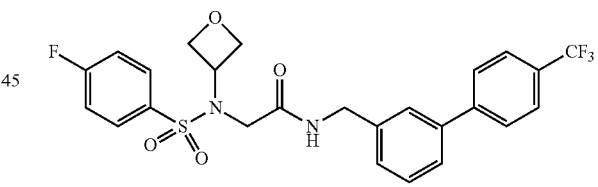

A solution of 2-bromo-N-(4'-trifluoromethyl-biphenyl-3-ylmethyl)-acetamide from Example 13 (55 mg, 1.5 mmol) and oxetan-3-amine (65 mg, 8.9 mmol) in a solution of THF (2 ml) was stirred for 14 hr at 25° C. This was diluted with ether, filtered through celite and concentrated in vacuo to afford 2-(oxetan-3-ylamino)-N-(4'-trifluoromethyl-biphenyl-3-ylmethyl)-acetamide. $^1$H NMR (400 MHz, DMSO$_{d6}$) δ=8.38 (t, 1H), 7.84 (q, 4H), 7.62 (m, 3H), 7.46 (t, 1H), 7.33 (d, 1H), 4.6 (m, 2H), 4.38 (d, 2H), 3.97 (m, 2H) 3.88 (m, 1H), 3.95 (d, 2H) ppm. MH+=365.

A solution of 2-(oxetan-3-ylamino)-N-(4'-trifluoromethyl-biphenyl-3-ylmethyl)-acetamide (50 mg, 1.4 mmol) and Hünig's base (120 uL, 6.9 mmol) in CH$_2$Cl$_2$ (8 ml) was combined with DMAP ((8.4 mg, 0.68 mmol) and 4-fluorobenzene-1-sulfonyl chloride (37 mg, 1.9 mmol) and stirred at 25° C. for 4 h. The solution was purified by flash chromatography (60% ethyl acetate/hexane) to afford 2-[(4- fluoro-benzenesulfonyl)-oxetan-3-yl-amino]-N-(4'-trifluoromethyl-biphenyl-3-ylmethyl)-acetamide as a white solid. MH+=523.

Example 61

2-[(4-Fluoro-benzenesulfonyl)-isopropyl-amino]-N-[6-(6-trifluoromethyl-pyridin-3-yl)-pyrimidin-4-ylmethyl]-acetamide

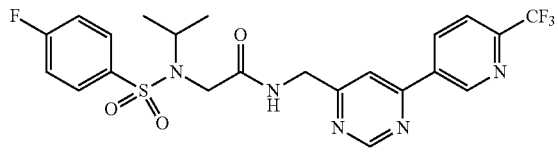

A solution of 6-(trifluoromethyl)-pyridin-3-ylboronic acid (Ark Pharm, Inc.) (2.54 g, 13.3 mmol) and 4,6-dichloropyrimidine (2.2 g, 14.4 mmol) in 15% ethanol/t-butanol (140 ml) was combined with a solution of potassium phosphate tribasic (6.27 g, 29.5 mmol) dissolved in water (60 ml) while sparging with $N_2$. Bis(triphenylphosphine)palladium(II)dichloride (622 mg, 886 µmol) was added and the well stirred mixture heated to 85° C. for 3 h and cooled. The organic phase was separated, diluted with ethyl ether (50 ml) and washed with 50% brine/water solution. The organics were dried ($MgSO_4$), filtered and concentrated in vacuo to give a solid. Mixtures of isomers were separated by flash chromatography (15-20% ethyl acetate/hexane) to afford 400 mg of 4-chloro-6-(6-trifluoromethyl-pyridin-3-yl)-pyrimidine as a solid. MH+=260.

A solution of 4-chloro-6-(6-trifluoromethyl-pyridin-3-yl)-pyrimidine (400 mg, 1.54 mmol) and triethylamine (312 mg, 3.1 mmol) in acetonitrile (10 ml) was combined with tetrabutylammonium cyanide (410 mg, 1.54 mmol) and brought to 75° C. for 1 h. This was cooled, diluted with ethyl ether and washed with 50% brine/water. The organics were dried ($MgSO_4$), filtered and concentrated in vacuo. The crude material was purified by flash chromatography (10% to 15% ethylacetate/hexane hexanes) to afford 6-(6-trifluoromethyl-pyridin-3-yl)-pyrimidine-4-carbonitrile. MH+=251.

A solution of 6-(6-trifluoromethyl-pyridin-3-yl)-pyrimidine-4-carbonitrile (100 mg, 0.4 mmol) was combined with 5% palladium on carbon (400 mg) in ethanol (20 ml). This was reduced at 50 psi of hydrogen in a Parr shaker over 4 h at 25° C. Filtration and concentration in vacuo afforded C-[6-(6-trifluoromethyl-pyridin-3-yl)-pyrimidin-4-yl]-methylamine as a solid. $^1$H NMR (400 MHz, $DMSO_{d6}$) δ=9.53 (s, 1H), 9.41 (s, 1H), 8.83 (d, 1H), 8.54 (s, 1H), 8.17 (d, 1H), 4.34 (m, 2H) ppm.

C-[6-(6-trifluoromethyl-pyridin-3-yl)-pyrimidin-4-yl]-methylamine (23 mg, 0.09 mmol) was coupled with 2-(4-fluoro-N-isopropylphenylsulfonamido)acetic acid (25 mg, 0.09 mmol) in a manner described in Example 58 to afford 2-[(4-fluoro-benzenesulfonyl)-isopropyl-amino]-N-[6-(6-trifluoromethyl-pyridin-3-yl)-pyrimidin-4-ylmethyl]-acetamide. MH+=512.

Example 62

2-[(4-Fluoro-benzenesulfonyl)-(2,2,2-trifluoroethyl)-amino]-N-(4'-trifluoromethyl-biphenyl-3-ylmethyl)-acetamide

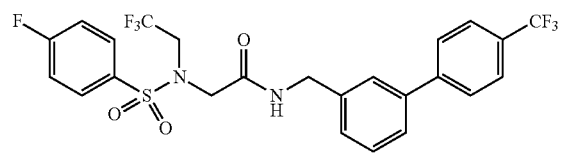 [SMILES: O=C(CN(CC(F)(F)F)S(=O)(=O)c1ccc(F)cc1)NCc1cccc(-c2ccc(C(F)(F)F)cc2)c1]

To a solution of (4'-(trifluoromethyl)biphenyl-3-yl)methanamine from Example 1 (500 mg, 1.99 mmol) and pyridine (644 µl, 7.96 mmol) in $CH_2Cl_2$ (25 mL) was added a solution of 2-bromoacetyl chloride (313 mg, 1.99 mmol) in $CH_2Cl_2$ (5 ml) at 5° C. The reaction mixture was stirred at 5° C. for 15 min and then at rt for 1 h. $CH_2Cl_2$ and water were added. The organic layer was washed with 2 N HCl, brine, dried over anhydrous sodium sulfate, filtered and concentrated in vacuo to give 2-bromo-N-((4'-(trifluoromethyl)biphenyl-3-yl)methyl)acetamide (690 mg, 89%) as a white solid which was directly used for next step without further purification. MH+=373.

To a solution of 2,2,2-trifluoroethylamine (373 mg, 3.77 mmol) in pyridine (5 mL) was added 4-fluorobenzene-1-sulfonyl chloride (734 mg, 3.77 mmol). The reaction mixture was stirred at room temperature for 12 h. After removal of solvent, water was added. pH was adjusted to acidic using 1N HCl. The product was extracted with ethyl acetate. The organic layer was washed with brine, dried over anhydrous sodium sulfate, filtered and concentrated in vacuo to give 4-fluoro-N-(2,2,2-trifluoroethyl)benzenesulfonamide (970 mg, 100%) as a white solid which was directly used for next step without further purification. MH−=256.

To a solution of 4-fluoro-N-(2,2,2-trifluoroethyl)benzenesulfonamide (30 mg, 117 µmol) and 2-bromo-N-((4'-(trifluoromethyl)biphenyl-3-yl)methyl)acetamide (43.4 mg, 117 µmol) in DMF (2 ml) was added cesium carbonate (114 mg, 350 µmol). The reaction mixture was stirred at room temperature for 12 h. Ethyl acetate and water were added. The organic layer was washed with 1 N HCl, brine, dried over anhydrous sodium sulfate, filtered and concentrated in vacuo. Flash chromatography (70/30 hexane/ethyl acetate) afforded 2-[(4-fluoro-benzenesulfonyl)-(2,2,2-trifluoroethyl)-amino]-N-(4'-trifluoromethyl-biphenyl-3-ylmethyl)-acetamide (56 mg, 88%) as a white solid. MH+=549.

Example 63

2-[(4-Fluoro-benzenesulfonyl)-isopropyl-amino]-N-[3-fluoro-5-(6-trifluoromethyl-pyridin-3-yl)-benzyl]-acetamide

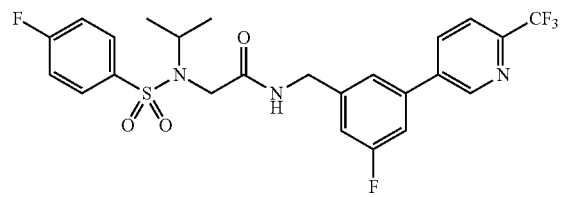 [SMILES: CC(C)N(CC(=O)NCc1cc(F)cc(-c2ccc(C(F)(F)F)nc2)c1)S(=O)(=O)c1ccc(F)cc1]

A solution of 5-(4,4,5,5-tetramethyl-1,3,2-dioxaborolan-2-yl)-2-(trifluoromethyl)pyridine (669 mg, 2.45 mmol), (3-bromo-5-fluorophenyl)methanamine (500 mg, 2.45 mmol) and potassium carbonate (0.34 g, 2.45 mmol) in DMF (5 mL) at 25° C. was purged with nitrogen gas and evacuated three times. The solution was then treated with tetrakis(triphenylphosphine)palladium(0) (142 mg, 123 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave 3-fluoro-5-(6-trifluoromethyl-pyridin-3-yl)-benzylamine (0.55 g, 83%) as a brown solid. M+H=270.8

A solution of 3-fluoro-5-(6-trifluoromethyl-pyridin-3-yl)-benzylamine (33.1 mg, 131 µmol) and [(4-fluoro-benzenesulfonyl)-isopropyl-amino]-acetic acid (30 mg, 109 µmol) in CH$_2$Cl$_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[3-fluoro-5-(6-trifluoromethyl-pyridin-3-yl)-benzyl]-acetamide (52.3 mg, 91%) as a white solid. MH+=528.0.

Example 64

2-[(6-Chloro-pyridine-3-sulfonyl)-isopropyl-amino]-N-[6-(4-trifluoromethyl-phenyl)-pyrimidin-4-ylmethyl]-acetamide

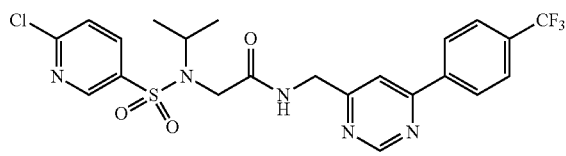 [SMILES: CC(C)N(CC(=O)NCc1cc(-c2ccc(C(F)(F)F)cc2)ncn1)S(=O)(=O)c1ccc(Cl)nc1]

To a solution of 2-(isopropylamino)-N-((6-(4-(trifluoromethyl)phenyl)pyrimidin-4-yl)methyl)acetamide (30 mg, 85.1 µmol) and N,N-diisopropylethylamine (44.6 µL, 255 µmol) in CH$_2$Cl$_2$ (3 ml) were added 6-chloropyridine-3-sulfonyl chloride (21.7 mg, 102 µmol). It was stirred at rt overnight. Ethyl acetate was added. The organic layer was washed with saturated sodium carbonate and brine, dried over anhydrous sodium sulfate, filtered and concentrated in vacuo. Flash chromatography (ethyl acetate) afforded 2-[(6-chloro-pyridine-3-sulfonyl)-isopropyl-amino]-N-[6-(4-trifluoromethyl-phenyl)-pyrimidin-4-ylmethyl]-acetamide (22 mg, 49%) as a white solid. MH+=528.

Example 65

2-[(2-Cyano-benzenesulfonyl)-isopropyl-amino]-N-[6-(4-trifluoromethyl-phenyl)-pyrimidin-4-ylmethyl]-acetamide

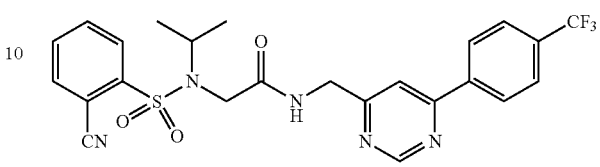

To a solution of 2-(isopropylamino)-N-((6-(4-(trifluoromethyl)phenyl)pyrimidin-4-yl)methyl)acetamide (30 mg, 85.1 µmol) and N,N-diisopropylethylamine (44.6 µL, 255 µmol) in CH$_2$Cl$_2$ (3 ml) were added 2-cyanobenzenesulfonyl chloride (20.6 mg, 102 µmol). It was stirred at room temperature overnight. Ethyl acetate was added. The organic layer was washed with saturated sodium carbonate and brine, dried over anhydrous sodium sulfate, filtered and concentrated in vacuo. Flash chromatography (ethyl acetate) afforded 2-[(2-cyano-benzenesulfonyl)-isopropyl-amino]-N-[6-(4-trifluoromethyl-phenyl)-pyrimidin-4-ylmethyl]-acetamide (30 mg, 68%) as a white solid. MH+=518.

Example 66

2-[(4-Fluoro-benzenesulfonyl)-isopropyl-amino]-N-[3-(6-trifluoromethyl-pyridazin-3-yl)-benzyl]-acetamide

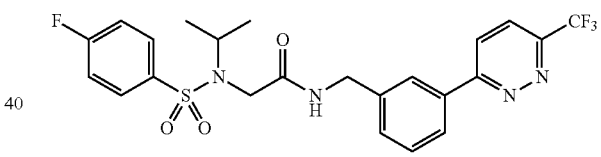

A solution of 3-[(tert-butoxycarbonylamino)methyl]phenylboronic acid (500 mg, 1.99 mmol), 3-chloro-6-(trifluormethyl)pyridazine (363 mg, 1.99 mmol) and potassium carbonate (0.28 g, 1.99 mmol) in DMF (5 mL) at 25° C. was purged with nitrogen gas and evacuated three times. The solution was then treated with tetrakis(triphenylphosphine)palladium(0) (115 mg, 100 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave [3-(6-trifluoromethyl-pyridazin-3-yl)-benzyl]-carbamic acid tert-butyl ester (0.65 g, 92%) as a brown solid.

A solution of [3-(6-trifluoromethyl-pyridazin-3-yl)-benzyl]-carbamic acid tert-butyl ester (0.65 g, 1.84 mmol) in CH$_2$Cl$_2$ (5 mL) was treated with trifluoroacetic acid (2.1 g, 18.4 mmol) and then was stirred at 25° C. for 3 h. The solution was concentrated in vacuo gave 3-(6-trifluoromethyl-pyridazin-3-yl)-benzylamine (450 mg, 97%) as a brown oil. M+H=253.9.

A solution of 3-(6-trifluoromethyl-pyridazin-3-yl)-benzylamine (27.6 mg, 109 µmol) and [(4-fluoro-benzenesulfonyl)-isopropyl-amino]-acetic acid (30 mg, 109 µmol) in CH$_2$Cl$_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[3-(6-trifluoromethyl-pyridazin-3-yl)-benzyl]-acetamide (15.2 mg, 27%) as a white solid. MH+=511.0.

Example 67

2-[Isopropyl-(pyrazine-2-sulfonyl)-amino]-N-[6-(4-trifluoromethyl-phenyl)-pyrimidin-4-ylmethyl]-acetamide

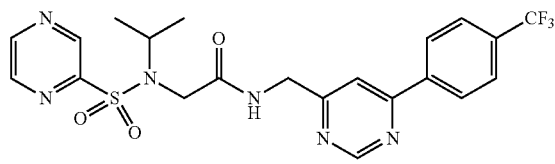 [SMILES: CC(C)N(CC(=O)NCc1cc(-c2ccc(C(F)(F)F)cc2)ncn1)S(=O)(=O)c1cnccn1]

To a solution of sodium sulfite (3.86 g, 30.6 mmol) in water (20 mL) was added 2-fluoropyrazine (2 g, 20.4 mmol). It was stirred at 150° C. under pressure tube overnight. After removal of solvent, the solid was dried to give crude product sodium pyrazine-2-sulfonate as a white solid (6 g) which was used directly for next step without further purification.

To a suspension of crude sodium pyrazine-2-sulfonate (3.71 g) in thionyl chloride (32.6 g, 20 mL, 274 mmol) was added DMF (0.3 mL, 3.87 mmol). It was stirred at reflux for 5 h. After removal of the solid by filtration, the filtrate was concentrated to give crude pyrazine-2-sulfonyl chloride as a red liquid (2 g) which was used directly for next step without further purification.

To a solution of 2-(isopropylamino)-N-((6-(4-(trifluoromethyl)phenyl)pyrimidin-4-yl)methyl)acetamide from Example 27 (30 mg, 85.1 µmol) and N,N-diisopropylethylamine (44.6 µL, 255 µmol) in CH$_2$Cl$_2$ (3 ml) were added crude pyrazine-2-sulfonyl chloride (45.6 mg). It was stirred at room temperature overnight. Ethyl acetate was added. The organic layer was washed with saturated sodium carbonate and brine, dried over anhydrous sodium sulfate, filtered and concentrated in vacuo. Flash chromatography (ethyl acetate) afforded 2-[isopropyl-(pyrazine-2-sulfonyl)-amino]-N-[6-(4-trifluoromethyl-phenyl)-pyrimidin-4-ylmethyl]-acetamide (2 mg, 5%) as a white solid. MH+=495.

Example 68

2-[(4-Fluoro-benzenesulfonyl)-isopropyl-amino]-N-[3-(2-trifluoromethyl-pyrimidin-5-yl)-benzyl]-acetamide

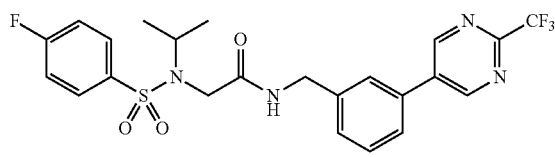

A solution of 3-[(tert-butoxycarbonylamino)methyl]phenylboronic acid (500 mg, 1.99 mmol), 5-bromo-2-(trifluoromethyl)pyrimidine (452 mg, 1.99 mmol) and potassium carbonate (0.28 g, 1.99 mmol) in DMF (5 mL) at 25° C. was purged with nitrogen gas and evacuated three times. The solution was then treated with tetrakis(triphenylphosphine)palladium(0) (115 mg, 100 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave [3-(2-trifluoromethyl-pyrimidin-5-yl)-benzyl]-carbamic acid tert-butylester (0.50 g, 71%) as a brown solid. MH+=354.0.

A solution of [3-(2-trifluoromethyl-pyrimidin-5-yl)-benzyl]-carbamic acid tert-butylester (0.50 g, 1.42 mmol) in CH$_2$Cl$_2$ (5 mL) was treated with trifluoroacetic acid (1.6 g, 14.2 mmol) and then was stirred at 25° C. for 3 h. The solution was concentrated in vacuo gave 3-(2-trifluoromethyl-pyrimidin-5-yl)-benzylamine (320 mg, 89%) as a brown oil. M+H=254.0.

A solution of 3-(2-trifluoromethyl-pyrimidin-5-yl)-benzylamine (27.6 mg, 109 µmol) and [(4-fluoro-benzenesulfonyl)-isopropyl-amino]-acetic acid (30 mg, 109 µmol) in CH$_2$Cl$_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[3-(2-trifluoromethyl-pyrimidin-5-yl)-benzyl]-acetamide (27.5 mg, 49%) as a white solid. MH+=510.9.

Example 69

2-[(3,4-Difluoro-benzenesulfonyl)-isopropyl-amino]-N-[6-(4-trifluoromethyl-phenyl)-pyrimidin-4-ylmethyl]-acetamide

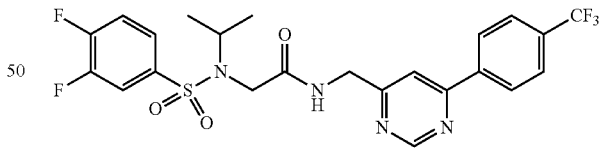

To a solution of 2-(isopropylamino)-N-((6-(4-(trifluoromethyl)phenyl)pyrimidin-4-yl)methyl)acetamide (30 mg, 85.1 µmol) and N,N-diisopropylethylamine (44.6 µL, 255 µmol) in CH$_2$Cl$_2$ (3 ml) were added 3,4-difluorobenzenesulfonyl chloride (27.2 mg, 128 µmol). It was stirred at room temperature overnight. Ethyl acetate was added. The organic layer was washed with saturated sodium carbonate and brine, dried over anhydrous sodium sulfate, filtered and concentrated in vacuo. Flash chromatography (50/50 to 20/80 hexane/ethyl acetate) afforded 2-[(3,4-Difluoro-benzenesulfonyl)-isopropyl-amino]-N-[6-(4-trifluoromethyl-phenyl)-pyrimidin-4-ylmethyl]-acetamide (28 mg, 63%) as a white solid. MH+=529.

Example 70

2-[(4-Fluoro-benzenesulfonyl)-isopropyl-amino]-N-[4-fluoro-3-(2-trifluoromethyl-pyrimidin-5-yl)-benzyl]-acetamide

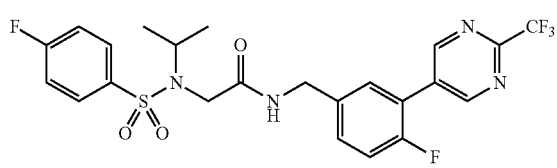 [SMILES: CC(C)N(CC(=O)NCc1ccc(F)c(-c2cnc(C(F)(F)F)nc2)c1)S(=O)(=O)c1ccc(F)cc1]

A solution of 5-(aminomethyl)-2-fluorophenylboronic acid hydrochloride (2.0 g, 9.74 mmol), di-tert-butyl dicarbonate (2.55 g, 11.7 mmol) and triethylamine (1.97 g, 19.5 mmol) in CH$_3$OH (10 mL) was stirred at 25° C. for 3 h. The reaction mixture was poured into water. The aqueous phase was extracted three times with ethyl acetate. The combined organic layers were washed with brine and dried over magnesium sulfate. Filtration followed by concentration in vacuo gave 5-[(tert-butoxycarbonylamino)methyl]-2-fluorophenylboronic acid (2.40 g, 92%) as a brown solid.

A solution of 5-[(tert-butoxycarbonylamino)methyl]-2-fluorophenylboronic acid (500 mg, 1.86 mmol), 5-bromo-2-(trifluoromethyl)pyrimidine (422 mg, 1.86 mmol) and potassium carbonate (0.26 g, 1.86 mmol) in DMF (5 mL) at 25° C. was purged with nitrogen gas and evacuated three times. The solution was then treated with tetrakis(triphenylphosphine)-palladium(0) (107 mg, 93 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave [4-fluoro-3-(2-trifluoromethyl-pyrimidin-5-yl)-benzyl]-carbamic acid tert-butyl ester (500 mg, 73%) as a white solid. MH+=372.0.

A solution of [4-fluoro-3-(2-trifluoromethyl-pyrimidin-5-yl)-benzyl]-carbamic acid tert-butyl ester (0.50 g, 1.35 mmol) in CH$_2$Cl$_2$ (5 mL) was treated with trifluoroacetic acid (1.5 g, 13.5 mmol) and then was stirred at 25° C. for 3 h. The solution was concentrated in vacuo gave 4-fluoro-3-(2-trifluoromethyl-pyrimidin-5-yl)-benzylamine (350 mg, 96%) as a brown oil. M+H=272.0.

A solution of 4-fluoro-3-(2-trifluoromethyl-pyrimidin-5-yl)-benzylamine (29.6 mg, 109 µmol) and [(4-fluoro-benzenesulfonyl)-isopropyl-amino]-acetic acid (30 mg, 109 µmol) in CH$_2$Cl$_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[4-fluoro-3-(2-trifluoromethyl-pyrimidin-5-yl)-benzyl]-acetamide (20.3 mg, 35%) as a white solid. MH+=529.0.

Example 71

2-[(4-Fluoro-benzenesulfonyl)-isopropyl-amino]-N-[3-(5-trifluoromethyl-pyrazin-2-yl)-benzyl]-acetamide

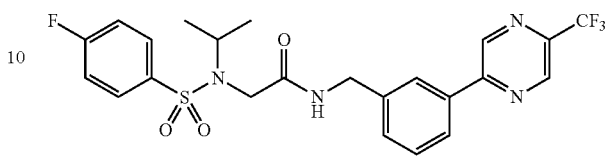

A solution of 3-[(tert-butoxycarbonylamino)methyl]phenylboronic acid (500 mg, 1.99 mmol), 2-chloro-5-trifluoromethyl-pyrazine (363 mg, 1.99 mmol) and potassium carbonate (0.28 g, 1.99 mmol) in DMF (5 mL) at 25° C. was purged with nitrogen gas and evacuated three times. The solution was then treated with tetrakis(triphenylphosphine) palladium(0) (115 mg, 100 µmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave [3-(5-trifluoromethyl-pyrazin-2-yl)-benzyl]-carbamic acid tert-butyl ester (0.65 g, 92%) as a brown solid.

A solution of [3-(5-trifluoromethyl-pyrazin-2-yl)-benzyl]-carbamic acid tert-butyl ester (0.65 g, 1.70 mmol) in CH$_2$Cl$_2$ (5 mL) was treated with trifluoroacetic acid (1.9 g, 17.0 mmol) and then was stirred at 25° C. for 3 h. The solution was concentrated in vacuo gave 3-(5-trifluoromethyl-pyrazin-2-yl)-benzylamine (380 mg, 88%) as a brown oil.

A solution of 3-(5-trifluoromethyl-pyrazin-2-yl)-benzylamine (27.6 mg, 109 µmol) and [(4-fluoro-benzenesulfonyl)-isopropyl-amino]-acetic acid (30 mg, 109 µmol) in CH$_2$Cl$_2$ (5 mL) at 25° C. was treated with HATU (41.4 mg, 109 µmol). N,N-Diisopropylethylamine (28.2 mg, 218 µmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[3-(5-trifluoromethyl-pyrazin-2-yl)-benzyl]-acetamide (20.0 mg, 36%) as a white solid. MH+=511.0.

Example 72

2-[(6-Chloro-pyridine-3-sulfonyl)-isopropyl-amino]-N-[3-(5-trifluoromethyl-pyrazin-2-yl)-benzyl]-acetamide

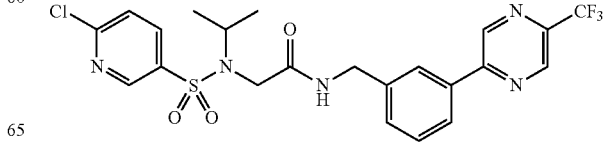

A solution of [(6-chloro-pyridine-3-sulfonyl)-isopropyl-amino]-acetic acid (30.0 mg, 102 μmol) and [(4-fluoro-benzenesulfonyl)-isopropyl-amino]-acetic acid (26 mg, 102 μmol) in CH$_2$Cl$_2$ (5 mL) at 25° C. was treated with HATU (39.0 mg, 102 μmol). N,N-Diisopropylethylamine (26.5 mg, 205 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(6-chloro-pyridine-3-sulfonyl)-isopropyl-amino]-N-[3-(5-trifluoromethyl-pyrazin-2-yl)-benzyl]-acetamide (28.9 mg, 53%) as a white solid. M+H=528.0.

Example 73

2-[(6-Chloro-pyridine-3-sulfonyl)-isopropyl-amino]-N-[3-(6-trifluoromethyl-pyridazin-3-yl)-benzyl]-acetamide

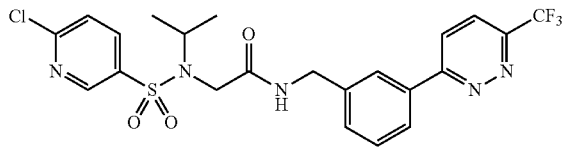 [SMILES: CC(C)N(CC(=O)NCc1cccc(-c2ccc(C(F)(F)F)nn2)c1)S(=O)(=O)c1ccc(Cl)nc1]

A solution of 3-(6-trifluoromethyl-pyridazin-3-yl)-benzylamine (30.0 mg, 102 μmol) and [(6-chloro-pyridine-3-sulfonyl)-isopropyl-amino]-acetic acid (26.0 mg, 102 μmol) in CH$_2$Cl$_2$ (5 mL) at 25° C. was treated with HATU (39.0 mg, 102 μmol). N,N-Diisopropylethylamine (26.5 mg, 205 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(6-chloro-pyridine-3-sulfonyl)-isopropyl-amino]-N-[3-(6-trifluoromethyl-pyridazin-3-yl)-benzyl]-acetamide (20.3 mg, 38%) as a white solid. M+H=528.0.

Example 74

2-[(4-Fluoro-benzenesulfonyl)-isopropyl-amino]-N-[2-(2-trifluoromethyl-pyrimidin-5-yl)-pyridin-4-ylmethyl]-acetamide

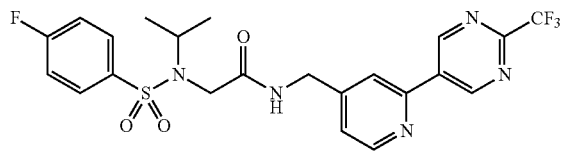

A solution of (2-bromo-pyridin-4-ylmethyl)-carbamic acid tert-butyl ester (300 mg, 1.04 mmol), 2-(trifluoromethyl)pyrimidin-5-ylboronic acid (200 mg, 1.04 mmol) and potassium carbonate (0.14 g, 1.04 mmol) in DMF (5 mL) at 25° C. was purged with nitrogen gas and evacuated three times. The solution was then treated with tetrakis(triphenylphosphine)palladium(0) (60 mg, 52 μmol) and then sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo gave [2-(2-trifluoromethyl-pyrimidin-5-yl)-pyridin-4-ylmethyl]-carbamic acid tert-butyl ester (50 mg, 14%) as a brown solid. M+H=355.0.

A solution of [2-(2-trifluoromethyl-pyrimidin-5-yl)-pyridin-4-ylmethyl]-carbamic acid tert-butyl ester (50 mg, 141 μmol) in CH$_2$Cl$_2$ (5 mL) was treated with TFA (161 mg, 1.41 mmol) and then was stirred at 25° C. for 3 h. The solution was concentrated in vacuo gave C-[2-(2-trifluoromethyl-pyrimidin-5-yl)-pyridin-4-yl]-methylamine (320 mg, 89%) as a brown oil. M+H=254.9.

A solution of C-[2-(2-trifluoromethyl-pyrimidin-5-yl)-pyridin-4-yl]-methylamine (27.7 mg, 109 μmol) and [(4-fluoro-benzenesulfonyl)-isopropyl-amino]-acetic acid (30 mg, 109 μmol) in CH$_2$Cl$_2$ (5 mL) at 25° C. was treated with HATU (41.4 mg, 109 μmol). N,N-Diisopropylethylamine (28.2 mg, 218 μmol) was added to the solution. The reaction mixture was stirred for 2 h. The reaction mixture was then poured into 0.2M aqueous KHSO$_4$ and extracted three times with ethyl acetate. The combined organic layers were washed three times with water and once with brine. The organic layer was then dried over magnesium sulfate, filtered and concentrated in vacuo. Flash chromatography (50/50 hexanes/ethyl acetate) afforded 2-[(4-fluoro-benzenesulfonyl)-isopropyl-amino]-N-[2-(2-trifluoromethyl-pyrimidin-5-yl)-pyridin-4-ylmethyl]-acetamide (44.1 mg, 79%) as a white solid. M+H=512.2.

Example 75

2-[(5-Chloro-thiophene-2-sulfonyl)-isopropyl-amino]-N-[6-(4-trifluoromethyl-phenyl)-pyrimidin-4-ylmethyl]-acetamide

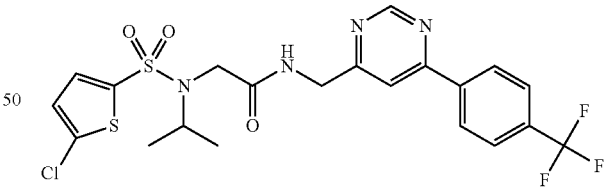

2-(5-chloro-N-isopropylthiophene-2-sulfonamido)acetic acid (70.6 mg, 237 μmol, Eq: 1.00), HATU (180 mg, 474 μmol, Eq: 2.00) and Hunig's base (122 mg, 166 μl, 948 μmol, Eq: 4.00) were combined with DCM (6 ml) at 20° C. and stirred for 10 min. (6-(4-(trifluoromethyl)phenyl)pyrimidin-4-yl)methanamine hydrochloride (60 mg, 237 μmol, Eq: 1.00) was added and stirring continued for 14 h. The crude material was purified by flash chromatography (80-90% ethyl acetate/hexanes) to afford 2-[(5-chloro-thiophene-2-sulfonyl)-isopropyl-amino]-N-[6-(4-trifluoromethyl-phenyl)-pyrimidin-4-ylmethyl]-acetamide as a solid. MH+=534.

Example 76

2-[(5-Chloro-thiophene-2-sulfonyl)-isopropyl-amino]-N-[6-(6-trifluoromethyl-pyridin-3-yl)-pyrimidin-4-ylmethyl]-acetamide

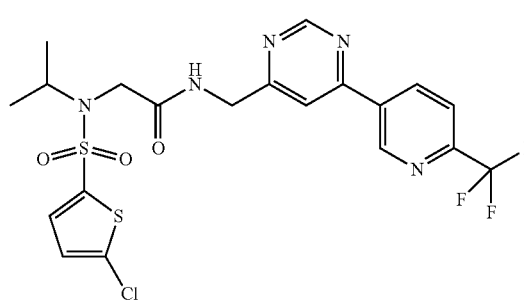

2-(5-chloro-N-isopropylthiophene-2-sulfonamido)acetic acid (64.4 mg, 216 µmol, Eq: 1.10), HATU (150 mg, 393 µmol, Eq: 2.00) and N-ethyl-N-isopropylpropan-2-amine (102 mg, 787 µmol, Eq: 4.00) were combined with $CH_2CH_2$ (6 ml) and stirred for 10 min. at 20° C. (6-(6-(trifluoromethyl) pyridin-3-yl)pyrimidin-4-yl)methanamine (50 mg, 197 µmol, Eq: 1.00). HCl was added and stirred for 5 h. The crude material was purified by flash chromatography (80-90% ethyl acetate/hexanes) to afford 2-[(5-chloro-thiophene-2-sulfonyl)-isopropyl-amino]-N-[6-(6-trifluoromethyl-pyridin-3-yl)-pyrimidin-4-ylmethyl]-acetamide. MH+=535.

Example 77

2-(4-fluoro-N-isopropylphenylsulfonamido)-N-(3-(pyrrolidin-1-yl)benzyl)acetamide

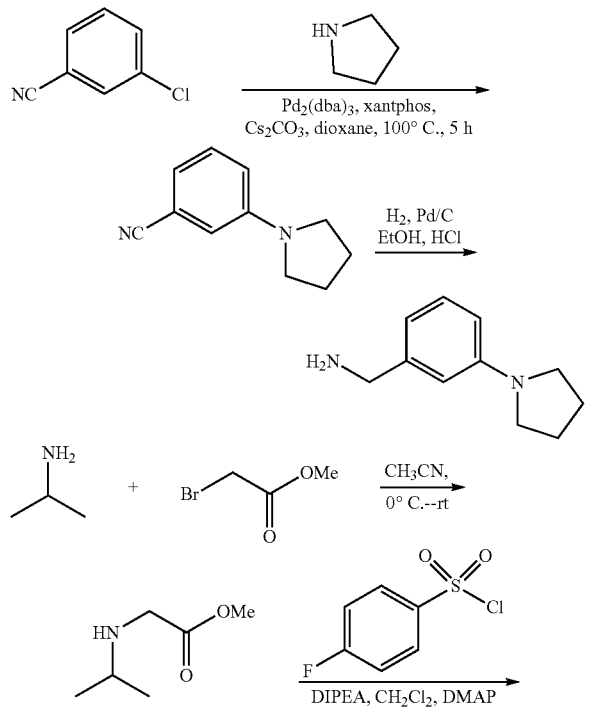

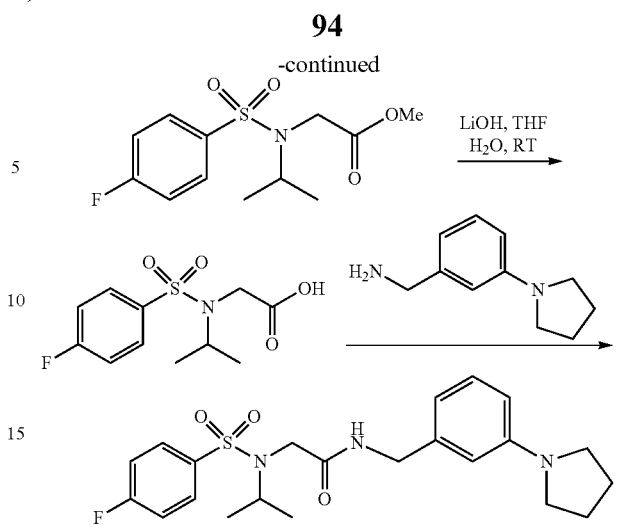

3-(Pyrrolidin-1-yl)benzonitrile

A 250-mL single-neck round-bottomed flask equipped with a magnetic stirrer and a reflux condenser was charged with 3-chlorobenzonitrile (2.0 g, 14.60 mmol), pyrrolidine (1.6 g, 21.90 mmol), $Pd_2(dba)_3$ (67 mg, 0.073 mmol), xantphos (84 mg, 0.15 mmol), $Cs_2CO_3$ (9.5 g, 29.14 mmol) and dioxane (60 mL). The system was subject to 3 cycles of vacuum/argon flush and heated at 100° C. for 5 h. The mixture was cooled to room temperature and filtered. The filtrate was concentrated under reduced pressure. The residue was purified by silica-gel column chromatography eluting with 10:1 PE/EA to afford the title compound (1.3 g, 52%) as light yellow solid. MS-ESI: $[M+H]^+73.1$ (3-(Pyrrolidin-1-yl)phenyl)methanamine A 50-mL single-neck round-bottomed flask equipped with a magnetic stirrer was charged with 3-(pyrrolidin-1-yl)benzonitrile (500 mg, 2.91 mmol), Pd/C (75 mg, 10%), concentrated HCl (1 drop), and $CH_3OH$ (10 mL). The system was subject to 3 cycles of vacuum/hydrogen flush and stirred at room temperature for 5 h under $H_2$. The resulting mixture was filtered and the filtrate was concentrated under reduced pressure to afford the crude title compound (460 mg, 90%), which was used for next step without purification. MS-ESI: $[M+H]^+177.1$ Methyl 2-(isopropylamino)acetate A 500-mL single-neck round-bottomed flask equipped with a magnetic stirrer was charged with propan-2-amine (5.0 g, 84.75 mmol), $K_2CO_3$ (35.09 g, 254.25 mmol), and $CH_3CN$ (90 mL). The mixture was stirred at 0° C. for 30 minutes. And then methyl 2-bromoacetate (12.88 g, 84.75 mmol) in $CH_3CN$ (50 mL) was added slowly at 0° C. over a period of 1 h. The mixture was stirred at 0° C. for another 1 h. The solid was removed by filtration, and the filtrate was concentrated under reduced pressure. The residue was sonicated in ether and solid was removed by filtration. The filtrate was concentrated under reduced pressure to afford colorless oil (8.1 g, 73%), which was directly used for the next step without further purification.

Methyl 2-(4-fluoro-N-isopropylphenylsulfonamido)acetate

A 250-mL single-neck round-bottomed flask equipped with a magnetic stirrer was charged with methyl 2-(isopropylamino)acetate (3.50 g, 26.72 mmol), 4-fluorobenzene-1-sulfonyl chloride (5.18 g, 26.72 mmol), DIPEA (5.20 g, 40.08 mmol), DMAP (122 mg, 1.0 mmol), and CH$_2$Cl$_2$ (90 mL). The mixture was stirred at room temperature for 2 h. Then the solvent was removed under reduced pressure. The residue was purified by silica-gel column chromatography eluting with 1:3 PE/EA to afford the title compound (5.0 g, 65%) as a white solid. MS-ESI: [M+H]$^+$290.1

2-(4-Fluoro-N-isopropylphenylsulfonamido)acetic acid

A 250-mL single-neck round-bottomed flask equipped with a magnetic stirrer was charged with methyl 2-(4-fluoro-N-isopropylphenylsulfonamido)acetate (3.0 g, 10.38 mmol), LiOH (2.47 g, 103.80 mmol), THF (50 mL), and H$_2$O (5 mL). The mixture was stirred at room temperature for 1 h and concentrated under reduced pressure. The residue was diluted with H$_2$O (10 mL) and then the resulting mixture was adjusted to pH 4 with 1N HCl. The mixture was extracted with ethyl acetate and the combined organic layer was concentrated under reduced pressure to afford the crude title compound (1.5 g, 53%), which was used directly for the next step without any further purification. MS-ESI: [M+H]$^+$276.1

2-(4-Fluoro-N-isopropylphenylsulfonamido)-N-(3-(pyrrolidin-1-yl)benzyl)acetamide A 50-mL single-neck round-bottomed flask equipped with a magnetic stirrer was charged with 2-(4-fluoro-N-isopropylphenylsulfonamido)acetic acid (100 mg, 0.36 mmol), (3-(pyrrolidin-1-yl)phenyl)methanamine (63 mg, 0.36 mmol), HATU (274 mg, 0.72 mmol), TEA (0.3 mL), and CH$_2$Cl$_2$ (10 mL). The mixture was stirred at room temperature for 1 h and added 2% KHSO$_4$ solution. The resulting mixture was extracted with DCM. The combined organic layer was concentrated under reduced pressure. The residue was purified by reverse-phase prep-HPLC to afford the title compound as a white solid (45 mg, 46%). MS-ESI: [M+H]$^+$ 434.1. $^1$H NMR (500 MHz, CDCl$_3$) δ 7.85-7.82 (m, 2H), 7.20-7.16 (m, 3H), 6.84 (s, 1H), 6.57-6.47 (m, 3H), 4.44 (d, J=5.5 Hz, 2H), 4.23-4.18 (m, 1H), 3.73 (s, 2H), 3.28-3.26 (m, 4H), 2.00-1.97 (m, 4H), 0.98 (d, J=6.5 Hz, 6H).

Example 78

N-(3-cyclopropylbenzyl)-2-(4-fluoro-N-isopropyl-phenylsulfonamido)acetamide

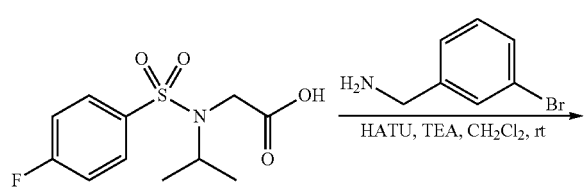

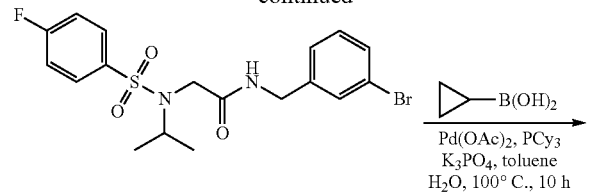

N-(3-Bromobenzyl)-2-(4-fluoro-N-isopropylphenyl-sulfonamido)acetamide

A 250-mL single-neck round-bottomed flask equipped with a magnetic stirrer was charged with 2-(4-fluoro-N-isopropylphenylsulfonamido)acetic acid (1.0 g, 3.64 mmol), (3-bromophenyl)methanamine (690 mg, 3.64 mmol), HATU (2.76 g, 7.28 mmol), TEA (3 ml), and CH$_2$Cl$_2$ (50 mL). The mixture was stirred at room temperature for 2 h and added 2% KHSO$_4$ solution. The resulting mixture was extracted with DCM. The combined organic layer was concentrated under reduced pressure. The residue was purified by silica-gel column chromatography eluting with 3:1 PE/EA to afford the title compound as white solid (960 mg, 60%). MS-ESI: [M+H]$^+$443.1.

N-(3-Cyclopropylbenzyl)-2-(4-fluoro-N-isopropyl-phenylsulfonamido)acetamide

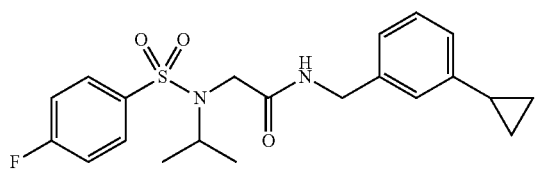

A 50-mL single-neck round-bottomed flask equipped with a magnetic stirrer and a reflux condenser was charged with N-(3-bromobenzyl)-2-(4-fluoro-N-isopropylphenyl-sulfonamido)acetamide (150 mg, 0.33 mmol, 1.0 eq.), cyclopropylboronic acid (146 mg, 1.69 mmol, 5.0 eq.), PCy$_3$ (38 mg, 0.14 mmol, 0.4 eq.), Pd(OAc)$_2$ (15 mg, 0.067 mmol, 0.2 eq.), K$_3$PO$_4$ (210 mg, 0.99 mmol, 3.0 eq.), toluene (6 mL), and H$_2$O (0.5 mL). After three cycles of vacuum/argon flash, the mixture was heated at 100° C. for 10 h. It was cooled to room temperature and filtered through a celite pad. The filtrate was evaporated under reduced pressure and the residue purified by reverse-phase prep-HPLC to afford the title compound (65 mg, 48%) as a white solid. MS-ESI: [M+H]$^+$405.1. $^1$H NMR (500 MHz, DMSO-d$_6$) δ 8.36-8.34 (m, 1H), 8.06-8.03 (m, 2H), 7.45-7.42 (m, 2H), 7.19-7.16 (m, 1H), 7.04-7.02 (m, 1H), 6.98-6.95 (m, 2H), 4.28 (d, J=6.0 Hz, 2H), 3.87-3.85 (m, overlap, 3H), 1.88-1.86 (m, 1H), 0.94-0.90 (m, 8H), 0.65-0.63 (m, 2H)

Example 79
(R)-2-(4-fluoro-N-isopropylphenylsulfonamido)-N-(3-(2-(2-methylpyrrolidin-1-yl)pyrimidin-5-yl)benzyl)acetamide and (S)-2-(4-fluoro-N-isopropylphenylsulfonamido)-N-(3-(2-(2-methylpyrrolidin-1-yl)pyrimidin-5-yl)benzyl)acetamide
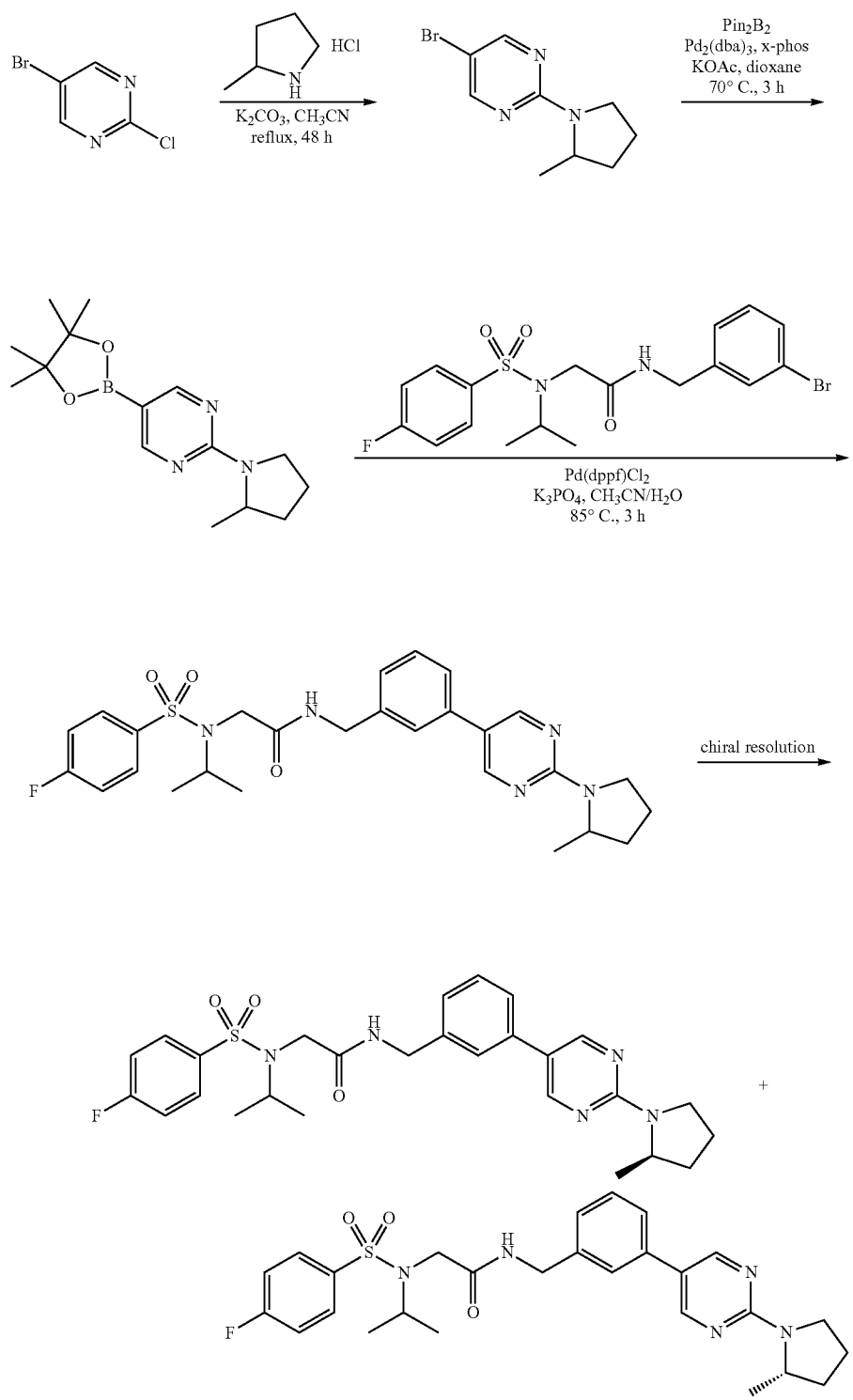

(+,−)-5-bromo-2-(2-methylpyrrolidin-1-yl)pyrimidine

A 500-mL round-bottomed flask equipped with a magnetic stirrer and a reflux condenser was charged with 5-bromo-2-chloropyrimidine (13.6 g, 70.4 mmol, 1.0 eq.), 2-methyl-pyrrolidine hydrochloride (10.5 g, 86.8 mmol, 1.2 eq.), $K_2CO_3$ (22.4 g, 154.8 mmol, 2.2 eq.) and $CH_3CN$ (150 mL). The reaction was heated at reflux for 48 h. After this time it was cooled to room temperature, filtered, and concentrated under reduced pressure. The residue was purified by silica-gel column chromatography eluting with 1:3 EA/PE to afford the racemic title compound 15 g (yield, 88%) as a white solid. MS-ESI: $[M+H]^+$242.1.

(+,−)-2-(2-methylpyrrolidin-1-yl)-5-(4,4,5,5-tetramethyl-1,3,2-dioxaborolan-2-yl)pyrimidine A 250-mL round-bottomed flask equipped with a magnetic stirrer and a reflux condenser was charged with racemic 5-bromo-2-(2-methylpyrrolidin-1-yl)pyrimidine (6.0 g, 24.8 mmol, 1.0 eq.), $Pin_2B_2$ (18.9 g, 74.4 mmol, 3.0 eq.), $Pd_2(dba)_3$ (11.1 g, 1.24 mmol, 0.05 eq.), x-phos (1.1 g, 2.48 mmol, 0.1 eq.), KOAc (7.3 g, 74.4 mmol, 3.0 eq.) and dioxane (100 mL). After three cycles of vacuum/argon flush, the mixture was heated at 70° C. for 3 h. It was then cooled to room temperature and filtered. The filtrate was concentrated under reduced pressure and the resulting residue was washed with petroleum to afford 6.1 g of the crude racemic title compound as a yellow solid, which was used directly to the next step.
MS-ESI: $[M+H]^+$290.0

(+,−)-2-(4-fluoro-N-isopropylphenylsulfonamido)-N-(3-(2-(2-methylpyrrolidin-1-yl)pyrimidin-5-yl)benzyl)acetamide A 50-mL single-neck round-bottomed flask equipped with a magnetic stirrer and a reflux condenser was charged with racemic 2-(2-methylpyrrolidin-1-yl)-5-(4,4,5,5-tetramethyl-1,3,2-dioxaborolan-2-yl)pyrimidine (270 mg, 0.93 mmol, 1.4 eq.), N-(3-bromobenzyl)-2-(4-fluoro-N-isopropylphenylsulfonamido)-acetamide (300 mg, 0.67 mmol, 1.0 eq.), Pd(dppf)Cl$_2$ (35 mg, 0.033 mmol, 0.05 eq.), $K_3PO_4$ (424 mg, 2.0 mmol, 3.0 eq.), $CH_3CN$ (10 mL), and $H_2O$ (2 mL). After three cycles of vacuum/argon flush, the mixture was heated at 85° C. for 3 h. It was cooled to room temperature and filtered through a celite pad. The filtrate was evaporated under reduced pressure and the residue was purified by reverse-phase prep-HPLC to afford the racemic mixture of the title compounds (265 mg, 54%) as a white solid. After chiral resolution, two enantiomers were obtained, the amounts of which were 21 mg and 27 mg respectively (absolute stereochemistry is arbitrarily assigned).
MS-ESI: $[M+H]^+$526.2.

(R)-2-(4-fluoro-N-isopropylphenylsulfonamido)-N-(3-(2-(2-methylpyrrolidin-1-yl)pyrimidin-5-yl)benzyl)acetamide $^1$H NMR (500 MHz, CDCl$_3$) faster eluting isomer: δ 8.60-8.59 (m, 2H), 7.90-7.87 (m, 2H), 7.45-7.42 (m, 3H), 7.30-7.29 (m, 1H), 7.24-7.21 (m, 2H), 7.05-7.04 (m, 1H), 4.59 (d, J=6.0 Hz, 2H), 4.38-4.26 (m, 2H), 3.77 (s, 2H), 3.76-3.74 (m, 1H), 3.61-3.59 (m, 1H), 2.15-2.02 (m, 3H), 1.80-1.77 (m, 1H), 1.31 (d, J=6.5 Hz, 3H), 1.01 (d, J=6.5 Hz, 6H).

(S)-2-(4-fluoro-N-isopropylphenylsulfonamido)-N-(3-(2-(2-methylpyrrolidin-1-yl)pyrimidin-5-yl)benzyl)acetamide $^1$H NMR (500 MHz, CDCl$_3$) slower eluting isomer: δ 8.60-8.59 (m, 2H), 7.90-7.87 (m, 2H), 7.46-7.42 (m, 3H), 7.30-7.29 (m, 1H), 7.24-7.21 (m, 2H), 7.04-7.03 (m, 1H), 4.59 (d, J=6.0 Hz, 2H), 4.38-4.25 (m, 2H), 3.77 (s, 2H), 3.76-3.74 (m, 1H), 3.62-3.60 (m, 1H), 2.16-2.03 (m, 3H), 1.80-1.77 (m, 1H), 1.31 (d, J=6.0 Hz, 3H), 1.01 (d, J=6.5 Hz, 6H).

Example 80

2-(4-Fluoro-N-isopropylphenylsulfonamido)-N-((6-(4-(trifluoromethyl)piperidin-1-yl)pyrimidin-4-yl)methyl)acetamide

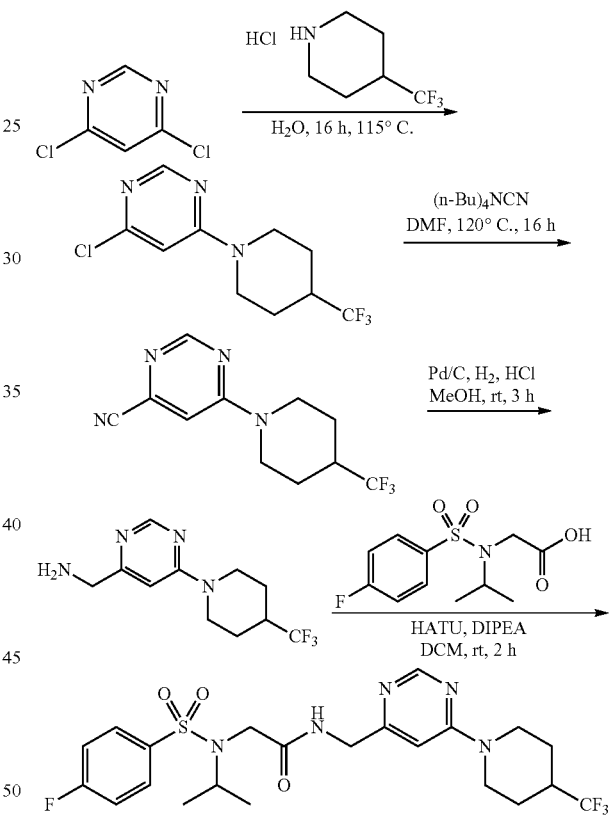

4-Chloro-6-(4-(trifluoromethyl)piperidin-1-yl)pyrimidine. A mixture of 4,6-dichloropyrimidine (1.48 g, 10 mmol), DIPEA (2.58 g, 20 mmol) and 4-(trifluoromethyl)piperidine hydrochloride (1.89 g, 10 mmol) in 15 mL water was stirred at 115° C. for 16 h. After cooling to room temperature, the precipitate was collected by filtration, washed with water, and dried in vacuum to afford the title compound (2.38 g, 89%) as a white solid. MS-ESI: $[M+H]^+$ 266.0

6-(4-(trifluoromethyl)piperidin-1-yl)pyrimidine-4-carbonitrile

A mixture of 4-chloro-6-(4-(trifluoromethyl)piperidin-1-yl)pyrimidine (0.53 g, 2.0 mmol) and tetraethylamtnonium cyanide (1.34 g, 5.0 mmol) in dimethylformamide (15 mL) was stirred at 120° C. for 16 hours. To this mixture was added water and EA. The organic phase was separated, washed with water, dried and filtered. The filtrate was evaporated under reduced pressure and the residue was purified by silica-gel column chromatography to afford the title compound (0.20 g, 40%) as a light yellow solid. MS-ESI: [M+H]$^+$256.9

(6-(4-(Trifluoromethyl)piperidin-1-yl)pyrimidin-4-yl)methanamine

A 50-mL single-neck round-bottomed flask was purged with nitrogen and charged with 6-(4-(trifluoromethyl)piperidin-1-yl)pyrimidine-4-carbonitrile (0.20 g, 0.78 mmol), 10% palladium on carbon (50% wet, 50 mg), 12 N HCl (0.10 mL) and MeOH (6 mL). The mixture was evacuated, charged with hydrogen gas, and stirred at room temperature for 4 h. The hydrogen was then evacuated and nitrogen was charged into the flask. The catalyst was removed by filtration through a pad of Celite and the filtrate was concentrated under reduced pressure to afford the title compound (0.20 g, 99%). MS-ESI: [M+H]$^+$261.0

2-(4-fluoro-N-isopropylphenylsulfonamido)-N-((6-(4-(trifluoromethyl)piperidin-1-yl)pyrimidin-4-yl)methyl)acetamide A mixture of (6-(4-(trifluoromethyl)piperidin-1-yl)pyrimidin-4-yl)methanamine (130 mg, 0.50 mmol), 2-(4-fluoro-N-isopropylphenylsulfonamido)acetic acid (138 mg, 0.50 mmol), HATU (380 mg, 1.0 mmol) and DIPEA (129 mg, 1.0 mmol) in DCM (8 mL) was stirred at 25° C. for 2 h. The mixture was evaporated under reduced pressure and the residue was purified by reverse-phase prep-HPLC to afford the title compound (72 mg, 27%) as a white solid. MS-ESI: [M+14]$^+$517.2.

1H NMR (500 MHz, CDCl$_3$) 1H NMR (500 MHz, CDCl$_3$) δ 8.55 (s, 1H), 7.94-7.91 (m, 2H), 7.29-7.24 (m, 3H), 6.71 (s, 1H), 4.62-4.60 (m, 2H), 4.51 (d, J=6.0 Hz, 2H), 4.25-4.21 (m, 1H), 3.79 (s, 2H), 2.91-2.86 (m, 2H), 2.34-2.31 (m, 1H), 1.98-1.95 (m, 2H), 1.58-1.54 (m, 2H), 1.03 (d, J=7.0 Hz, 6H).

Example 81

N-((6-(4,4-Difluoropiperidin-1-yl)pyrimidin-4-yl)methyl)-2-(4-fluoro-N-isopropylphenylsulfonamido)acetamide

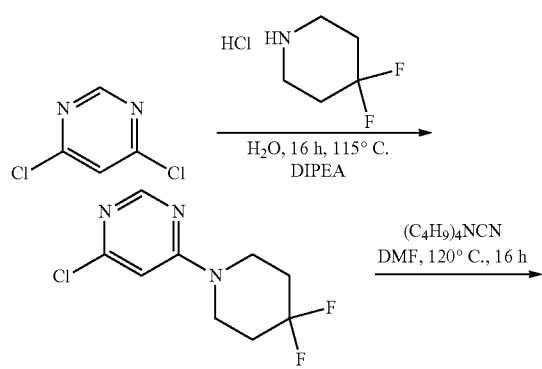

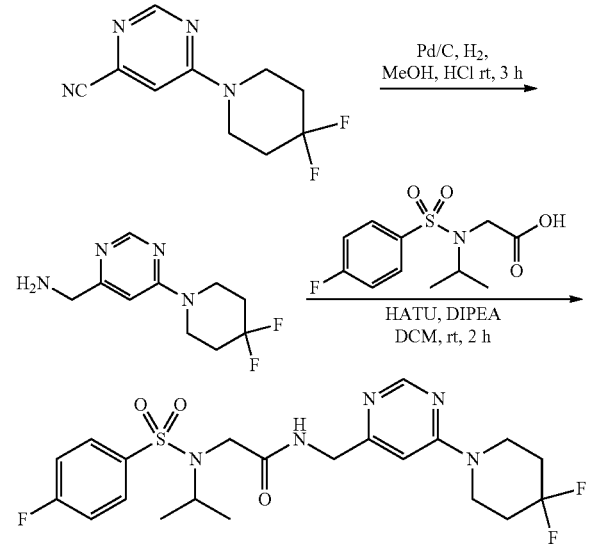

4-Chloro-6-(4,4-difluoropiperidin-1-yl)pyrimidine

A mixture of 4,6-dichloropyrimidine (0.89 g, 6.0 mmol, DIPEA (1.55 g, 12 mmol) and 4,4-difluoropiperidine hydrochloride (942 mg, 6.0 mmol) in water (10 mL) was stirred at 115° C. for 16 h. After cooling to room temperature, the precipitate was collected by filtration, washed with water. and dried in vacuum to afford the title compound (1.25 g, 88%) as a white solid. MS-ESI: [M+H]$^+$233.8

6-(4,4-difluoropiperidin-1-yl)pyrimidine-4-carbonitrile

A mixture of 4-chloro-6-(4,4-difluoropiperidin-1-yl)pyrimidine (0.47 g, 2.0 mmol) and tetraethylamtnonium cyanide (1.34 g, 5.0 mmol) in dimethylformamide (15 mL) was stirred at 120° C. for 16 hours. To this mixture was added water and EA. The organic phase was separated, washed with water, dried and filtered. The filtrate was evaporated under reduced pressure and the residue was purified by silica-gel column chromatography eluting with 10:1 PE/EA to afford the title compound (0.35 g, 71%) as a light yellow solid. MS-ESI: [M+H]$^+$225.1

(6-(4,4-difluoropiperidin-1-yl)pyrimidin-4-yl)methanamine

A 50-mL single-neck round-bottomed flask was purged with nitrogen and charged with 6-(4,4-difluoropiperidin-1-yl)pyrimidine-4-carbonitrile (0.35 g, 1.56 mmol), 10% palladium on carbon (50% wet, 100 mg), 12 N HCl (0.25 mL) and MeOH (10 mL). The mixture was evacuated, charged with hydrogen gas, and stirred at room temperature for 4 h. The hydrogen was then evacuated and nitrogen was charged into the flask. The catalyst was removed by filtration through a pad of Celite and the filtrate was concentrated under reduced pressure to afford the title compound (0.35 g, 99%). MS-ESI: [M+H]$^+$229.1.

N-((6-(4,4-Difluoropiperidin-1-yl)pyrimidin-4-yl)methyl)-2-(4-fluoro-N-isopropylphenylsulfonamido)acetamide. A mixture of (6-(4,4-difluoropiperidin-1-yl)pyrimidin-4-yl)methanamine (114 mg, 0.50 mmol), 2-(4-fluoro-N-isopropylphenylsulfonamido)-acetic acid (138 mg, 0.50 mmol), HATU (380 mg, 1.0 mmol) and DIPEA (129 mg, 1.0 mmol) in DCM (8 mL) was stirred at 25° C. for 2 h. The mixture was evaporated under reduced pressure and the residue was purified by reverse-phase prep-HPLC to afford the title compound (71 mg, 30%) as a white solid. MS-ESI: [M+H]$^+$486.1. 1H NMR (500 MHz, CDCl$_3$) δ 8.56 (s, 1H), 7.93-7.90 (m, 2H), 7.29-7.24 (m, 3H), 6.78 (s, 1H), 4.52 (d, J=6.0 Hz, 2H), 4.25-4.23 (m, 1H), 3.86-3.84 (m, 4H), 3.78 (s, 2H), 2.03-1.98 (m, 4H), 1.03 (d, J=7.0 Hz, 6H).

Example 82

2-(N-Isopropyl-1-methyl-1H-pyrazole-3-sulfonamido)-N-((4'-(trifluoromethyl)biphenyl-3-yl)methyl)acetamide

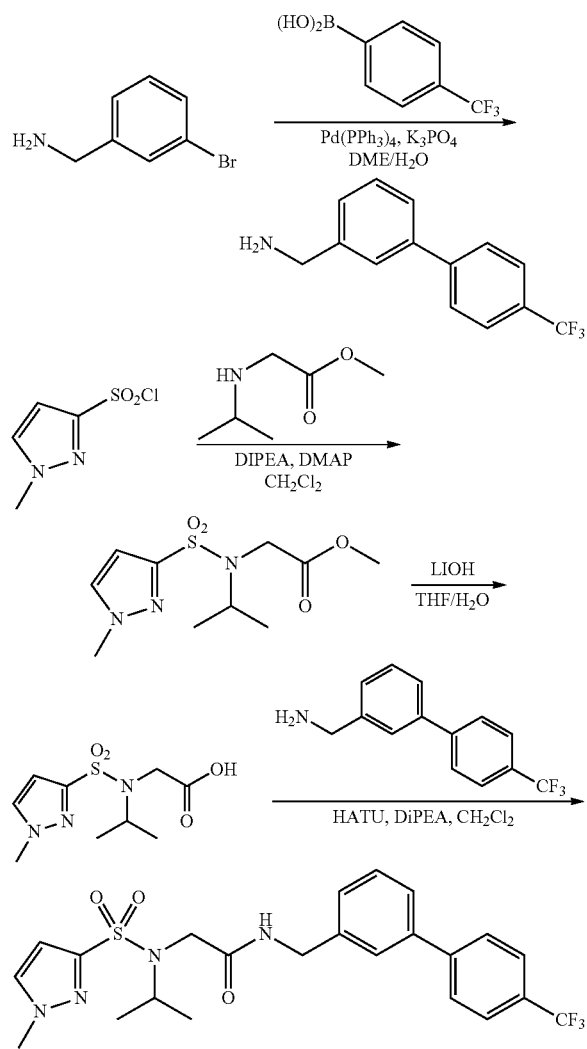

(4'-(Trifluoromethyl)biphenyl-3-yl)methanamine

A 100-mL single-neck round-bottomed flask equipped with a magnetic stirrer and a reflux condenser was charged with (3-bromophenyl)methanamine (570 mg, 3.0 mmol), 4-(trifluoromethyl)phenylboronic acid (558 mg, 3.0 mmol), Pd(PPh$_3$)$_4$ (173 mg, 0.15 mmol), K$_3$PO$_4$ (1.91 g, 9.0 mmol), DME (30 mL) and H$_2$O (6 mL). The system was subject to 3 cycles of vacuum/argon flush and heated at reflux for overnight. The mixture was cooled to room temperature and filtered. The filtrate was concentrated under reduced pressure. The residue was purified by silica-gel column chromatography eluting with 1:20 MeOH/CH$_2$Cl$_2$ to afford the title compound (640 mg, 85%) as brown solid. MS-ESI: [M+H]$^+$252.1.

Methyl 2-(N-isopropyl-1-methyl-1H-pyrazole-3-sulfonamido)acetate

A 25-mL single-neck round-bottomed flask equipped with a magnetic stirrer was charged with 1-methyl-1H-pyrazole-3-sulfonyl chloride (220 mg, 1.2 mmol), methyl 2-(isopropylamino)-acetate (157 mg, 1.2 mmol), DIPEA (310 mg, 2.4 mmol), DMAP (12 mg, 0.10 mmol), and CH$_2$Cl$_2$ (10 mL). The mixture was stirred at room temperature for 2 h and concentrated under reduced pressure. The residue was purified by reverse-phase prep-HPLC to afford the title compound (202 mg, 61%) as white solid. MS-ESI: [M+H]$^+$ 276.1. $^1$H NMR (500 MHz, CDCl$_3$) δ 7.43 (d, J=2.5 Hz, 1H), 6.74 (d, J=2.0 Hz, 1H), 4.27-4.24 (m, 1H), 4.02 (s, 2H), 3.99 (s, 3H), 3.77 (s, 3H), 1.09 (d, J=6.5 Hz, 6H).

2-(N-isopropyl-1-methyl-1H-pyrazole-3-sulfonamido)acetic acid

A 25-mL single-neck round-bottomed flask equipped with a magnetic stirrer was charged with methyl 2-(N-isopropyl-1-methyl-1H-pyrazole-3-sulfonamido)acetate (150 mg, 0.55 mmol), LiOH (65 mg, 2.73 mmol), THF (10 mL), and H$_2$O (2 mL). The mixture was stirred at room temperature for 1 h and the resulting mixture was adjusted to pH 4 with 1N HCl. It was then concentrated under reduced pressure and extracted with ethyl acetate. The combined organic layer was concentrated under reduced pressure to afford the crude title compound (120 mg, 84%), which was used directly for the next step without any further purification. MS-ESI: [M+H]$^+$262.1.

2-(N-isopropyl-1-methyl-1H-pyrazole-3-sulfonamido)-N-((4'-(trifluoromethyl)-biphenyl-3-yl)methyl)acetamide A 25-mL single-neck round-bottomed flask equipped with a magnetic stirrer was charged with (4'-(trifluoromethyl)biphenyl-3-yl)methanamine (50 mg, 0.20 mmol), 2-(N-isopropyl-1-methyl-1H-pyrazole-3-sulfonamido)acetic acid (52 mg, 0.20 mmol), HATU (152 mg, 0.40 mmol), DIPEA (52 mg, 0.40 mmol), and CH$_2$Cl$_2$ (10 mL). The mixture was stirred at room temperature for 1 h. To the resulting mixture was added 2% KHSO$_4$ solution and extracted with DCM. The combined organic layer was concentrated under reduced pressure. The residue was purified by reverse-phase prep-HPLC to afford the title compound as white solid (45 mg, 46%). MS-ESI: [M+H]$^+$495.1. $^1$H NMR (500 MHz, CDCl$_3$) δ 7.85-7.83 (m, 1H), 7.71-7.68 (m, 4H), 7.58 (s, 1H), 7.52 (d, J=8.5 Hz, 1H), 7.47-7.44 (m, 1H), 7.40 (d, J=2.0 Hz, 1H), 7.36 (d, J=7.5 Hz, 1H), 6.74 (d, J=2.5 Hz, 1H), 4.63 (d, J=6.0 Hz, 2H), 4.17-4.14 (m, 1H), 4.01 (s, 2H), 3.78 (s, 3H), 1.11 (d, J=6.0 Hz, 6H).

Example 83

2,2-Dideuterio-2-(4-fluoro-N-isopropylphenylsulfonamido)-N-((6-(6-(trifluoromethyl)pyridin-3-yl)pyrimidin-4-yl)methyl)acetamide

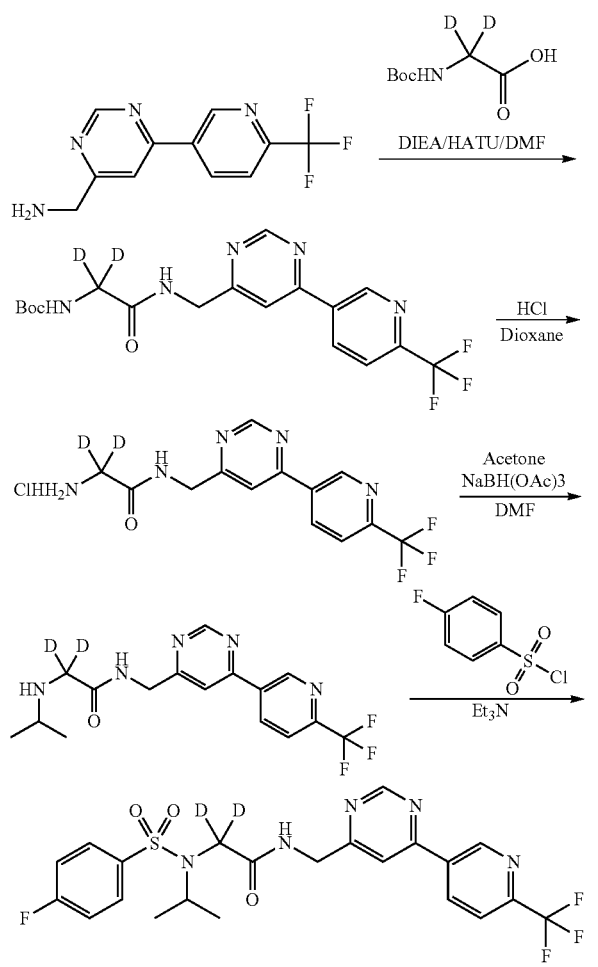

2,2-Dideuterio-tert-butyl2-oxo-2-((6-(6-(trifluoromethyl)pyridin-3-yl)pyrimidin-4-yl)methylamino)ethylcarbamate A mixture of [6-[6-(trifluoromethyl)pyridin-3-yl]pyrimidin-4-yl]methanamine (574 mg, 2.26 mmol, 1.00 equiv), 2,2-dideuterioglycine (400 mg, 2.26 mmol, 1.00 equiv), DIPEA (875 mg, 6.77 mmol, 3.00 equiv), HATU (1.03 g, 2.71 mmol, 1.20 equiv) in DMF (50 mL) was stirred under nitrogen for 2 h at 25° C. The resulting mixture was concentrated under reduced pressure. The residue was dissolved in ethyl acetate (100 mL) and washed with brine (3×50 mL). The organic phase was dried over anhydrous sodium sulfate and concentrated under reduced pressure. The residue was purified by flash chromatography on silica gel, eluting with dichloromethane/methanol (10:1) to afford the title compound (1.4 g) as brown syrup. MS-ESI: [M+H]$^+$ 414.2.

2,2-Dideuterio-2-amino-N-((6-(6-(trifluoromethyl)pyridin-3-yl)pyrimidin-4-yl)methyl)acetamide hydrochloride A mixture of 2,2-dideuterio-tert-butyl2-oxo-2-((6-(6-(trifluoromethyl)pyridin-3-yl)pyrimidin-4-yl)methylamino)ethylcarbamate (1.4 g, 3.39 mmol, 1.00 equiv), 4 N HCl (10 mL) in dioxane (60 mL) was stirred for 2 h at room temperature. The resulting mixture was concentrated under reduced pressure to afford the crude title compound (1.5 g, HCl salt form) as a light brown solid, which was used directly without further purification. MS-ESI: [M+H]$^+$314.2.

2,2-Dideuterio-2-(isopropylamino)-N-((6-(6-(trifluoromethyl)pyridin-3-yl)pyrimidin-4-yl)methyl)acetamide NaBH(OAc)$_3$ (909 mg, 4.29 mmol, 3.00 equiv) was added to a solution of 2,2-dideuterio-2-amino-N-((6-(6-(trifluoromethyl)pyridin-3-yl)pyrimidin-4-yl)methyl)-acetamide hydrochloride (500 mg, 1.43 mmol, 1.00 equiv), propan-2-one (83 mg, 1.43 mmol, 1.00 equiv) in DMF (20 mL). The reaction mixture was stirred overnight at room temperature and then quenched by the addition of water (10 mL). The resulting mixture was concentrated under reduced pressure. The residue was purified by flash chromatography on silica gel, eluting with dichloromethane/methanol (10:1) to afford the title compound (220 mg, 43%) as a brown solid. MS-ESI: [M+H]$^+$356

2,2-Dideuterio-2-(4-fluoro-N-isopropylphenylsulfonamido)-N-((6-(6-(trifluoromethyl) pyridin-3-yl) pyrimidin-4-yl)methyl)acetamide To a solution of 2,2-dideuterio-2-(isopropylamino)-N-((6-(6-(trifluoromethyl)pyridin-3-yl)pyrimidin-4-yl)methyl)acetamide (220 mg, 0.62 mmol, 1.00 equiv) and triethylamine (182 mg, 1.80 mmol, 2.90 equiv) in dichloromethane (10 mL) was added 4-fluorobenzene-1-sulfonyl chloride (180 mg, 0.92 mmol, 1.50 equiv) at room temperature. The resulting solution was stirred overnight at room temperature and concentrated under reduced pressure. The residue was purified by flash chromatography on silica gel, eluting with ethyl acetate/petroleum ether (1:10) to afford the title compound (38.1 mg, 12%) as a white solid. MS-ESI: [M+H]$^+$ 514. $^1$H NMR (300 MHz, DMSO-d$_6$) δ 9.45 (s, 1H), 9.29 (s, 1H), 8.76-8.72 (m, 2H), 8.16 (s, 1H), 8.08-8.02 (m, 3H), 7.45-7.39 (m, 2H), 4.52 (d, J=6.0 Hz, 2H), 3.95-3.86 (m, 1H), 0.97 (d, J=6.5 Hz, 6H).

Example 84

1-(4-Fluoro-N-isopropylphenylsulfonamido)-N-((6-(6-(trifluoromethyl)pyridin-3-yl)pyrimidin-4-yl)methyl)cyclopropanecarboxamide

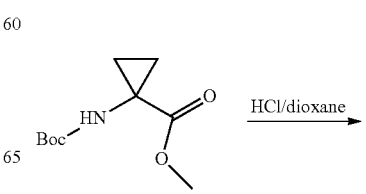

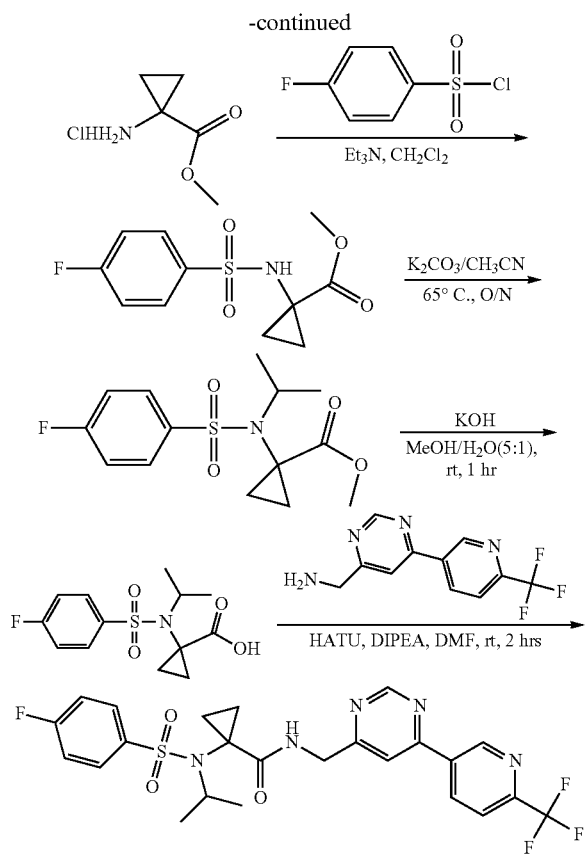

Methyl 1-aminocyclopropanecarboxylate hydrochloride

A mixture of methyl 1-[[(tert-butoxy)carbonyl]amino]cyclopropane-1-carboxylate (2.15 g, 9.99 mmol, 1.00 equiv) and 4 N HCl in dioxane (20 mL) was stirred for 2 h at room temperature. The resulting mixture was concentrated under reduced pressure to afford the crude title compound (1.52 g, HCl salt) as a white solid. MS-ESI: [M+H]$^+$116

Methyl 1-(4-fluorophenylsulfonamido)cyclopropanecarboxylate

A mixture of methyl 1-aminocyclopropane-1-carboxylate hydrochloride (1.51 g, 9.96 mmol, 1.00 equiv), triethylamine (2.52 g, 24.90 mmol, 2.50 equiv), dichloromethane (20 mL), 4-fluorobenzene-1-sulfonyl chloride (1.95 g, 10.02 mmol, 1.00 equiv) was stirred for 4 h at room temperature. Water (50 mL) was added. The mixture was extracted with dichloromethane (3×50 mL). The combined extracts were washed with water (50 mL) and brine (50 mL) successively. The organic phase was dried over anhydrous sodium sulfate and concentrated under reduced pressure to afford the crude title compound (2.5 g) as yellow oil. MS-ESI: [M+H]$^+$274.

Methyl 1-(4-fluoro-N-isopropylphenylsulfonamido)cyclopropanecarboxylate

A mixture of methyl 1-[(4-fluorobenzene)sulfonamido]cyclopropane-1-carboxylate (1.5 g, 5.49 mmol, 1.00 equiv), 2-iodopropane (5.6 g, 32.94 mmol, 6.00 equiv), and K$_2$CO$_3$ (3.04 g, 22.03 mmol, 4.00 equiv) in CH$_3$CN (30 mL) was stirred overnight at 65° C. in an oil bath. The reaction mixture was then concentrated under reduced pressure. Water (30 mL) and ethyl acetate (50 mL) were added, and phases were separated. The aqueous phase was extracted with ethyl acetate (2×50 mL). The combined extracts were washed with water (2×50 mL) and brine (50 mL), dried over sodium sulfate and concentrated under reduced pressure. The residue was purified by flash chromatography on silica gel, eluting with ethyl acetate/petroleum ether (1:5) to afford the title compound (360 mg) as yellow oil. MS-ESI: [M+H]$^+$ 316

1-(4-Fluoro-N-isopropylphenylsulfonamido)cyclopropanecarboxylic acid

A mixture of methyl 1-[N-(propan-2-yl)(4-fluorobenzene)sulfonamido]cyclopropane-1-carboxylate (250 mg, 0.79 mmol, 1.00 equiv) and potassium hydroxide (265 mg, 4.74 mmo, 6.00 equiv) in methanol/water (24 mL, 5:1) was stirred for 1 h at room temperature. Methanol was stripped off by distillation under reduced pressure. Water (30 mL) was added. The remaining solution was extracted with dichloromethane (3×20 mL). The aqueous phase was acidified by adding concentrated HCl solution to pH-2. The acidic solution was extracted with ethyl acetate (3×50 mL). The combined extracts were washed with water and brine successively, dried over anhydrous sodium sulfate and concentrated under reduced pressure to afford the title compound (40 mg, 17%) as a white solid. MS-ESI: [M−H]$^−$ 300.

1-(4-Fluoro-N-isopropylphenylsulfonamido)-N-((6-(6-(trifluoromethyl)pyridin-3-yl)pyrimidin-4-yl)methyl)cyclopropanecarboxamide A mixture of 1-[N-(propan-2-yl)(4-fluorobenzene)sulfonamido]cyclopropane-1-carboxylic acid (40 mg, 0.13 mmol, 1.00 equiv), 6-[6-(trifluoromethyl)pyridin-3-yl]pyrimidin-4-ylmethanamine (36 mg, 0.14 mmol, 1.07 equiv), HATU (57 mg, 0.15 mmol, 1.13 equiv), DIPEA (40 mg, 0.31 mmol, 2.33 equiv) in DMF (5 mL) was stirred for 2 h at room temperature. Water (20 mL) was added to the reaction mixture. The reaction mixture was then extracted with ethyl acetate (3×30 mL). The extracts were washed with water and brine successively, dried over sodium sulfate and concentrated under reduced pressure. The residue was purified by flash chromatography on silica gel, eluting with ethyl acetate/petroleum ether (2:1) to afford the title compound (25 mg, 35%) as a white solid. MS-ESI: [M+H] 538. $^1$H NMR (400 MHz, DMSO-d$_6$) δ 9.46 (s, 1H), 9.29 (s, 1H), 8.77 (d, J=8 Hz, 1H), 8.16-8.12 (m, 3H), 7.99 (dd, J=8.4, 5.2 Hz, 2H), 7.41 (t, J=8.4 Hz, 2H), 4.47 (s, 2H), 4.19-4.16 (m, 1H), 1.49-1.13 (m, 10H).

Example 85

2-[N-(Propan-2-yl)(4-fluorobenzene)sulfonamido]-N-([6-[4-(trifluoromethyl)cyclohex-1-en-1-yl]pyrimidin-4-yl]methyl)acetamide

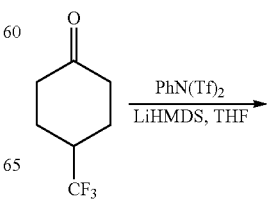

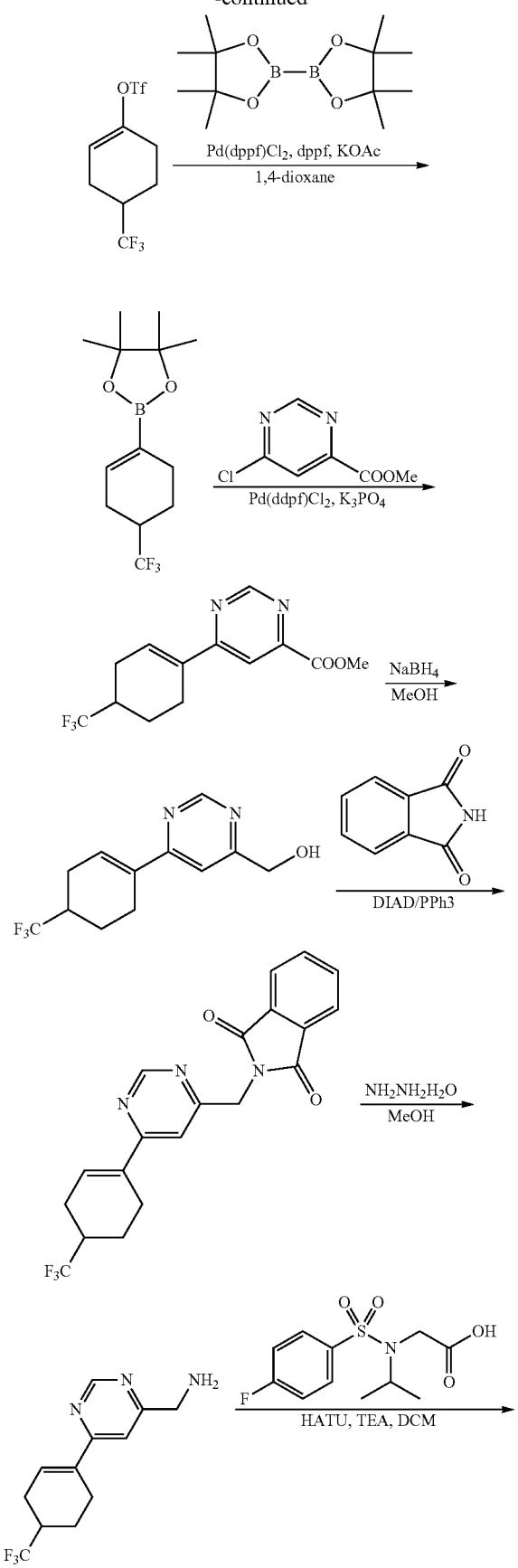

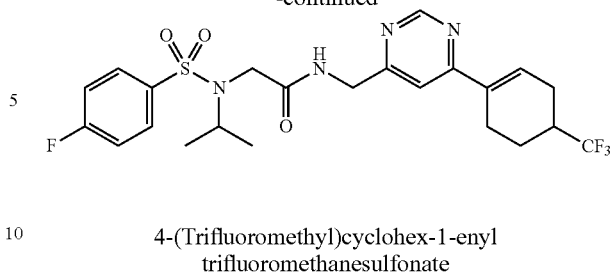

4-(Trifluoromethyl)cyclohex-1-enyl trifluoromethanesulfonate

To a solution of 4-(trifluoromethyl)cyclohexan-1-one (1.00 g, 6.02 mmol, 1.00 equiv) in THF (12 mL) at −78° C. under nitrogen was added dropwise a THF solution of 1 M LiHMDS (6 mL, 1.00 equiv) with stirring. The reaction mixture was stirred for 1 h at −78° C. To this mixture was added dropwise a solution of 1,1,1-trifluoro-N-phenyl-N-(trifluoromethane)sulfonylmethane-sulfonamide (2.152 g, 6.02 mmol, 1.00 equiv) in THF (2 mL) dropwise at −78° C. in 30 min. The mixture was stirred for an additional 2 h at −78° C. and 6 h at room temperature. Then the mixture was partitioned between H$_2$O (50 mL) and ethyl acetate (50 mL). Phases were separated and the aqueous phase was extracted with ethyl acetate (50 ml) twice. The combined organic phase was washed with H$_2$O (2×50 mL), dried over anhydrous sodium sulfate and concentrated under reduced pressure. The residue was purified by flash chromatography on silica gel, eluting with ethyl acetate/petroleum ether (1:20) to afford the title compound (705 mg) as a light yellow solid. GCMS: 298

4,4,5,5-tetramethyl-2-(4-(trifluoromethyl)cyclohex-1-enyl)-1,3,2-dioxaborolane A mixture of 4-(trifluoromethyl)cyclohex-1-en-1-yl trifluoromethanesulfonate (3.636 g, 12.19 mmol, 1.00 equiv), 4,4,5,5-tetramethyl-2-(tetramethyl-1,3,2-dioxaborolan-2-yl)-1,3,2-dioxaborolane (3.626 g, 14.28 mmol, 1.17 equiv), KOAc (3.892 g, 39.66 mmol, 3.25 equiv), Pd(dppf)Cl$_2$ (398 mg, 0.54 mmol, 0.03 equiv), dppf (203 mg, 0.37 mmol, 0.03 equiv) in 1,4-dioxane (60 mL) was stirred under nitrogen overnight at 80° C. The reaction mixture was allowed to cool to room temperature. The reaction mixture was concentrated under reduced pressure. The residue was partitioned between ethyl acetate (50 mL) and water (50 mL), phases were separated. The aqueous phase was extracted with ethyl acetate (2×50 mL). The combined extracts were washed with water (50 mL), dried over anhydrous sodium sulfate and concentrated under reduced pressure. The residue was purified by flash chromatography on silica gel with ethyl acetate:petroleum ether (1:10) to afford the title compound (2.6 g) as a white solid. GCMS: 276.

Methyl 6-(4-(trifluoromethyl)cyclohex-1-enyl)pyrimidine-4-carboxylate

A mixture of 4,4,5,5-tetramethyl-2-[4-(trifluoromethyl)cyclohex-1-en-1-yl]-1,3,2-dioxaborolane (2.00 g, 7.24 mmol, 1.00 equiv), methyl 6-chloropyrimidine-4-carboxylat (1.25 g, 7.27 mmol, 1.00 equiv), Pd(dppf)Cl$_2$.CH$_2$Cl$_2$ (560 mg, 0.10 equiv), K$_2$CO$_3$ (3.1 g, 3.00 equiv), water (4 mL) in 1,4-dioxane (20 mL) was stirred under nitrogen for 2 h at 100° C. and then allowed to cool to room temperature. The mixture was diluted with H$_2$O (120 mL) and extracted with ethyl acetate (3×50 mL). The organic extracts were dried over anhydrous sodium sulfate and concentrated under reduced pressure. The residue was purified by flash chromatography on silica gel, eluting with ethyl acetate/petroleum ether (1:3) to afford the title compound (520 mg) as a yellow solid. MS-ESI: [M+H]$^+$287.

(6-(4-(Trifluoromethyl)cyclohex-1-enyl)pyrimidin-4-yl)methanol

A mixture of methyl 6-[4-(trifluoromethyl)cyclohex-1-en-1-yl]pyrimidine-4-carboxylate (500 mg, 1.75 mmol, 1.00 equiv), NaBH$_4$ (127 mg, 3.36 mmol, 2.00 equiv) in methanol (10 mL) was stirred under reflux for 1 h and then cooled to room temperature. The mixture was concentrated under reduced pressure. The residue was purified by flash chromatography on silica gel, eluting with ethyl acetate/petroleum ether (1:1) to afford the title compound (230 mg) as a off-white solid. MS-ESI: [M+H]$^+$259.

2-((6-(4-(Trifluoromethyl)cyclohex-1-enyl)pyrimidin-4-yl)methyl)isoindoline-1,3-dione A mixture of [6-[4-(trifluoromethyl)cyclohex-1-en-1-yl]pyrimidin-4-yl]methanol (220 mg, 0.85 mmol, 1.00 equiv), 2,3-dihydro-1H-isoindole-1,3-dione (138 mg, 0.94 mmol, 1.10 equiv), DIAD (345 mg, 1.71 mmol, 2.00 equiv), PPh$_3$ (447 mg, 1.70 mmol, 2.00 equiv) in THF (10 mL) was stirred for 2 h at 25° C. and then quenched by the addition of brine (20 mL). The mixture was extracted with dichloromethane (3×20 mL). The combined extracts were washed with brine (20 mL), dried over anhydrous sodium sulfate and concentrated under reduced pressure. The residue was purified by flash chromatography on silica gel, eluting with ethyl acetate/petroleum ether (1:1) to afford the title compound (425 mg) as a white solid. MS-ESI: [M+H]$^+$388.

(6-(4-(Trifluoromethyl)cyclohex-1-enyl)pyrimidin-4-yl)methanamine

A mixture of 2-([6-[4-(trifluoromethyl)cyclohex-1-en-1-yl]pyrimidin-4-yl]methyl)-2,3-dihydro-1H-isoindole-1,3-dione (425 mg, 1.10 mmol, 1.00 equiv), hydrazine hydrate (80%) (687 mg, 13.72 mmol, 10.00 equiv) in methanol (10 mL) was stirred for 3 h at 40° C. and then concentrated under reduced pressure. The mixture was washed with ethyl acetate (2×20 mL) and concentrated under reduced pressure to afford the title compound 211 mg as a white solid. MS-ESI: [M+H]$^+$258.

2-(4-Fluoro-N-isopropylphenylsulfonamido)-N-((6-(4-(trifluoromethyl)cyclohex-1-enyl)pyrimidin-4-yl)methyl)acetamide A mixture of 2-[N-(propan-2-yl)(4-fluorobenzene)sulfonamido]acetic acid (346 mg, 1.26 mmol, 1.20 equiv), HATU (600 mg, 1.58 mmol, 1.50 equiv), DIPEA (407 mg, 3.15 mmol, 3.00 equiv) [6-[4-(trifluoromethyl)cyclohex-1-en-1-yl]pyrimidin-4-yl]methanamine (270 mg, 1.05 mmol, 1.00 equiv) in N,N-dimethylformamide (20 mL) was stirred under nitrogen overnight at 25° C. and then quenched by water (10 mL). The mixture was extracted with dichloromethane (3×100 mL) and the organic layers was washed with brine (2×200 mL) and dried over anhydrous sodium sulfate and concentrated under reduced pressure. The crude product (180 mg) was purified by Prep-HPLC high pH to afford the title compound (71.1 mg, 13%) as a white solid. LCMS (5 cm_ESI_Formic_MeCN): [MH$^+$]=515 at 2.377 min. $^1$H NMR (300 MHz, CD$_3$OD) δ 8.96 (d, J=1.2 Hz, 1H), 8.07-8.02 (m, 2H), 7.80 (s, 1H), 7.37-7.31 (m, 2H), 7.05 (s, 1H), 4.53 (s, 2H), 4.13-4.09 (m, 1H), 3.92 (s, 2H), 2.91-2.43 (m, 7H), 1.72-1.45 (m, 1H), 1.05 (d, J=6.6 Hz, 6H).

Example 86

2-(4-fluoro-N-(4-fluorophenyl)phenylsulfonamido)-N-((6-(6-(trifluoromethyl)pyridin-3-yl)pyrimidin-4-yl)methyl)acetamide Step 1:
4-fluoro-N-(4-fluorophenyl)benzenesulfonamide

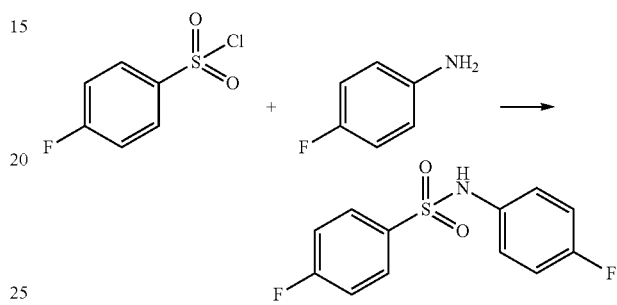

Pyridine (6.11 g, 76.29 mmol) was added dropwise to a stirred solution of 4-fluorobenzene-1-sulfonyl chloride (5.0 g, 25.69 mmol) in dichloromethane (50 mL) at 0° C. Then 4-fluoroaniline (5.67 g, 51.03 mmol) was added slowly to the reaction solution. The reaction was stirred at room temperature overnight, diluted with water (200 mL), and extracted with dichloromethane (3×100 mL). The organic layers were combined and washed with brine (200 mL), dried over anhydrous sodium sulfate, and concentrated under reduced pressure. The residue was purified by flash chromatography on silica gel with ethyl acetate/petroleum ether (0-30%) to afford the title compound (6.13 g) as a light yellow solid. MS-EI: [M+H]$^+$269.

Step 2: methyl 2-(4-fluoro-N-(4-fluorophenyl)phenylsulfonamido)acetate

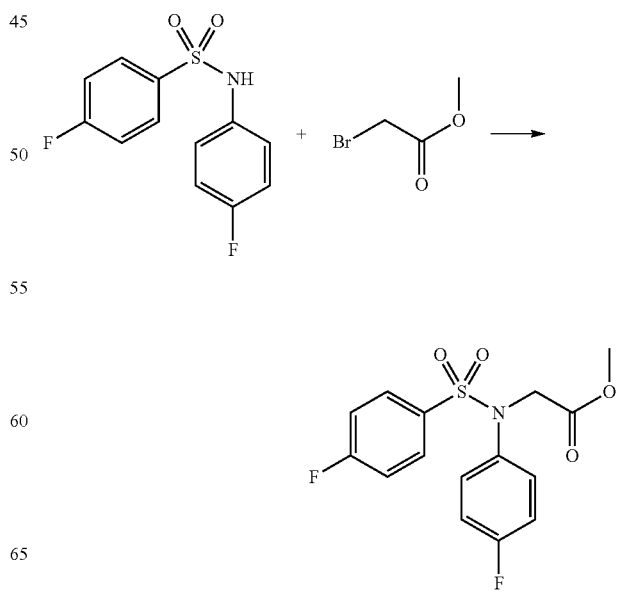

A mixture of sodium hydride (360 mg, 15.00 mmol) in N,N-dimethylformamide (20 mL) was added dropwise to a stirred solution 4-fluoro-N-(4-fluorophenyl)benzene-1-sulfonamide (2 g, 7.43 mmol) in DMF (3 mL) at 0° C. The mixture was warmed to room temperature and stirred for 1 h at room temperature. The reaction was then cooled back to 0° C. and methyl 2-bromoacetate (1.7 g, 11.11 mmol) was added dropwise. The reaction mixture was stirred overnight at room temperature, quenched with ice/water (200 mL), and extracted with dichloromethane (2×200 mL). The organic layers were combined and washed with brine (3×200 mL), dried over anhydrous sodium sulfate, and concentrated under reduced pressure. The residue was purified by flash chromatography on silica gel with ethyl acetate/petroleum ether (0-30% in 30 min) to afford the title compound (1.6 g) as a white solid.

MS-ESI: [M+H]$^+$342.

Step 3: 2-(4-fluoro-N-(4-fluorophenyl)phenylsulfonamido)acetic acid

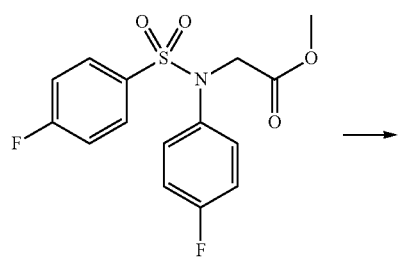

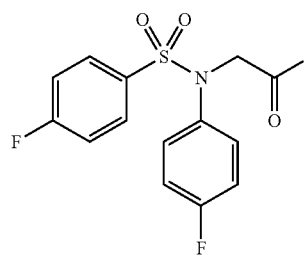

LiOH (560 mg, 23.38 mmol) in water (23.3 mL) was added dropwise to a stirred mixture of methyl 2-[N-(4-fluorophenyl)(4-fluorobenzene)sulfonamido]acetate (1.6 g, 4.69 mmol) in tetrahydrofuran (20 mL) at room temperature. The reaction mixture was stirred overnight at and then the organic solvent was removed under reduced pressure. The pH value of aqueous layer was adjusted to 2-3 with 2M HCl. The solid was collected by filtration to afford the title compound (650 mg) as a white solid.

MS-ESI: [M–H]$^-$ 326.

Step 4: 2-(4-fluoro-N-(4-fluorophenyl)phenylsulfonamido)-N-((6-(6-(trifluoromethyl)pyridin-3-yl)pyrimidin-4-yl)methyl)acetamide

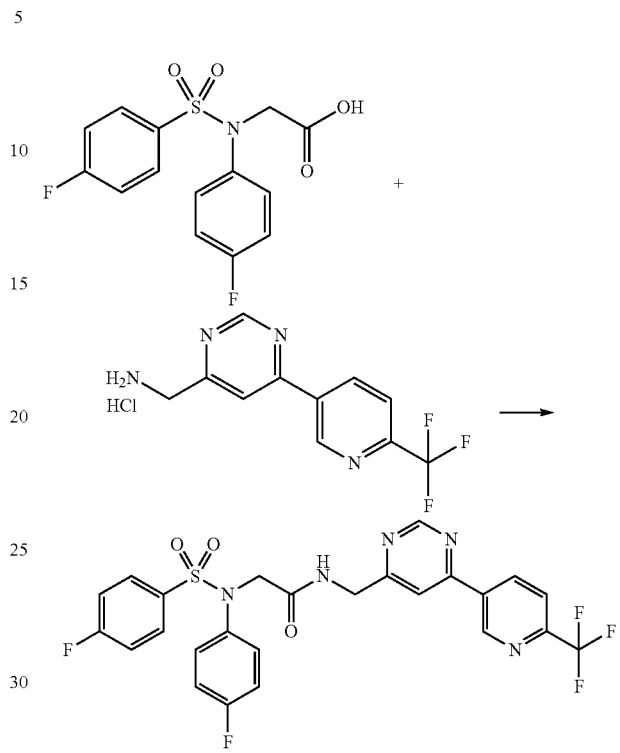

A mixture of 2-[N-(4-fluorophenyl)(4-fluorobenzene)sulfonamido]acetic acid (150 mg, 0.46 mmol), HATU (261.5 mg, 0.69 mmol), DIEA (236.7 mg, 1.83 mmol), and [6-[6-(trifluoromethyl)pyridin-3-yl]pyrimidin-4-yl]methanamine hydrochloride (133 mg, 0.46 mmol) in N,N-dimethylformamide (4 mL, 64.61 mmol) was stirred overnight at room temperature. The crude product (4 mL) was purified by Flash-Prep-HPLC with the following conditions (IntelFlash-1): Column, C18 silica gel; mobile phase, CH$_3$CN:H$_2$O (NH$_4$HCO$_3$) from 36% to 86% within 30 min; Detector, UV 254 nm. This resulted in 31.2 mg of the title compound as a white solid.

LCMS [M+H]$^+$564. $^1$H-NMR (400 MHz, CD$_3$OD) δ 9.45 (s, 1H), 9.23 (d, J=0.8 Hz, 1H), 8.76-8.74 (m, 1H), 8.02 (s, 1H), 7.97 (d, J=8.4 Hz, 1H), 7.74-7.70 (m, 2H), 7.33-7.29 (m, 4H), 7.08-7.03 (m, 2H), 4.63 (s, 2H), 4.43 (s, 2H).

Example 87

IC$_{50}$ Determinations of Exemplified Compounds
Dose Response Assay: Chan Test hTRPA1-CHO Stably Transfected Cell Line

| Cell Culture and Assay Reagents: | |
|---|---|
| Ham's F12 | (GIBCO #11765-047) |
| Tetracycline-free Fetal Bovine Serum | (ClonTech#631106, Lot A301097018) |
| Blasticidin (10 mg/ml stock) | (GIBCO #A11139-02) |
| Zeocin (100 mg/ml stock) | (GIBCO #R250-01) |
| Doxycycline | (SIGMA #D9891) |
| Penicillin-Spreptomycin solution (100X) | (GIBCO #15140-122) |

-continued

| Cell Culture and Assay Reagents: | |
|---|---|
| GlutaMAX (100X) | (GIBCO #35050) |
| Trypsin-EDTA | (GIBCO #25200-056) |
| PBS (without Calcium and Magnesium) | (GIBCO #14190) |
| HBSS | (GIBCO #14025) |
| Hepes | (GIBCO #15630) |
| BSA (fatty acid free, low endotoxin) | (SIGMA #A8806-5G) |
| DMSO | (SIGMA #D2650) |
| AP-18 | (SIGMA #A7232) |
| Cinnamaldehyde | (SIGMA #W228613) |
| ATP | (SIGMA #A-6419) |
| 2-Aminoethyl diphenylborinate | (SIGMA #D9754) |
| Menthol | (Sigma #M2772) |
| FLIPR Calcium 3 Assay Kit | (Molecular Devices #R8108) |
| Probenecid | (INVITROGEN #36400) |
| Plates | (BD #35-3962) |

CHO-K1 Tet-On_HOMSA_TRPA1_Clone_20
   Chinese Hamster Ovary cells, inducible expression
   Clone #20, received at passage #26
   Channel expression in this cell line has been shown to be stable for at least 80 passages
     Verified *Mycoplasma* free with MycoAlert Kit
     Cell line expanded and banked
Growth Conditions:
Growth Media for CHO-K1 Tet-On_HOMSA_TRPA1_Clone_20
   Ham's F-12 with 10% tetracycline-free FBS
   1× penicillin-streptomycin
   1× glutamax
   0.01 mg/ml Blasticidin
   0.40 mg/ml Zeocin
   The cell line doubling rate was ~15 hours. The culture plates did not exceed 80% confluency.
   To induce expression, tetracycline was added to blasticidin/zeocin-free media at a final concentration of 1 ug/ml. Experiments were run at 24 hours post induction.
Plating Conditions CHOK1/TRPA1 Cells:
   Harvested cells with 0.025% trypsin/EDTA.
   Resuspended cells in growth media without selection antibiotics.
   Measured cell density and diluted to $2.4 \times 10^5$ cells/ml in media containing 1 ug/ml Doxycycline Plate 25 ul/well into 384 well black/clear tissue culture-treated plates.
   Incubated overnight at 37° C.
Calcium Flux Assay:
Day of Assay:
Reagents:
   Replacement Buffer: Hank's Balanced Salt Solution, 20 mM HEPES along with 0.005% BSA and 2× Probenecid
   Dye Loading Buffer: Cal-3 NW Calcium dye was prepared by dissolving the contents of one vial with 500 ml Hank's Balanced Salt Solution containing 20 mM HEPES.
   Control compounds for CHOK1/TRPA1 cells:
AP-18, stock 10 mM, prepare 3.5× compound dilution in a Compound Buffer (HBSS/20 mM HEPES/0.005% BSA)—final concentration 10 uM.
   Preparation of Cinnamaldehyde (agonist addition):
     FW=132.16
     Specific gravity=1.046 gm/cc
     1.32 gm/1.046 gm/cc=1.26 ml of stock
     Add 1.74 ml DMSO=3.3 M stock
     Working solution 4.5× (final 100 uM in Compound Buffer: HBSS/20 mM HEPES/0.005% BSA)
Compounds dilutions were prepared from 5 or 10 mM stock (100% DMSO):
   Adjustments of volumes and concentrations were made at time of titration to reflect desired final assay concentrations.
   Compounds were tested at either 20 μM three folds dilution 11 steps out or 30 μM two folds dilution 11 steps out.
   3 μl of diluted compound were transferred into Weidmann 384-well plate in duplicates side-by-side.
   Compound plates were resuspended with 100 ul of HBSS/20 mM HEPES/0.005% BSA buffer (Compound Buffer):
     column 1A-H: buffer/DMSO (bk)
     column 2A-H: AP-18 (control antagonist for CHOK1 TRPA1 cells)
     column 1I-P: ATP (control for CHOK1 teton cells)
     column 2 I-P: 2APB (control antagonist for CHOK1/TRPM8 cells).
Growth media was removed from the cell plates (20 ul) and 20 ul of the Replacement Buffer was added followed by addition of 25 ul of diluted dye. All three steps were performed using a Plate Washer BioTek 407. The plates were then incubated for 30' at RT.
After incubation, both the cell and compound plates were brought to the FLIPR and 20 ul of the diluted compounds/antagonist/bk were transferred to the cell plates by the FLIPR. Plates were then incubated for 30' at room temperature. After 30' incubation, plates were returned to the FLIPR and 20 ul of 4.5× Cinnamaldehyde was added to the cell plates. During the compound addition as well as agonist addition, fluorescence readings were taken simultaneously from all 384 wells of the cell plate every 1.5 seconds. Five readings were taken to establish a stable baseline, then 20 ul of sample was rapidly (30 ul/sec) and simultaneously added to each well of the cell plate. The fluorescence was continuously monitored before, during and after sample/agonist addition for a total elapsed time of 100 seconds (compound addition) and 120 seconds (agonist addition). Responses (increase in peak fluorescence) in each well following agonist addition was determined. The initial fluorescence reading from each well, prior to ligand stimulation, was used a zero baseline value for the data from that well. The responses were expressed as % inhibition of the inhibitor control as shown in Table 1 below:

TABLE 1

| Example | IC50 (FLIPR) μM |
|---|---|
| 1 | 0.081 |
| 2 | 0.035 |
| 3 | 1.08 |
| 4 | 1.12 |
| 5 | 1.62 |
| 6 | 1.11 |
| 7 | 0.8 |
| 8 | 0.15 |
| 9 | 1.5 |
| 10 | 4.8 |
| 11 | 0.13 |
| 12 | 0.048 |
| 13 | 0.26 |
| 14 | 0.037 |
| 15 | 0.028 |
| 16 | 0.024 |

TABLE 1-continued

| Example | IC50 (FLIPR) μM |
|---|---|
| 17 | 4.83 |
| 18 | 4.81 |
| 19 | 0.098 |
| 20 | 0.16 |
| 21 | 0.097 |
| 22 | 0.19 |
| 23 | 0.029 |
| 24 | 1.03 |
| 25 | 0.042 |
| 26 | 0.34 |
| 27 | 0.052 |
| 28 | 0.033 |
| 29 | 0.47 |
| 30 | 0.22 |
| 31 | 0.38 |
| 32 | 0.19 |
| 33 | 2.21 |
| 34 | 3.66 |
| 35 | 0.054 |
| 36 | 0.012 |
| 37 | 0.014 |
| 38 | 0.064 |
| 39 | 0.051 |
| 40 | 0.067 |
| 41 | 0.29 |
| 42 | 0.084 |
| 43 | 0.38 |
| 44 | 0.087 |
| 45 | 0.048 |
| 46 | 0.13 |
| 47 | 0.041 |
| 48 | 0.034 |
| 49 | 0.07 |
| 50 | 0.079 |
| 51 | 0.13 |
| 52 | 0.098 |
| 53 | 0.048 |
| 54 | 1.76 |
| 55 | 0.13 |
| 56 | 0.55 |
| 57 | 0.18 |
| 58 | 0.23 |
| 59 | 0.099 |
| 60 | 0.2 |
| 61 | 0.14 |
| 62 | 0.26 |
| 63 | 0.038 |
| 64 | 0.083 |
| 65 | 3.86 |
| 66 | 0.17 |
| 67 | 0.38 |
| 68 | 0.047 |
| 69 | 0.019 |
| 70 | 0.048 |
| 71 | 0.079 |
| 72 | 0.233 |
| 73 | 0.682 |
| 74 | 0.298 |
| 75 | 0.025 |
| 76 | 0.020 |

Example 88

IC$_{50}$ Determinations of Exemplified Compounds

IC$_{50}$s (effective concentration) of compounds on the human TRPA1 channel were determined using a Hamamatsu FDSS fluorescence plate reader. CHO cells expressing human TRPA1 were plated into 384-well plates, incubated overnight at 37° C., and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using the FDSS while monitoring fluorescence to determine whether any of the test compounds have TRPA1 agonist activity. Plates were then incubated with compound for 20 minutes at room temperature prior to adding agonist. Following this incubation, 100 mM cinnamaldehyde was added to all wells of the plate and block of this cinnamaldehyde induced calcium influx was measured.

IC$_{50}$s were fit with a standard Hill function, keeping the Hill coefficient (n) fixed to 1.5. Fixing the Hill coefficient will generally reduce variability of the IC$_{50}$ determination. The IC$_{50}$s were examined by eye to make sure the MIN and MAX points were set correctly prior to validation of the results. Data for representative compounds of formula (I) is provided in Table 2 below.

TABLE 2

| Example | hTRPA1 AUC IC$_{50}$ (μM) |
|---|---|
| 77 | 0.883 |
| 78 | 1.0 |
| 79-(R) | 0.055 |
| 79-(S) | 0.038 |
| 80 | 0.251 |
| 81 | 3.0 |
| 82 | 2.4 |
| 83 | 0.058 |
| 84 | 0.029 |
| 85 | 0.013 |
| 86 | 0.009 |

It is to be understood that the invention is not limited to the particular embodiments of the invention described above, as variations of the particular embodiments may be made and still fall within the scope of the appended claims. All documents cited to or relied upon herein are expressly incorporated by reference.

We claim:

1. A compound of formula (I):

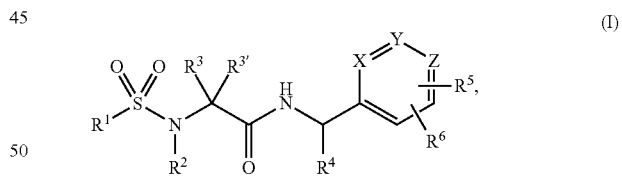

wherein:
R$^1$ is unsubstituted phenyl, phenyl mono- or bi-substituted independently with halogen or —CN, an unsubstituted five- or six-membered heteroaryl ring or a five- or six-membered heteroaryl ring substituted with lower alkyl, halogen, or haloalkyl;

R$^2$ is selected from the group consisting of methyl, —CH$_2$CF$_3$, ethyl, hydroxy-ethyl, propyl, hydroxy-propyl, cyclopropyl, isopropyl, methoxy-ethyl, tert-butyl, oxetan-3-ylmethyl or oxetanyl;

R$^3$ and R$^{3'}$ are each independently selected from the group consisting of hydrogen; deuterium; haloalkyl; cycloalkyl and lower alkyl wherein said haloalkyl, cycloalkyl and lower alkyl is optionally substituted with deuterium, F, Cl, Br, hydroxyl or alkoxy; or R$^3$ and R³' taken together with the carbon to which they are attached form a 3, 4, 5, or 6-membered cycloalkyl optionally substituted with deuterium, F, Cl, Br, hydroxyl or alkoxy;
R⁴ is hydrogen or lower alkyl;
and
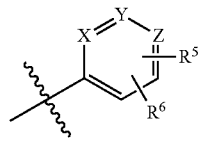
is selected from:
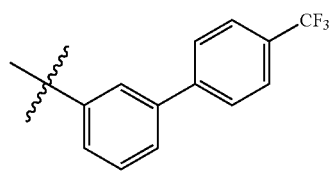
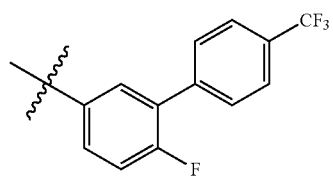
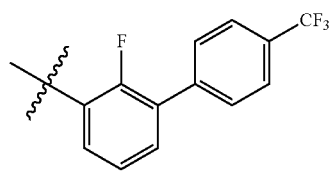
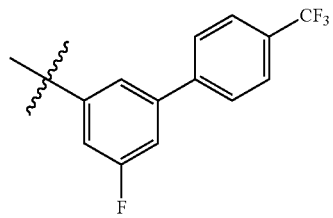
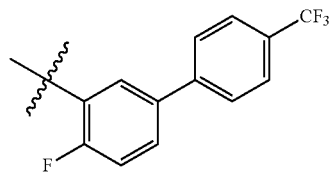
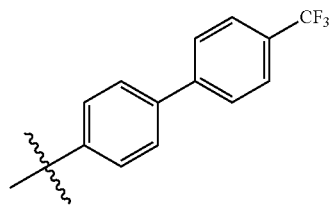
-continued
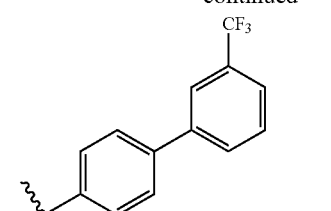
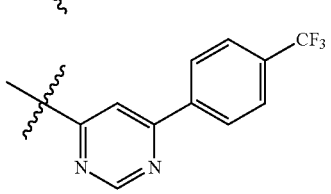
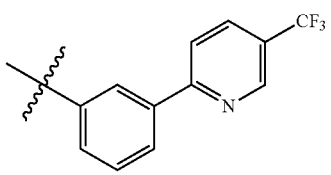
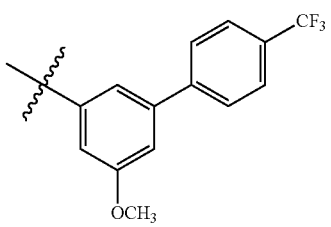
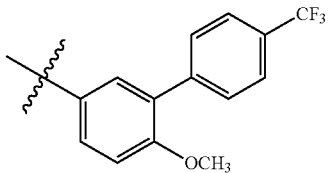
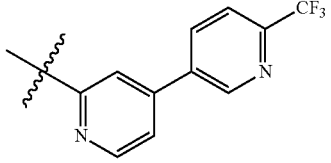
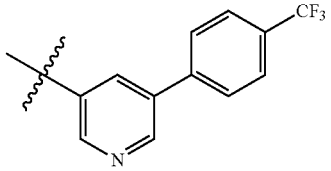
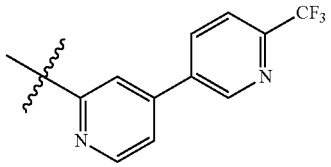
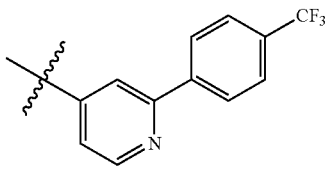

-continued

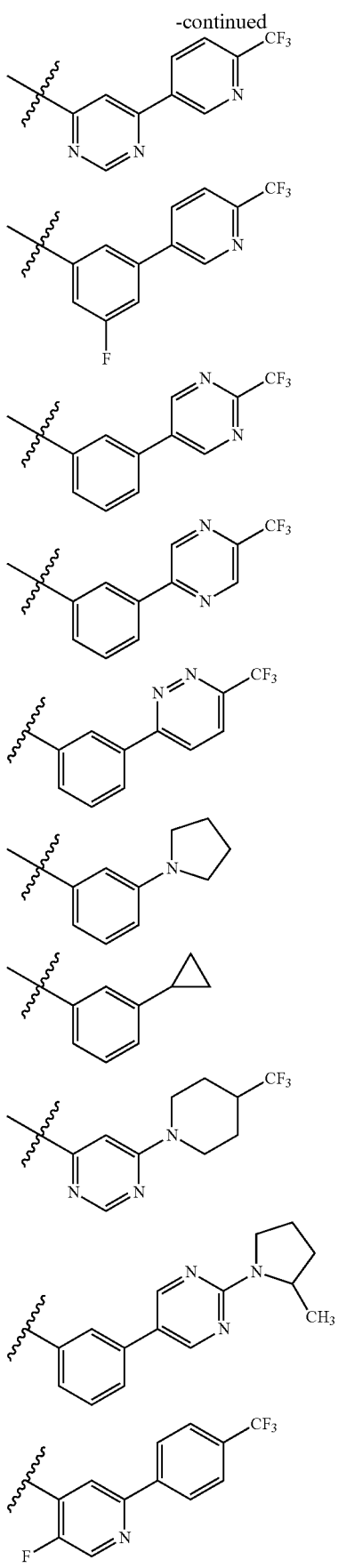

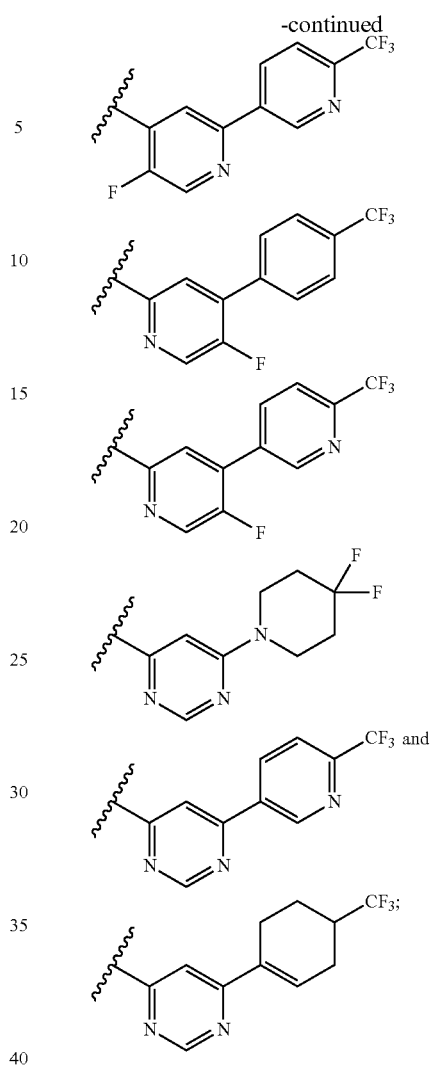

or a pharmaceutically acceptable salt thereof.

2. The compound according to claim 1, wherein $R^1$ is phenyl optionally substituted with cyano, F or Cl, pyrazinyl optionally substituted with F or Cl, pyridinyl optionally substituted with F or Cl, pyrazole optionally substituted with F or Cl, or thienyl, optionally substituted with F or Cl.

3. The compound according to claim 1, wherein $R^1$ is phenyl substituted with F or Cl, pyrazinyl substituted with F or Cl, pyridinyl substituted with F or Cl, or thiophenyl substituted with F or Cl.

4. The compound according to claim 1, wherein $R^2$ is methyl, —$CH_2CF_3$, ethyl, hydroxy-ethyl, 2-hydroxypropyl, cyclopropyl, isopropyl, 2-methoxyethyl, tert-butyl, methoxymethyl, oxetan-3-ylmethyl, 4-fluorophenyl, or 3-oxetanyl.

5. The compound according to claim 1, wherein $R^3$ and $R^{3'}$ are both hydrogen.

6. The compound according to claim 1, wherein one of $R^3$ or $R^{3'}$ is hydrogen and the other is methyl, tert-butyl, cyclopropyl, —$CH_2OH$ or —$CH_2OCH_3$.

7. The compound according to claim 1, wherein one of $R^3$ or $R^{3'}$ is hydrogen, deuterium, or methyl, and the other is hydrogen, methyl, isopropyl, cyclopropyl, hydroxymethyl, methoxymethyl, or deuterium; or $R^3$ and $R^{3'}$ taken together with the carbon to which they are attached form a 3-membered cycloalkyl.

8. The compound according to claim 1, wherein $R^4$ is hydrogen.

9. The compound according to claim 1, wherein $R^4$ is methyl.

10. A compound selected from:
2-(4-fluoro-N-isopropylphenylsulfonamido)-N-(3-(pyrrolidin-1-yl)benzyl)acetamide;
N-(3-cyclopropylbenzyl)-2-(4-fluoro-N-isopropylphenylsulfonamido)acetamide;
R)-2-(4-fluoro-N-isopropylphenylsulfonamido)-N-(3-(2-(2-methylpyrrolidin-1-yl)pyrimidin-5-yl)benzyl)acetamide;
(S)-2-(4-fluoro-N-isopropylphenylsulfonamido)-N-(3-(2-(2-methylpyrrolidin-1-yl)pyrimidin-5-yl)benzyl)acetamide;
2-(4-Fluoro-N-isopropylphenylsulfonamido)-N-((6-(4-(trifluoromethyl)piperidin-1-yl)pyrimidin-4-yl)methyl)acetamide;
N-((6-(4,4-Difluoropiperidin-1-yl)pyrimidin-4-yl)methyl)-2-(4-fluoro-N-isopropylphenylsulfonamido)acetamide;
2-(N-Isopropyl-1-methyl-1H-pyrazole-3-sulfonamido)-N-((4'-(trifluoromethyl)biphenyl-3-yl)methyl)acetamide;
2,2-Dideuterio-2-(4-fluoro-N-isopropylphenylsulfonamido)-N-((6-(6-(trifluoromethyl)pyridin-3-yl)pyrimidin-4-yl)methyl)acetamide;
1-(4-Fluoro-N-isopropylphenylsulfonamido)-N-((6-(6-(trifluoromethyl)pyridin-3-yl)pyrimidin-4-yl)methyl)cyclopropanecarboxamide;
(6-(6-(Trifluoromethyl)pyridin-3-yl)pyrimidin-4-yl)methyl-2-(4-fluoro-N-isopropylphenylsulfonamido)acetate; or
2-[N-(Propan-2-yl)(4-fluorobenzene)sulfonamido]-N-([6-[4-(trifluoromethyl)cyclohex-1-en-1-yl]pyrimidin-4-yl]methyl)acetamide;
or a salt thereof.

11. A compound of formula (I):

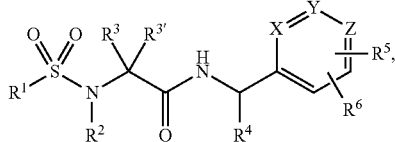

(I)

wherein:

two of X, Y or Z are N and the other is C or CH;

$R^1$ is unsubstituted phenyl, phenyl mono- or bi-substituted independently with halogen or —CN, an unsubstituted five- or six-membered heteroaryl ring or a five- or six-membered heteroaryl ring substituted with lower alkyl, halogen, or haloalkyl;

$R^2$ is selected from the group consisting of methyl, —$CH_2CF_3$, ethyl, hydroxy-ethyl, propyl, hydroxy-propyl, cyclopropyl, isopropyl, methoxy-ethyl, tert-butyl, oxetan-3-ylmethyl or oxetanyl;

$R^3$ and $R^{3'}$ are each independently selected from the group consisting of hydrogen; deuterium; haloalkyl; cycloalkyl and lower alkyl wherein said haloalkyl, cycloalkyl and lower alkyl is optionally substituted with deuterium, F, Cl, Br, hydroxyl or alkoxy; or $R^3$ and $R^{3'}$ taken together with the carbon to which they are attached form a 3, 4, 5, or 6-membered cycloalkyl optionally substituted with deuterium, F, Cl, Br, hydroxyl or alkoxy;

$R^4$ is hydrogen or lower alkyl;

$R^5$ is trifluoromethylphenyl, 5-trifluoromethylpyrid-2-yl, 6-trifluoromethylpyrid-3-yl, 6-trifluoromethylpyridazin-3-yl, 2-trifluoromethylpyrimidin-5-yl, 5-trifluoromethylpyrazin-2-yl, pyrrolidino, cyclopropyl, 4,4-difluoropiperidino, 4-trifluoromethylpiperidino, 2-(2-methylpyrrolidino)pyrimidin-5-yl, or 4-trifluoromethylcyclohex-1-ene; and $R^6$ is hydrogen, halogen or alkoxy, or a pharmaceutically acceptable salt thereof.

12. The compound according to claim 11, wherein $R^6$ is hydrogen.

13. The compound according to claim 11, wherein $R^6$ is F or methoxy.

14. The compound according to claim 11, wherein $R^6$ is halogen or alkoxy.

* * * * *